(12) United States Patent
Bue-Valleskey et al.

(10) Patent No.: US 6,221,838 B1
(45) Date of Patent: *Apr. 24, 2001

(54) METHODS OF TREATING NEUROPEPTIDE Y-ASSOCIATED CONDITIONS

(75) Inventors: Juliana Maude Bue-Valleskey; Mark Louis Heiman; Thomas Wesley Stephens; Frank C. Tinsley, all of Indianapolis, IN (US)

(73) Assignee: Eli Lilly and Company, Indianapolis, IN (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/674,774

(22) Filed: Jun. 28, 1996

Related U.S. Application Data

(60) Provisional application No. 60/005,911, filed on Oct. 27, 1995, provisional application No. 60/005,910, filed on Oct. 27, 1995, provisional application No. 60/000,752, filed on Jun. 30, 1995, and provisional application No. 60/000,740, filed on Jun. 30, 1995.

(51) Int. Cl.[7] ............................ A61K 38/00; A61K 38/12
(52) U.S. Cl. .................. 514/9; 514/12; 514/324; 514/422; 514/428; 514/448; 514/333; 514/578; 514/866; 514/909
(58) Field of Search .................. 514/9, 12, 324, 514/428, 448, 909, 866, 578, 333, 422

(56) References Cited

U.S. PATENT DOCUMENTS

| | | | |
|---|---|---|---|
| 5,552,523 | * 9/1996 | Basinski et al. | 530/324 |
| 5,567,714 | * 10/1996 | Bruns, Jr. et al. | 514/324 |

OTHER PUBLICATIONS

Dayhuff, Atlas of Proteine Sequence & Structure (1972) vol 5 pp 89–99.*

* cited by examiner

*Primary Examiner*—Bennett Celsa
(74) *Attorney, Agent, or Firm*—Alexander Wilson; Paul J. Gaylo

(57) ABSTRACT

This invention describes methods of treating conditions associated with an excess of neuropeptide Y which comprises administering an analog of an obesity protein. This invention further describes methods of treating conditions associated with an excess of neuropeptide Y which coomprises administering an analog of an obesity protein in combination with a neuropeptide Y antagonist. This invention demonstrates that the obesity protein acts by reducing the production of neuropeptide Y by the hypothalamus.

16 Claims, No Drawings

METHODS OF TREATING NEUROPEPTIDE Y-ASSOCIATED CONDITIONS

This application claims benefit to U.S. provisional application Ser. No. 60/000,752, filed Jun. 30, 1995; U.S. provisonal application Ser. No. 60/000,740, filed Jun. 30, 1995; U.S. provisional application Ser. No. 60/005,910, filed Oct. 27, 1995; and U.S. provisional application Ser. No. 60/005,911, filed Oct. 27, 1995.

BACKGROUND OF THE INVENTION

Neuropeptide Y is a peptide present in the central and peripheral nervous systems. The peptide co-exists with noradrenaline in many neurons and acts as a neurotransmitter per se or synergistically together with noradrenaline. Neuropeptide Y-containing fibers are numerous around arteries in the heart, but are also found around the arteries in the respiratory tract, the gastrointestinal tract, and the genitourinary tract. Neuropeptide Y is also present in the cerebrum with effects on blood pressure, feeding, and the release of different hormones. Alterations in central concentrations of neuropeptide Y have been implicated in the etiology of psychiatric disorders.

Neuropeptide Y was discovered, isolated and sequenced about ten years ago from porcine brain as part of a general screening protocol to discover carboxy-terminal amidated peptides and was named neuropeptide Y due to its isolation form neural tissue and the presence of tyrosine as both the amino and carboxy terminal amino acid. Neuropeptide Y is a member of the pancreatic family of peptides and shares significant sequence homology with pancreatic polypeptide, and peptide YY.

Neuropeptide Y and the other members of its family of peptides all feature a tertiary structure consisting of an N-terminal polyproline helix and an amphiphilic α-helix, connected with a β-turn, creating a hairpin-like loop, which is sometimes referred to as the pancreatic polypeptide (PP) fold. The helices are kept together by hydrophobic interactions. The amidated C-terminal end projects away from the hairpin loop.

Subsequent to its discovery neuropeptide Y was identified as being the most abundant peptide in the central nervous system with widespread distribution including the cortex, brainstem, hippocampus, hypotahlamus, amygdala, and thalamus as well as being present in the peripheral nervous system in sympathetic neurons and adrenal chromaffin cells.

Neuropeptide Y seems to fulfill the main neurotransmitter criteria, since it is stored in synaptic granules, is released upon electrical nerve stimulation, and acts at specific receptors. It is clear that neuropeptide Y is an important messenger in its own right, probably in the brain, where neuropeptide Y potently inhibits the activity of adenylate cyclase and induces an increase in the intracellular levels of calcium. Central injection of neuropeptide Y results in blood pressure changes, increased feeding, increased fat storage, elevated blood sugar and insulin, decreased locomotor activity, reduced body temperature, and catalepsy.

Neuropeptide Y (as well as its chemical relatives) acts upon membrane receptors that are dependent on guanine nucleotides, known as G protein-coupled receptors. G proteins are a family of membrane proteins that become activated only after binding guanosine triphosphate. Activated G proteins in turn activate an amplifier enzyme on the inner face of a membrane; the enzyme then converts precursor molecules into second messengers.

Neuropeptide Y appears to interact with a family of closely related receptors. These receptors are generally classified into several subtypes based upon the ability of different tissues and receptors to bind different fragments of neuropeptide Y and the closely related peptide YY. The Y1 receptor subtype appears to be the major vascular neuropeptide Y receptor. The Y2 receptor subtypes can also occur postjunctionally on vascular smooth muscle. The as-yet-unisolated Y3 receptor subtype appears to be neuropeptide Y-specific, not binding peptide YY. This receptor is likely to be present in the adrenal tissues, medulla, heart, and brain stem, among other areas. [For a review of neuropeptide Y and neuropeptide Y receptors, see, e.g., C. Wahlestedt and D. Reis, *Annual Review of Pharmacology and Toxicology*, 33:309–352 (1993)]. Patent Cooperation Treaty Publication WO 95/00161, published Jun. 18, 1993, describes a series of neuropeptide Y antagonists and agonists for controlling biological activities such as obesity and cardiovascular function.

Obesity, and especially upper body obesity, is a common and very serious public health problem in the United States and throughout the world. According to recent statistics, more than 25% of the United States population and 27% of the Canadian population are overweight. Kuczmarski, *American Journal of Clinical Nutrition*, 55: 495S–502S (1992); Reeder et. al., *Canadian Medical Association Journal*, 23:226–233 (1992). Upper body obesity is the strongest risk factor known for type II diabetes mellitus, and is a strong risk factor for cardiovascular disease and cancer as well. Recent estimates for the medical cost of obesity are US$150,000,000,000 world wide. The problem has become serious enough that the surgeon general has begun an initiative to combat the ever increasing adiposity rampant in American society.

Much of this obesity-induced pathology can be attributed to the strong association with dyslipidemia, hypertension, and insulin resistance. Many studies have demonstrated that reduction in obesity by diet and exercise reduces these risk factors dramatically. Unfortunately, these treatments are largely unsuccessful with a failure rate reaching 95%. This failure may be due to the fact that the condition is strongly associated with genetically inherited factors that contribute to increased appetite, preference for highly caloric foods, reduced physical activity, and increased lipogenic metabolism. This indicates that people inheriting these genetic traits are prone to becoming obese regardless of their efforts to combat the condition. Therefore, a pharmacological agent that can correct this adiposity handicap and allow the physician to successfully treat obese patients in spite of their genetic inheritance is needed.

The ob/ob mouse is a model of obesity and diabetes that is known to carry an autosomal recessive trait linked to a mutation in the sixth chromosome. Recently, Yiying Zhang and co-workers published the positional cloning of the mouse gene (ob) linked with this condition. Yiying Zhang et al. *Nature* 372: 425–32 (1994). This report disclosed a gene coding for a 167 amino acid protein with a 21 amino acid signal peptide that is exclusively expressed in adipose tissue.

Physiologists have postulated for years that, when a mammal overeats, the resulting excess fat signals to the brain that the body is obese which, in turn, causes the body to eat less and burn more fuel. G. R. Hervey, *Nature (London)*, 227:629–631 (1969). This "feedback" model is supported by parabiotic experiments, which implicate a circulating hormone controlling adiposity Based on this model, the protein, which is apparently encoded by the ob gene, is now speculated to be an adiposity regulating hormone.

Pharmacological agents which are biologically active and mimic the activity of this protein are useful to help patients regulate their appetite and metabolism and thereby control their adiposity.

The present invention provides biologically active anti-obesity proteins. Most significantly, the claimed proteins have improved properties due to their lower isoelectric points. Thus, they are more readily formulated and stored. Furthermore, the present compounds are more pharmaceutically elegant, which results in superior delivery of therapeutic doses. In view of the wide number of clinical maladies associated with an excess of neuropeptide Y and related peptides, the development of compounds that inhibit release of neuropeptide Y as well as neuropeptide Y receptor antagonists will serve to control these clinical conditions.

SUMMARY OF THE INVENTION

This invention encompasses methods for the treatment or prevention of a physiological disorder associated with an excess of neuropeptide Y, which method comprises administering to a mammal in need of said treatment an effective amount of an analog of an obesity protein.

In a series of embodiments this invention encompasses methods for the treatment or prevention of a physiological disorder associated with an excess of neuropeptide Y, which method comprises administering to a mammal in need of said treatment an effective amount of a compound of the formula

```
Val Pro Ile Gln Lys Val Gln Asp Asp Thr Lys Thr
1               5                       10

Leu Ile Lys Thr Ile Val Thr Arg Ile Xaa Asp Ile
        15                  20

Ser His Xaa Xaa Ser Val Ser Ser Lys Gln Lys Val
25                  30                      35

Thr Gly Leu Asp Phe Ile Pro Gly Leu His Pro Ile
            40                  45

Leu Thr Leu Ser Lys Xaa Asp Gln Thr Leu Ala Val
    50              55                      60

Tyr Gln Gln Ile Leu Thr Ser Xaa Pro Ser Arg Xaa
                65              70

Val Ile Gln Ile Xaa Asn Asp Leu Glu Asn Leu Arg
        75                  80

Asp Leu Leu His Val Leu Ala Phe Ser Lys Ser Cys
85                  90                      95

His Leu Pro Trp Ala Ser Gly Leu Glu Thr Leu Asp
            100                 105

Ser Leu Gly Gly Val Leu Glu Ala Ser Xaa Tyr Ser
    110                 115                 120

Thr Glu Val Val Ala Leu Ser Arg Leu Gln Gly Ser
            125                 130

Leu Gln Asp Met Leu Trp Gln Leu Asp Leu Ser Pro
        135                 140

145
Gly Cys
``` wherein:

Xaa at position 22 is Asn, Asp or Glu;
Xaa at position 27 is Thr or Ala;
Xaa at position 28 is Gln, Glu, or absent;
Xaa at position 54 is Met or Ala;
Xaa at position 68 is Met or Leu;
Xaa at position 72 is Asn, Asp or Glu;
Xaa at position 77 is Ser or Ala;
Xaa at position 118 is Gly or Leu;
said protein having at least one substitution selected from the group consisting of:

His at position 97 is replaced with Gln, Asn, Ala, Gly, Ser, or Pro;
Trp at position 100 is replaced with Ala, Glu, Asp, Asn, Met, Ile, Phe, Tyr, Ser, Thr, Gly, Gln, or Leu;
Ala at position 101 is replaced with Ser, Asn, Gly, His, Pro, Thr, or Val;
Ser at position 102 is replaced with Arg;
Gly at position 103 is replaced with Ala;
Glu at position 105 is replaced with Gln;
Thr at position 106 is replaced with Lys or Ser;
Leu at position 107 is replaced with Pro;
Asp at position 108 is replaced with Glu; or
Gly at position 111 is replaced with Asp.

hereinafter referred to as SEQ ID NO: 1, or a pharmaceutically acceptable salt or solvate thereof.

In another embodiment this invention provides methods of treating disorders associated with an excess of neuropeptide Y, which comprises administering an analog of an obesity protein, in combination with a compound having activity as a neuropeptide Y antagonist.

In yet another embodiment, this invention provides pharmaceutical formulations, useful in treating a condition associated with an excess of neuropeptide Y, which comprises admixing an analog of an obesity protein with a compound having activity as a neuropeptide Y antagonist, in combination with one or more pharmaceutically acceptable carriers, diluents, or excipients therefor.

DETAILED DESCRIPTION AND PREFERRED EMBODIMENTS

The terms and abbreviations used in this document have their normal meanings unless otherwise designated. For example "° C." refers to degrees Celsius; "N" refers to normal or normality; "mmol" refers to millimole or millimoles; "g" refers to gram or grams; "ml" means milliliter or milliliters; "M" refers to molar or molarity; "µg" refers to microgram or micrograms; and "µl" refers to microliter or microliters.

The amino acids abbreviations are as set forth in 37 C.F.R. § 1.822 (b)(2) (1994). One skilled in the art would recognize that certain amino acids are prone to rearrangement. For example, Asp may rearrange to aspartimide and isoaspargine as described in I. Schön, et al., *International Journal of Peptide and Protein Research*, 14:485–94 (1979) and references cited therein. These rearrangement derivatives are included within the scope of the present invention. Unless otherwise indicated the amino acids are in the L configuration.

All nucleic acid sequences, unless otherwise designated, are written in the direction from the 5' end to the 3' end, frequently referred to as "5' to 3'".

All amino acid or protein sequences, unless otherwise designated, are written commencing with the amino terminus ("N-terminus") and concluding with the carboxy terminus ("C-terminus").

"Base pair" or "bp" as used herein refers to DNA or RNA. The abbreviations A,C,G, and T correspond to the 5'-monophosphate forms of the deoxyribonucleosides (deoxy)adenine, (deoxy)cytidine, (deoxy)guanine, and (deoxy)thymine, respectively, when they occur in DNA molecules. The abbreviations U,C,G, and T correspond to the 5'-monophosphate forms of the ribonucleosides uracil, cytidine, guanine, and thymine, respectively when they occur in RNA molecules. In double stranded DNA, base pair may refer to a partnership of A with T or C with G. In a DNA/RNA, heteroduplex base pair may refer to a partnership of A with U or C with G. (See the definition of "complementary", infra.)

The terms "digestion" or "restriction" of DNA refers to the catalytic cleavage of the DNA with a restriction enzyme that acts only at certain sequences in the DNA ("sequence-specific endonucleases"). The various restriction enzymes used herein are commercially available and their reaction conditions, cofactors, and other requirements were used as would be known to one of ordinary skill in the art. Appropriate buffers and substrate amounts for particular restriction enzymes are specified by the manufacturer or can be readily found in the literature.

"Ligation" refers to the process of forming phosphodiester bonds between two double stranded nucleic acid fragments. Unless otherwise provided, ligation may be accomplished using known buffers and conditions with a DNA ligase, such as T4 DNA ligase.

The term "plasmid" refers to an extrachromosomal (usually) self-replicating genetic element. Plasmids are generally designated by a lower case "p" preceded and/or followed by letters and/or numbers. The starting plasmids herein are either commercially available, publicly available on an unrestricted basis, or can be constructed from available plasmids in accordance with published procedures. In addition, equivalent plasmids to those described are known in the art and will be apparent to the ordinarily skilled artisan.

The term "reading frame" means the nucleotide sequence from which translation occurs "read" in triplets by the translational apparatus of transfer RNA (tRNA) and ribosomes and associated factors, each triplet corresponding to a particular amino acid. A base pair insertion or deletion (termed a frameshift mutation) may result in two different proteins being coded for by the same DNA segment. To insure against this, the triplet codons corresponding to the desired polypeptide must be aligned in multiples of three from the initiation codon, i.e. the correct "reading frame" being maintained.

"Recombinant DNA cloning vector" as used herein refers to any autonomously replicating agent, including, but not limited to, plasmids and phages, comprising a DNA molecule to which one or more additional DNA segments can or have been added.

The term "recombinant DNA expression vector" as used herein refers to any recombinant DNA cloning vector in which a promoter to control transcription of the inserted DNA has been incorporated.

The term "expression vector system" as used herein refers to a recombinant DNA expression vector in combination with one or more trans-acting factors that specifically influence transcription, stability, or replication of the recombinant DNA expression vector. The trans-acting factor may be expressed from a co-transfected plasmid, virus, or other extrachromosomal element, or may be expressed from a gene integrated within the chromosome.

"Transcription" as used herein refers to the process whereby information contained in a nucleotide sequence of DNA is transferred to a complementary RNA sequence.

The term "transfection" as used herein refers to the taking up of an expression vector by a host cell whether or not any coding sequences are in fact expressed. Numerous methods of transfection are known to the ordinarily skilled artisan, for example, calcium phosphate co-precipitation, and electroporation. Successful transfection is generally recognized when any indication of the operation of this vector occurs within the host cell.

The term "transformation" as used herein means the introduction of DNA into an organism so that the DNA is replicable, either as an extrachromosomal element or by chromosomal integration. Methods of transforming bacterial and eukaryotic hosts are well known in the art, many of which methods, such as nuclear injection, protoplast fusion or by calcium treatment using calcium chloride are summarized in J. Sambrook, et al., MOLECULAR CLONING: A LABORATORY MANUAL, (1989).

The term "translation" as used herein refers to the process whereby the genetic information of messenger RNA is used to specify and direct the synthesis of a polypeptide chain.

The term "vector" as used herein refers to a nucleic acid compound used for the transformation of cells in gene manipulation bearing polynucleotide sequences corresponding to appropriate protein molecules which when combined with appropriate control sequences confer specific properties on the host cell to be transformed. Plasmids, viruses, and bacteriophage are suitable vectors. Artificial vectors are constructed by cutting and joining DNA molecules from different sources using restriction enzymes and ligases. The term "vector" as used herein includes Recombinant DNA cloning vectors and Recombinant DNA expression vectors.

The terms "complementary" or "complementarity" as used herein refers to pair of bases, purines and pyrimidines, that associate through hydrogen bonding in double stranded nucleic acid. The following base pairs are complementary: guanine and cytosine; adenine and thymine; and adenine and uracil.

The term "hybridization" as used herein refers to a process in which a strand of nucleic acid joins with a complementary strand through base pairing. The conditions employed in the hybridization of two non-identical, but very similar, complementary nucleic acids varies with the degree of complementarity of the two strands and the length of the strands. Such techniques and conditions are well known to practitioners in this field.

"Isolated amino acid sequence" refers to any amino acid sequence, however constructed or synthesized, which is locationally distinct from the naturally occurring sequence.

"Isolated DNA compound" refers to any DNA sequence, however constructed or synthesized, which is locationally distinct from its natural location in genomic DNA.

"Isolated nucleic acid compound" refers to any RNA or DNA sequence, however constructed or synthesized, which is locationally distinct from its natural location.

A "primer" is a nucleic acid fragment which functions as an initiating substrate for enzymatic or synthetic elongation.

The term "promoter" refers to a DNA sequence which directs transcription of DNA to RNA.

A "probe" as used herein is a nucleic acid compound or a fragment thereof which hybridizes with a nucleic acid compound which encodes either the entire sequence SEQ ID NO:2, a sequence complementary to SEQ ID NO:2, or a part thereof.

The term "stringency" refers to a set of hybridization conditions which may be varied in order to vary the degree of nucleic acid affinity for other nucleic acid. (See the definition of "hybridization", supra.)

The term "antigenically distinct" as used herein refers to a situation in which antibodies raised against an epitope of the proteins of the present invention, or a fragment thereof, may be used to differentiate between the proteins of the present invention and other neuropeptide Y receptor subtypes. This term may also be employed in the sense that such antibodies may be used to differentiate between the human PP-fold receptor protein and analogous proteins derived from other species.

The term "PCR" as used herein refers to the widely-known polymerase chain reaction employing a thermally-stable polymerase.

"Immunoreactive Protein(s)" collectively describes antibodies, fragments of antibodies capable of binding antigens of a similar nature as the parent antibody molecule from which they are derived, and single chain polypeptide binding molecules as described in Patent Cooperation Treaty Application PCT/US 87/02208, International Publication No. WO 88/01649.

The phrase "reading frame" as used herein refers to the nucleotide sequence from which translation occurs "read" in triplets by the translational apparatus of tRNA, ribosomes and associated factors, each triplet corresponding to a particular amino acid. Because each triplet is distinct and of the same length, the coding sequence must be a multiple of three. A base pair insertion or deletion (termed a frameshift mutation) may result in two different proteins being coded for by the same DNA segment. To insure against this, the triplet codons corresponding to the desired polypeptide must be aligned in multiples of three from the initiation codon, i.e. the correct "reading frame" must be maintained. In the creation of fusion proteins containing a chelating peptide, the reading frame of the DNA sequence encoding the structural protein must be maintained in the DNA sequence encoding the chelating peptide.

The term "treating" describes the management and care of a patient for the purpose of combating the disease, condition, or disorder and includes the administration of a compound of present invention to prevent the onset of the symptoms or complications, alleviating the symptoms or complications, or eliminating the disease, condition, or disorder. Treating obesity, for example, includes the inhibition of food intake, the inhibition of weight gain, and inducing weight loss in patients in need thereof.

As used herein, the term "$C_1$–$C_{10}$ alkyl" refers to straight or branched, monovalent, saturated aliphatic chains of 1 to 10 carbon atoms and includes, but is not limited to, methyl, ethyl, propyl, isopropyl, butyl, isobutyl, t-butyl, pentyl, isopentyl, and hexyl. The term "$C_1$–$C_{10}$ alkyl" includes within its definition the terms "$C_1$–$C_4$ alkyl" and "$C_1$–$C_6$ alkyl".

"$C_1$–$C_6$ alkoxy" represents a straight or branched alkyl chain having from one to six carbon atoms attached to an oxygen atom. Typical $C_1$–$C_6$ alkoxy groups include methoxy, ethoxy, propoxy, isopropoxy, butoxy, t-butoxy, pentoxy and the like. The term "$C_1$–$C_6$ alkoxy" includes within its definition the term "$C_1$–$C_4$ alkoxy".

"$C_1$–$C_6$ alkylidenyl" refers to a straight or branched, divalent, saturated aliphatic chains of 1 to 6 carbon atoms and includes, but is not limited to, methylenyl, ethylenyl, propylenyl, isopropylenyl, butylenyl, isobutylenyl, t-butylenyl, pentylenyl, isopentylenyl, hexylenyl, and the like. The term "$C_1$–$C_4$ alkylidenyl" is encompassed within the term "$C_1$–$C_6$ alkylidenyl".

The term "halo" encompasses chloro, fluoro, bromo and iodo.

The term "leaving group" as used herein refers to a group of atoms that is displaced from a carbon atom by the attack of a nucleophile in a nucleophilic substitution reaction. The term "leaving group" as used in this document encompasses, but is not limited to, activating groups.

The term "activating group" as used herein refers a leaving group which, when taken with the carbonyl (—C=O) group to which it is attached, is more likely to take part in an acylation reaction than would be the case if the group were not present, as in the free acid. Such activating groups are well-known to those skilled in the art and may be, for example, succinimidoxy, phthalimidoxy, benzotriazolyloxy, benzenesulfonyloxy, methanesulfonyloxy, toluenesulfonyloxy, azido, or —O—CO—($C_4$–$C_7$ alkyl).

Obesity protein—refers to the protein produced from the obesity gene following transcription and deletions of introns, translation to a protein and processing to the mature protein with secretory signal peptide removed, e.g., from the N-terminal valine-proline to the C-terminal cysteine of the mature protein. The mouse obesity protein and human obesity protein is published in Zhang et al. *Nature* 372: 425–32 (1994). The rat obesity protein is published in Murakami et al., *Biochemical and Biophysical Research Comm.* 209(3): 944–52 (1995). In the human, murine and rat obesity protein the Cys associated with di-sulfide formation is positions 96 and 145. However, particularly with the murine and human obesity protein, a desGln(28) variant has been observed. Hense, the Cys residues associated with di-sulfide bond formation may be at positions 95 or 96 and at position 145 or 146. Obesity protein may also be referred to throughout this specification as OB or ob gene product. The term "leptin" has also been employed to describe an obesity protein, particularly the naturally occurring human obesity protein.

The term "treating" describes the management and care of a patient for the purpose of combating the disease, condition, or disorder and includes the administration of a compound of present invention to prevent the onset of the symptoms or complications, alleviating the symptoms or complications, or eliminating the disease, condition, or disorder. Treating obesity, for example, includes the inhibition of food intake, the inhibition of weight gain, and inducing weight loss in patients in need thereof.

Preferably, the claimed proteins are those of Formula (II):

```
Val Pro Ile Gln Lys Val Gln Asp Asp Thr Lys Thr Leu Ile Lys Thr   SEQ ID NO:2
1               5                   10                  15

Ile Val Thr Arg Ile Asn Asp Ile Ser His Xaa Gln Ser Val Ser Ser
            20                  25                  30

Lys Gln Lys Val Thr Gly Leu Asp Phe Ile Pro Gly Leu His Pro Ile
            35                  40                  45
```

-continued

```
Leu Thr Leu Ser Lys Met Asp Gln Thr Leu Ala Val Tyr Gln Cln Ile
 50              55                  60

Leu Thr Ser Met Pro Ser Arg Asn Val Ile Cln Ile Xaa Asn Asp Leu
 65              70                  75                  80

Glu Asn Leu Arg Asp Leu Leu His Val Leu Ala Phe Ser Lys Ser Cys
             85                  90                  95

His Leu Pro Trp Ala Ser Gly Leu Clu Thr Leu Asp Ser Leu Gly Gly
            100                 105             110

Val Leu Glu Ala Ser Xaa Tyr Ser Thr Glu Val Val Ala Leu Ser Arg
        115             120                 125

Leu Gln Gly Ser Leu Gln Asp Met Leu Trp Gln Leu Asp Leu Ser Pro
        130             135             140

145
Gly Cys
``` wherein:

Xaa at position 27 is Thr or Ala;
Xaa at position 77 is Ser or Ala;
Xaa at position 118 is Gly or Leu;

said protein having at least one substitution, preferably having one to five substitutions and, most preferably, one or two substitutions selected from the group consisting of:

His at position 97 is replaced with Gln, Asn, Ala, Gly, Ser or Pro;
Trp at position 100 is replaced with Ala, Glu, Asp, Asn, Met, Ile, Phe, Tyr, Ser, Thr, Gly, Gln or Leu;
Ala at position 101 is replaced with Ser, Asn, Gly, His, Pro, Thr or Val;
Glu at position 105 is replaced with Gin;
Thr at position 106 is replaced with Lys;
Leu at position 107 is replaced with Pro;
Asp at position 108 is replaced with Glu; or
Gly at position 111 is replaced with Asp.

Most preferably, the claimed proteins have one substitution wherein:

Trp at position 100 is replaced with Ala, Glu, Asp, Asn, Met, Ile, Phe, Tyr, Ser, Thr, Gly, Gln or Leu; or Examples of preferred proteins of the present invention include proteins of SEQ ID NO:2, wherein Xaa at position 27 is Thr; Xaa at position 77 is Ser; Xaa at position 118 is Gly; and the amino acid residues at positions 97, 100, 101, 105, 106, 107, 108, and 111 are as follows in Table 1:

TABLE 1

| Compound | Amino Acid Position | | | | | | | |
|---|---|---|---|---|---|---|---|---|
| | 97 | 100 | 101 | 105 | 106 | 107 | 108 | 111 |
| 1 | Ser | Trp | Ala | Glu | Thr | Leu | Asp | Gly |
| 2 | His | Gln | Ala | Glu | Thr | Leu | Asp | Gly |
| 3 | His | Trp | Thr | Glu | Thr | Leu | Asp | Gly |
| 4 | His | Trp | Ala | Gln | Thr | Leu | Asp | Gly |
| 5 | His | Trp | Ala | Glu | Lys | Leu | Asp | Gly |
| 6 | His | Trp | Ala | Glu | Thr | Pro | Asp | Gly |

TABLE 1-continued

| Compound | Amino Acid Position | | | | | | | |
|---|---|---|---|---|---|---|---|---|
| | 97 | 100 | 101 | 105 | 106 | 107 | 108 | 111 |
| 7 | His | Trp | Ala | Glu | Thr | Leu | Glu | Gly |
| 8 | His | Trp | Ala | Glu | Thr | Leu | Asp | Asp |
| 9 | Ser | Gln | Ala | Glu | Thr | Leu | Asp | Gly |
| 10 | Ser | Trp | Thr | Glu | Thr | Leu | Asp | Gly |
| 11 | Ser | Trp | Ala | Gln | Thr | Leu | Asp | Gly |
| 12 | Ser | Trp | Ala | Glu | Lys | Leu | Asp | Gly |
| 13 | Ser | Trp | Ala | Glu | Thr | Pro | Asp | Gly |
| 14 | Ser | Trp | Ala | Glu | Thr | Leu | Glu | Gly |
| 15 | Ser | Trp | Ala | Glu | Thr | Leu | Asp | Asp |
| 16 | His | Gln | Thr | Glu | Thr | Leu | Asp | Gly |
| 17 | His | Gln | Ala | Gln | Thr | Leu | Asp | Gly |
| 18 | His | Gln | Ala | Glu | Lys | Leu | Asp | Gly |
| 19 | His | Gln | Ala | Glu | Thr | Pro | Asp | Gly |
| 20 | His | Gln | Ala | Glu | Thr | Leu | Glu | Gly |
| 21 | His | Gln | Ala | Glu | Thr | Leu | Asp | Asp |
| 22 | His | Trp | Thr | Gln | Thr | Leu | Asp | Gly |
| 23 | His | Trp | Thr | Glu | Lys | Leu | Asp | Gly |
| 24 | His | Trp | Thr | Glu | Thr | Pro | Asp | Gly |
| 25 | His | Trp | Thr | Glu | Thr | Leu | Glu | Gly |
| 26 | His | Trp | Thr | Glu | Thr | Leu | Asp | Asp |
| 27 | His | Trp | Ala | Gln | Lys | Leu | Asp | Gly |
| 28 | His | Trp | Ala | Gln | Thr | Pro | Asp | Gly |
| 29 | His | Trp | Ala | Gln | Thr | Leu | Glu | Gly |
| 30 | His | Trp | Ala | Gln | Thr | Leu | Asp | Asp |
| 31 | His | Trp | Ala | Glu | Lys | Pro | Asp | Gly |

TABLE 1-continued

| Compound | Amino Acid Position | | | | | | | |
|---|---|---|---|---|---|---|---|---|
| | 97 | 100 | 101 | 105 | 106 | 107 | 108 | 111 |
| 32 | His | Trp | Ala | Glu | Lys | Leu | Glu | Gly |
| 33 | His | Trp | Ala | Glu | Lys | Leu | Asp | Asp |
| 34 | His | Trp | Ala | Glu | Thr | Pro | Glu | Gly |
| 35 | His | Trp | Ala | Glu | Thr | Pro | Asp | Asp |
| 36 | His | Trp | Ala | Glu | Thr | Leu | Glu | Asp |
| 37 | Ser | Gln | Thr | Glu | Thr | Leu | Asp | Gly |
| 38 | Ser | Gln | Ala | Gln | Thr | Leu | Asp | Gly |
| 39 | Ser | Gln | Ala | Glu | Lys | Leu | Asp | Gly |
| 40 | Ser | Gln | Ala | Glu | Thr | Pro | Asp | Gly |
| 41 | Ser | Gln | Ala | Glu | Thr | Leu | Glu | Gly |
| 42 | Ser | Gln | Ala | Glu | Thr | Leu | Asp | Asp |
| 43 | Ser | Trp | Thr | Gln | Thr | Leu | Asp | Gly |
| 44 | Ser | Trp | Thr | Glu | Lys | Leu | Asp | Gly |
| 45 | Ser | Trp | Thr | G1U | Thr | Pro | Asp | Gly |
| 46 | Ser | Trp | Thr | Glu | Thr | Leu | Glu | Gly |
| 47 | Ser | Trp | Thr | Glu | Thr | Leu | Asp | Asp |
| 48 | Ser | Trp | Ala | Gln | Lys | Leu | Asp | Gly |
| 49 | Ser | Trp | Ala | Gln | Thr | Pro | Asp | Gly |
| 50 | Ser | Trp | Ala | Gln | Thr | Leu | Glu | Gly |
| 51 | Ser | Trp | Ala | Gln | Thr | Leu | Asp | Asp |
| 52 | Ser | Trp | Ala | Glu | Lys | Pro | Asp | Gly |
| 53 | Ser | Trp | Ala | Glu | Lys | Leu | Glu | Gly |
| 54 | Ser | Trp | Ala | Glu | Lys | Leu | Asp | Asp |
| 55 | Ser | Trp | Ala | Glu | Thr | Pro | Glu | Gly |
| 56 | Ser | Trp | Ala | Glu | Thr | Pro | Asp | Asp |
| 57 | Ser | Trp | Ala | Glu | Thr | Leu | Glu | Asp |
| 58 | His | Gln | Thr | Gln | Thr | Leu | Asp | Gly |
| 59 | His | Gln | Thr | Glu | Lys | Leu | Asp | Gly |
| 60 | His | Gln | Thr | Glu | Thr | Pro | Asp | Gly |
| 61 | His | Gln | Thr | Glu | Thr | Leu | Glu | Gly |
| 62 | His | Gln | Thr | Glu | Thr | Leu | Asp | Asp |
| 63 | His | Gln | Ala | Gln | Lys | Leu | Asp | Gly |
| 64 | His | Gln | Ala | Gln | Thr | Pro | Asp | Gly |
| 65 | His | Gln | Ala | Gln | Thr | Leu | Glu | Gly |
| 66 | His | Gln | Ala | Gln | Thr | Leu | Asp | Asp |
| 67 | His | Gln | Ala | Glu | Lys | Pro | Asp | Gly |
| 68 | His | Gln | Ala | Glu | Lys | Leu | Glu | Gly |
| 69 | His | Gln | Ala | Glu | Lys | Leu | Asp | Asp |
| 70 | His | Gln | Ala | Glu | Thr | Pro | Glu | Gly |
| 71 | His | Gln | Ala | Glu | Thr | Pro | Asp | Asp |
| 72 | His | Gln | Ala | Glu | Thr | Leu | Glu | Asp |
| 73 | His | Trp | Thr | Gln | Lys | Leu | Asp | Gly |
| 74 | His | Trp | Thr | Gln | Thr | Pro | Asp | Gly |
| 75 | His | Trp | Thr | Gln | Thr | Leu | Glu | Gly |
| 76 | His | Trp | Thr | Gln | Thr | Leu | Asp | Asp |
| 77 | His | Trp | Thr | Glu | Lys | Pro | Asp | Gly |
| 78 | His | Trp | Thr | Glu | Lys | Leu | Glu | Gly |
| 79 | His | Trp | Thr | Glu | Lys | Leu | Asp | Asp |
| 80 | His | Trp | Thr | Glu | Thr | Pro | Glu | Gly |
| 81 | His | Trp | Thr | Glu | Thr | Pro | Asp | Asp |
| 82 | His | Trp | Thr | Glu | Thr | Leu | Glu | Asp |
| 83 | His | Trp | Ala | Gln | Lys | Pro | Asp | Gly |
| 84 | His | Trp | Ala | Gln | Lys | Leu | Glu | Gly |
| 85 | His | Trp | Ala | Gln | Lys | Leu | Asp | Asp |
| 86 | His | Trp | Ala | Gln | Thr | Pro | Glu | Gly |
| 87 | His | Trp | Ala | Gln | Thr | Pro | Asp | Asp |
| 88 | His | Trp | Ala | Gln | Thr | Leu | Glu | Asp |
| 89 | His | Trp | Ala | Glu | Lys | Pro | Glu | Gly |
| 90 | His | Trp | Ala | Glu | Lys | Pro | Asp | Asp |
| 91 | His | Trp | Ala | Glu | Lys | Leu | Glu | Asp |
| 92 | His | Trp | Ala | Glu | Thr | Pro | Glu | Asp |
| 93 | Ser | Gln | Thr | Gln | Thr | Leu | Asp | Gly |
| 94 | Ser | Gln | Thr | Glu | Lys | Leu | Asp | Gly |
| 95 | Ser | Gln | Thr | Glu | Thr | Pro | Asp | Gly |
| 96 | Ser | Gln | Thr | Glu | Thr | Leu | Glu | Gly |
| 97 | Ser | Gln | Thr | Glu | Thr | Leu | Asp | Asp |
| 98 | Ser | Gln | Ala | Gln | Lys | Leu | Asp | Gly |
| 99 | Ser | Gln | Ala | Gln | Thr | Pro | Asp | Gly |
| 100 | Ser | Gln | Ala | Gln | Thr | Leu | Glu | Gly |
| 101 | Ser | Gln | Ala | Gln | Thr | Leu | Asp | Asp |
| 102 | Ser | Gln | Ala | Glu | Lys | Pro | Asp | Gly |
| 103 | Ser | Gln | Ala | Glu | Lys | Leu | Glu | Gly |
| 104 | Ser | Gln | Ala | Glu | Lys | Leu | Asp | Asp |
| 105 | Ser | Gln | Ala | Glu | Thr | Pro | Glu | Gly |
| 106 | Ser | Gln | Ala | Glu | Thr | Pro | Asp | Asp |
| 107 | Ser | Gln | Ala | Glu | Thr | Leu | Glu | Asp |

TABLE 1-continued

| Compound | \multicolumn{8}{c}{Amino Acid Position} |
|---|---|---|---|---|---|---|---|---|
| | 97 | 100 | 101 | 105 | 106 | 107 | 108 | 111 |
| 108 | Ser | Trp | Thr | Gln | Lys | Leu | Asp | Gly |
| 109 | Ser | Trp | Thr | Gln | Thr | Pro | Asp | Gly |
| 110 | Ser | Trp | Thr | Gln | Thr | Leu | Glu | Gly |
| 111 | Ser | Trp | Thr | Gln | Thr | Leu | Asp | Asp |
| 112 | Ser | Trp | Thr | Glu | Lys | Pro | Asp | Gly |
| 113 | Ser | Trp | Thr | Glu | Lys | Leu | Glu | Gly |
| 114 | Ser | Trp | Thr | Glu | Lys | Leu | Asp | Asp |
| 115 | Ser | Trp | Thr | Glu | Thr | Pro | Glu | Gly |
| 116 | Ser | Trp | Thr | Glu | Thr | Pro | Asp | Asp |
| 117 | Ser | Trp | Thr | Glu | Thr | Leu | Glu | Asp |
| 118 | Ser | Trp | Ala | Gln | Lys | Pro | Asp | Gly |
| 119 | Ser | Trp | Ala | Gln | Lys | Leu | Glu | Gly |
| 120 | Ser | Trp | Ala | Gln | Lys | Leu | Asp | Asp |
| 121 | Ser | Trp | Ala | Gln | Thr | Pro | Glu | Gly |
| 122 | Ser | Trp | Ala | Gln | Thr | Pro | Asp | Asp |
| 123 | Ser | Trp | Ala | Gln | Thr | Leu | Glu | Asp |
| 124 | Ser | Trp | Ala | Glu | Lys | Pro | Glu | Gly |
| 125 | Ser | Trp | Ala | Glu | Lys | Pro | Asp | Asp |
| 126 | Ser | Trp | Ala | Glu | Lys | Leu | Glu | Asp |
| 127 | Ser | Trp | Ala | Glu | Thr | Pro | Glu | Asp |
| 128 | His | Gln | Thr | Gln | Lys | Leu | Asp | Gly |
| 129 | His | Gln | Thr | Gln | Thr | Pro | Asp | Gly |
| 130 | His | Gln | Thr | Gln | Thr | Leu | Glu | Gly |
| 131 | His | Gln | Thr | Gln | Thr | Leu | Asp | Asp |
| 132 | His | Gln | Thr | Glu | Lys | Pro | Asp | Gly |
| 133 | His | Gln | Thr | Glu | Lys | Leu | Glu | Gly |
| 134 | His | Gln | Thr | Glu | Lys | Leu | Asp | Asp |
| 135 | His | Gln | Thr | Glu | Thr | Pro | Glu | Gly |
| 136 | His | Gln | Thr | Glu | Thr | Pro | Asp | Asp |
| 137 | His | Gln | Thr | Glu | Thr | Leu | Glu | Asp |
| 138 | His | Gln | Ala | Gln | Lys | Pro | Asp | Gly |
| 139 | His | Gln | Ala | Gln | Lys | Leu | Glu | Gly |
| 140 | His | Gln | Ala | Gln | Lys | Leu | Asp | Asp |
| 141 | His | Gln | Ala | Gln | Thr | Pro | Glu | Gly |
| 142 | His | Gln | Ala | Gln | Thr | Pro | Asp | Asp |
| 143 | His | Gln | Ala | Gln | Thr | Leu | Glu | Asp |
| 144 | His | Gln | Ala | Glu | Lys | Pro | Glu | Gly |
| 145 | His | Gln | Ala | Glu | Lys | Pro | Asp | Asp |
| 146 | His | Gln | Ala | Glu | Lys | Leu | Glu | Asp |
| 147 | His | Gln | Ala | Glu | Thr | Pro | Glu | Asp |
| 148 | His | Trp | Thr | Gln | Lys | Pro | Asp | Gly |
| 149 | His | Trp | Thr | Gln | Lys | Leu | Glu | Gly |
| 150 | His | Trp | Thr | Gln | Lys | Leu | Asp | Asp |
| 151 | His | Trp | Thr | Gln | Thr | Pro | Glu | Gly |
| 152 | His | Trp | Thr | Gln | Thr | Pro | Asp | Asp |
| 153 | His | Trp | Thr | Gln | Thr | Leu | Glu | Asp |
| 154 | His | Trp | Thr | Glu | Lys | Pro | Glu | Gly |
| 155 | His | Trp | Thr | Glu | Lys | Pro | Asp | Asp |
| 156 | His | Trp | Thr | Glu | Lys | Leu | Glu | Asp |
| 157 | His | Trp | Thr | Glu | Thr | Pro | Glu | Asp |
| 158 | His | Trp | Ala | Gln | Lys | Pro | Glu | Gly |
| 159 | His | Trp | Ala | Gln | Lys | Pro | Asp | Asp |
| 160 | His | Trp | Ala | Gln | Lys | Leu | Glu | Asp |
| 161 | His | Trp | Ala | Gln | Thr | Pro | Glu | Asp |
| 162 | His | Trp | Ala | Glu | Lys | Pro | Glu | Asp |
| 163 | His | Trp | Ala | Glu | Lys | Pro | Glu | Asp |
| 164 | His | Trp | Thr | Glu | Lys | Pro | Glu | Asp |
| 165 | His | Trp | Thr | Gln | Thr | Pro | Glu | Asp |
| 166 | His | Trp | Thr | Gln | Lys | Leu | Glu | Asp |
| 167 | His | Trp | Thr | Gln | Lys | Pro | Asp | Asp |
| 168 | His | Trp | Thr | Gln | Lys | Pro | Glu | Gly |
| 169 | His | Gln | Ala | Glu | Lys | Pro | Glu | Asp |
| 170 | His | Gln | Ala | Gln | Thr | Pro | Glu | Asp |
| 171 | His | Gln | Ala | Gln | Lys | Leu | Glu | Asp |
| 172 | His | Gln | Ala | Gln | Lys | Pro | Asp | Asp |
| 173 | His | Gln | Ala | Gln | Lys | Pro | Glu | Gly |
| 174 | His | Gln | Thr | Glu | Thr | Pro | Glu | Asp |
| 175 | His | Gln | Thr | Glu | Lys | Leu | Glu | Asp |
| 176 | His | Gln | Thr | Glu | Lys | Pro | Asp | Asp |
| 177 | His | Gln | Thr | Glu | Lys | Pro | Glu | Gly |
| 178 | His | Gln | Thr | Gln | Thr | Leu | Glu | Asp |
| 179 | His | Gln | Thr | Gln | Thr | Pro | Asp | Asp |
| 180 | His | Gln | Thr | Gln | Thr | Pro | Glu | Gly |
| 181 | His | Gln | Thr | Gln | Lys | Leu | Asp | Asp |
| 182 | His | Gln | Thr | Gln | Lys | Leu | Glu | Gly |
| 183 | His | Gln | Thr | Gln | Lys | Pro | Asp | Gly |

TABLE 1-continued

| Compound | \multicolumn{8}{c|}{Amino Acid Position} |
| | 97 | 100 | 101 | 105 | 106 | 107 | 108 | 111 |
|---|---|---|---|---|---|---|---|---|
| 184 | Ser | Trp | Ala | Glu | Lys | Pro | Glu | Asp |
| 185 | Ser | Trp | Ala | Gln | Thr | Pro | Glu | Asp |
| 186 | Ser | Trp | Ala | Gln | Lys | Leu | Glu | Asp |
| 187 | Ser | Trp | Ala | Gln | Lys | Pro | Asp | Asp |
| 188 | Ser | Trp | Ala | Gln | Lys | Pro | Glu | Gly |
| 189 | Ser | Trp | Thr | Glu | Thr | Pro | Glu | Asp |
| 190 | Ser | Trp | Thr | Glu | Lys | Leu | Glu | Asp |
| 191 | Ser | Trp | Thr | Glu | Lys | Pro | Asp | Asp |
| 192 | Ser | Trp | Thr | Glu | Lys | Pro | Glu | Gly |
| 193 | Ser | Trp | Thr | Gln | Thr | Leu | Glu | Asp |
| 194 | Ser | Trp | Thr | Gln | Thr | Pro | Asp | Asp |
| 195 | Ser | Trp | Thr | Gln | Thr | Pro | Glu | Gly |
| 196 | Ser | Trp | Thr | Gln | Lys | Leu | Asp | Asp |
| 197 | Ser | Trp | Thr | Gln | Lys | Leu | Glu | Gly |
| 198 | Ser | Trp | Thr | Gln | Lys | Pro | Asp | Gly |
| 199 | Ser | Gln | Ala | Glu | Thr | Pro | Glu | Asp |
| 200 | Ser | Gln | Ala | Glu | Lys | Leu | Glu | Asp |
| 201 | Ser | Gln | Ala | Glu | Lys | Pro | Asp | Asp |
| 202 | Ser | Gln | Ala | Glu | Lys | Pro | Glu | Gly |
| 203 | Ser | Gln | Ala | Gln | Thr | Leu | Glu | Asp |
| 204 | Ser | Gln | Ala | Gln | Thr | Pro | Asp | Asp |
| 205 | Ser | Gln | Ala | Gln | Thr | Pro | G1U | Gly |
| 206 | Ser | Gln | Ala | Gln | Lys | Leu | Asp | Asp |
| 207 | Ser | Gln | Ala | Gln | Lys | Leu | Glu | Gly |
| 208 | Ser | Gln | Ala | Gln | Lys | Pro | Asp | Gly |
| 209 | Ser | Gln | Thr | Glu | Thr | Leu | Glu | Asp |
| 210 | Ser | Gln | Thr | Glu | Thr | Pro | Asp | Asp |
| 211 | Ser | Gln | Thr | Glu | Thr | Pro | Glu | Gly |
| 212 | Ser | Gln | Thr | Glu | Lys | Leu | Asp | Asp |
| 213 | Ser | Gln | Thr | Glu | Lys | Leu | Glu | Gly |
| 214 | Ser | Gln | Thr | Glu | Lys | Pro | Asp | Gly |
| 215 | Ser | Gln | Thr | Gln | Thr | Leu | Asp | Asp |
| 216 | Ser | Gln | Thr | Gln | Thr | Leu | Glu | Gly |
| 217 | Ser | Gln | Thr | Gln | Thr | Pro | Asp | Gly |
| 218 | Ser | Gln | Thr | Gln | Lys | Leu | Asp | Gly |
| 219 | His | Trp | Thr | Gln | Lys | Pro | Glu | Asp |
| 220 | His | Gln | Ala | Gln | Lys | Pro | Glu | Asp |
| 221 | His | Gln | Thr | Glu | Lys | Pro | Glu | Asp |
| 222 | His | Gln | Thr | Gln | Thr | Pro | Glu | Asp |
| 223 | His | Gln | Thr | Gln | Lys | Leu | Glu | Asp |
| 224 | His | Gln | Thr | Gln | Lys | Pro | Asp | Asp |
| 225 | His | Gln | Thr | Gln | Lys | Pro | Glu | Gly |
| 226 | Ser | Trp | Ala | Gln | Lys | Pro | Glu | Asp |
| 227 | Ser | Trp | Thr | Glu | Lys | Pro | Glu | Asp |
| 228 | Ser | Trp | Thr | Gln | Thr | Pro | Glu | Asp |
| 229 | Ser | Trp | Thr | Gln | Lys | Leu | Glu | Asp |
| 230 | Ser | Trp | Thr | Gln | Lys | Pro | Asp | Asp |
| 231 | Ser | Trp | Thr | Gln | Lys | Pro | Glu | Gly |
| 232 | Ser | Gln | Ala | Glu | Lys | Pro | Glu | Asp |
| 233 | Ser | Gln | Ala | Gln | Thr | Pro | Glu | Asp |
| 234 | Ser | Gln | Ala | Gln | Lys | Leu | Glu | Asp |
| 235 | Ser | Gln | Ala | Gln | Lys | Pro | Asp | Asp |
| 236 | Ser | Gln | Ala | Gln | Lys | Pro | Glu | Gly |
| 237 | Ser | Gln | Thr | Glu | Thr | Pro | Glu | Asp |
| 238 | Ser | Gln | Thr | Glu | Lys | Leu | Glu | Asp |
| 239 | Ser | Gln | Thr | Glu | Lys | Pro | Asp | Asp |
| 240 | Ser | Gln | Thr | Glu | Lys | Pro | Glu | Gly |
| 241 | Ser | Gln | Thr | Gln | Thr | Leu | Glu | Asp |
| 242 | Ser | Gln | Thr | Gln | Thr | Pro | Asp | Asp |
| 243 | Ser | Gln | Thr | Gln | Thr | Pro | Glu | Gly |
| 244 | Ser | Gln | Thr | Gln | Lys | Leu | Asp | Asp |
| 245 | Ser | Gln | Thr | Gln | Lys | Leu | Glu | Gly |
| 246 | Ser | Gln | Thr | Gln | Lys | Pro | Asp | Gly |
| 247 | His | Gln | Thr | Gln | Lys | Pro | Glu | Asp |
| 248 | Ser | Trp | Thr | Gln | Lys | Pro | Glu | Asp |
| 249 | Ser | Gln | Ala | Gln | Lys | Pro | Glu | Asp |
| 250 | Ser | Gln | Thr | Glu | Lys | Pro | Glu | Asp |
| 251 | Ser | Gln | Thr | Gln | Thr | Pro | Glu | Asp |
| 252 | Ser | Gln | Thr | Gln | Lys | Leu | Glu | Asp |
| 253 | Ser | Gln | Thr | Gln | Lys | Pro | Asp | Asp |
| 254 | Ser | Gln | Thr | Gln | Lys | Pro | Glu | Gly |
| 255 | Ser | Gln | Thr | Gln | Lys | Pro | Glu | Asp |
| 256 | His | Ala | Ala | Glu | Thr | Leu | Asp | Gly |
| 257 | His | Leu | Ala | Glu | Thr | Leu | Asp | Gly |
| 258 | Pro | Trp | Ala | Glu | Thr | Leu | Asp | Gly |

Other preferred proteins are those wherein Xaa at position 27 is Ala; Xaa at position 77 is Ser; Xaa at position 118 is Gly; and the amino residues at positions 97, 100, 101, 105, 106, 107, 108 and 111 are as described in Table I.

The present invention provides biologically active proteins that provide effective treatment for obesity. Unexpectedly, the claimed proteins have improved properties due to specific substitutions to the human obesity protein. The claimed proteins are more stable than both the mouse and human obesity protein and, therefore, are superior therapeutic agents.

The claimed proteins ordinarily are prepared by recombinant techniques. Techniques for making substitutional mutations at predetermined sites in DNA having a known sequence are well known, for example M13 primer mutagenesis. The mutations that might be made in the DNA encoding the present anti-obesity proteins must not place the sequence out of reading frame and preferably will not create complementary regions that could produce secondary mRNA structure. See, DeBoer, et al., European Patent Publication, 075,444 A (1983).

The compounds of the present invention may be produced either by recombinant DNA technology or well known chemical procedures, such as solution or solid-phase peptide synthesis, or semi-synthesis in solution beginning with protein fragments coupled through conventional solution methods.

In addition to the above identified protein sequences, it is frequently considered expeditious to prepare an obesity protein with a one or two amino acid leader sequence, especially with a methionine containing leader. Two frequently employed leaders are Met-Arg and Met-Asp. Such proteins may be identified infra as Met-Arg-OB or Met-Asp-OB or may be identified by Met-Arg-SEQ ID NO:X, where x is 1 to 4.

Traditional compounds useful in treating conditions associated with an excess of neuropeptide Y act by binding to receptors specific for neuropeptide Y as well as the closely related neuropeptides. [For a review of neuropeptide Y receptors, see, D. Gehlert, *Life Sciences*, 55:551–562 (1994)]. Traditional receptors for neuropeptide Y and peptide YY have considerable overlap while pancreatic polypeptide appears to have its own distinct set of receptors. Many, but not all, of the effects of neuropeptide Y can be replicated using peptide YY.

Two subtypes of receptors for neuropeptide Y were initially proposed on the basis of the affinity of the 13–36 fragment of neuropeptide Y using a preparation of the sympathetic nervous system. While these are the best established receptors for neuropeptide Y, a substantial body of evidence exists that there are additional receptor subtypes. The best established is a Y-3 receptor that is responsive to neuropeptide Y, but not to peptide YY. Another recently delineated receptor has been described that binds peptide YY with high affinity and neuropeptide Y with lower affinity. While the pharmacology of the feeding response to neuropeptide Y appears to be Y-1 in nature, a separate "feeding receptor" has been proposed. Until this invention, the Y-1 receptor was the only one that had been successfully cloned to date. The following paragraphs summarize the available information on the known neuropeptide Y receptor subtypes and their potential role in physiological function.

Y-1 Receptor

The Y-1 receptor is the best characterized receptor for neuropeptide Y. This receptor is generally considered to be postsynaptic and mediates many of the known actions of neuropeptide Y in the periphery. Originally, this receptor was described as having poor affinity for C-terminal fragments of neuropeptide Y, such as the 13–36 fragment, but interacts with the full length neuropeptide Y and peptide YY with equal affinity. L. Selbie, et al., Patent Cooperation Treaty publication WO 93/09227, published May 13, 1993; C. Wahlestedt, et al., *Regulatory Peptides*, 13:307–318 (1986); C. Wahlestedt, et al., NEURONAL MESSENGERS IN VASCULAR FUNCTION, 231–241 (Nobin, et al., eds. 1987). Substitution of the amino acid at position 34 with a proline ($Pro^{34}$) results in a protein which is specific for the Y-1 receptor. E. K. Potter, et al., *European Journal of Pharmacology*, 193:15–19 (1991). This tool has been used to establish a role for the Y-1 receptor in a variety of functions. The receptor is thought to be coupled to adenylate cyclase in an inhibitory manner in cerebral cortex, vascular smooth muscle cells, and SK-N-MC. [For a review, see, B. J. McDermott, et al., *Cardiovascular Research*, 27:893–905 (1993)]. This action is prevented by application of pertussis toxin confirming the role of a G-protein coupled receptor. The Y-1 receptor mediates the mobilization of intracellular calcium in a porcine vascular smooth muscle cells and human erythroleukemia cells.

The cloned human Y-1 receptor can couple to either phosphotidylinositol hydrolysis or the inhibition of adenylate cyclase, depending on the type of cell in which the receptor is expressed. H. Herzog, et al., *Proceedings of the National Academy of Sciences (USA)*, 89:5794–5798 (1992). The Y-1 receptor has been reported to couple to either second messenger system when studied using tissue preparations or cell lines naturally expressing the receptor. D. Gehlert, supra, at 553. The Y-1 receptor cannot, therefore, be distinguished solely on the basis of coupling to a single second messenger.

Y-2 Receptor

As with the Y-1 receptor, this receptor subtype was first delineated using vascular preparations. Pharmacologically, the Y-2 receptor is distinguished from Y-1 by exhibiting affinity for C-terminal fragments of neuropeptide Y. The receptor is most often differentiated by the use of neuropeptide Y(13–36), though the 3–36 fragment of neuropeptide Y and peptide YY provides improved affinity and selectivity. Y. Dumont, et al., *Society for Neuroscience Abstracts*, 19:726 (1993). Like Y-1 receptor, this receptor is coupled to the inhibition of adenylate cyclase, though in some preparations it may not be sensitive to pertussis toxin. The Y-2 receptor was found to reduce the intracellular levels of clacium in the synspse by selective inhibition of N-type calcium channels. Like the Y-1 receptor, the Y-2 receptor may exhibit differential coupling to second messengers.

The Y-2 receptors are found in a variety of brain regions, including the hippocampus, substantia nigralateralis, thalamus, hypothalamus, and brainstem. In the periphery, Y-2 is found in the peripheral nervous system, such as sympathetic, parasympathetic, and sensory neurons. In all these tissues, Y-2 receptors mediate a decrease in the release of neurotransmitters.

Y-3 Receptor

This receptor is the newest and least studied of the established neuropeptide Y receptor subtypes. While neuropeptide Y is a fully efficacious agonist at this receptor population, peptide YY is weakly efficacious. This pharmacological property is used to define this receptor. A receptor that has similar pharmacology to the Y-3 receptor has been identified in the CA3 region of the hippocampus using electrophysiological techniques. This receptor may potentiate the excitatory response of these neurons to N-methyl-D-aspartate (NMDA). F. P. Monnet, et al., *European Journal of Pharmacology*, 182:207–208 (1990).

The presence of this receptor is best established in the rat brainstem, specifically in the nucleus tractus solitarius. Application of neuropeptide Y to this region produces a dose-dependent reduction in blood pressure and heart rate. This area of the brain also may have significant contributions from the Y-1 and Y-2 receptor. Neuropeptide Y also inhibits the acetylcholine-induced release of catecholamines from the adrenal medulla, presumably through a Y-3 receptor. C. Wahlestedt, et al., *Life Sciences,* 50:PL7–PL14 (1992).

Peptide YY Preferring Receptor

A fourth receptor has been described that exhibits a modest preference for peptide YY over neuropeptide Y. This receptor was first described in the rat small intestine as having a 5–10 fold higher affinity for peptide YY over neuropeptide Y. M. Laburthe, et al., *Endocrinology,* 118:1910–1917 (1986). Subsequently, this receptor was found in the adipocyte and a kidney proximal tubule cell line. This receptor is coupled in an inhibitory manner to adenylate cyclase and is sensitive to pertussis toxin.

In the intestine, this receptor produces a potent inhibition of fluid and electrolyte secretion. The receptor is localized to the crypt cells where intestinal chloride secretion is believed to take place. The peptide YY preferring receptor in adipocytes mediates a reduction in lipolysis by way of a cyclic adenosine monophosphate (cAMP)-dependent mechanism.

"Feeding Receptor"

One of the earliest discovered central effects of neuropeptide Y was a profound increase in food intake that was observed following the hypothalmic administration of the peptide to rats. The response was greatest when the peptide was infused into the perifornical region of the hypothalamus. B. G. Stanley, et al., *Brain Research,* 604:304–317 (1993). while the pharmacology of this response resembled the Y-1 receptor, the 2–36 fragment of neuropeptide Y was significantly more potent than neuropeptide Y. In addition, intracerebroventricular neuropeptide Y(2–36) fully stimulates feeding, but does not reduce body temperature as does full length neuropeptide Y. F. B. Jolicoeur, et al., *Brain Research Bulletin,* 26:309–311 (1991).

Experimental Methods

Experiments were done with five to six month old male, inbred normal ICR mice, inbred normal(OB/?), obese-diabetic mice (ob/ob) from the Jackson Laboratories (Bar Harbor, Me.) or Harlan (England), and obese-diabetic (db/db) mice.

Both normal and diabetic mice were housed three or six per plastic cage (with bedding) and water and feed were available ad libitum. The temperature of animal rooms was maintained at 23±2° C. and lights were on from 0600 to 1800 h. Blood samples were collected from the tail vein. The most closely related biological test is, therefore, to inject the test article by any of several routes of administration (e.g., i.v., s.c., i.p., or by minipump or cannula) and then to monitor food and water consumption, body weight gain, plasma chemistry or hormones (glucose, insulin, ACTH, corticosterone, GH, T4) over various time periods. Suitable test animals include normal mice (ICR, etc.) and obese mice (ob/ob, Avy/a, KK-Ay, tubby, fat). Controls for nonspecific effects for these injections can be done using vehicle with or without test articles of similar composition in the same animal monitoring the same parameters or the test article itself in animals that are thought to lack the receptor (db/db mice, fa/fa or cp/cp rats).

As the target tissue is expected to be the hypothalamus where food intake and lipogenic state are regulated, another more elegant model would use similar test animals but would inject the test article directly into the brain (e.g., i.c.v. injection via lateral or third ventricles, or directly into specific hypothalamic nuclei (e.g. arcuate, paraventricular, perifornical nuclei). The same parameters as above could be measured, or the release of neurotransmitters that are known to regulate feeding or metabolism could be monitored (e.g. neuropeptide Y, galanin, norepinephrine, dopamine, β-endorphin release).

Similar studies could be accomplished in vitro using isolated hypothalamic tissue in a perifusion or tissue bath system. In this situation, the release of neurotransmitters or electrophysiological changes could be monitored.

Analytical methods

Blood glucose of mice was measured by a glucose oxidase method. Plasma glucose of rats was measured by a coupled hexokinase method. Plasma insulin was determined with radioimmunoassay kits using rat insulin as the standard. Plasma triglycerides of mice and rats were measured using commercial kits with glycerol as the standard. Neuropeptide Y was extracted using solid-phase C-18 cartriges and measured by radioimmuneassay.

In vitro studies

Ther region from the arcuate nucleus to the thalamus and between the optic chiasm and mammiliary bodies was surgically removed and placed in a perfusion system. When low glucose media or media containing corticosterone were infused, neuropeptide Y was released in a peak during early time points. Human ob gene product inhibited neuropeptide Y release under these conditions, in a manner similar to insulin. The sensitivity of the assay prevented analysis of ob gene product effects on neuropeptide Y in the basal state, that is without stimulation by either corticosterone or low glucose in the perifusion medium.

Inhibition of neuropeptide Y release and the potent effects of ob gene product when administered i.c.v suggested that the site of action and perhaps may be the hypothalamus. The protein Met-Arg-SEQ ID NO:4 was iodinated using standard techniques. High affinity binding sites were detected when isolated hypothalmic plasma membranes were incubated with [$^{125}$I]Met-Arg-SEQ ID NO:4 and then free bound separated by filtration. Density of receptors and affinity suggested a high level expression in the hypothalamus.

These studies demonstrate that ob gene product regulated food intake and body weight in normal ICR and genetically obese ob/ob mice. Chronic adminstration to ob/ob mice reversed the obese condition of these animals showing the potential promise for this protein as a treatment for obesity.

The hypothalamus has been thought to be the site of regulation of the adiposity set point since the early hypothalamus lesion studies. The observation that hypothalamic neuropeptide Y levels, elevated in the ob/ob mouse, were normalized by chronic treatment with ob gene product suggests that ob gene product acts to regulate the expression of neuropeptide Y. The suppression of neuropeptide Y release by ob gene product was observed in the isolated, perifused hypothalamus when neuropeptide Y release was stimulated by corticosterone.

As the compounds employed in the present invention reduce the output of neuropeptide Y, these compounds have value in the treatment of a wide variety of clinical conditions which are characterized by the presence of an excess of neuropeptide Y. Thus, the invention provides methods for the treatment or prevention of a physiological disorder associated with an excess of neuropeptide Y, which method comprises administering to a mammal in need of said treatment an effective amount of a protein as described infra. The term "physiological disorder associated with an excess of neuropeptide Y" encompasses those disorders associated with an inappropriate stimulation of neuropeptide Y receptors, regardless of the actual amount of neuropeptide Y present in the locale.

These physiological disorders include:

disorders or diseases pertaining to the heart, blood vessels or the renal system, such as vasospasm, heart failure, shock, cardiac hypertrophy, increased blood pressure, angina, myocardial infarction, sudden cardiac death, arrythmia, peripheral vascular disease, and abnormal renal conditions such as impaired flow of fluid, abnormal mass transport, or renal failure;

conditions related to increased sympathetic nerve activity for example, during or after coronary artery surgery, and operations and surgery in the gastrointestinal tract;

cerebral diseases and diseases related to the central nervous system, such as cerebral infarction, neurodegeneration, epilepsy, stroke, and conditions related to stroke, cerebral vasospasm and hemorrhage, depression, anxiety, schizophrenia, and dementia;

conditions related to pain or nociception;

diseases related to abnormal gastrointestinal motility and secretion, such as different forms of ileus, urinary incontinence, and Crohn's disease;

abnormal drink and food intake disorders, such as obesity, anorexia, bulimia, and metabolic disorders;

diseases related to sexual dysfunction and reproductive disorders;

conditions or disorders associated with inflammation;

respiratory diseases, such as asthma and conditions related to asthma and bronchoconstriction; and diseases related to abnormal hormone release, such as leutinizing hormone, growth hormone, insulin, and prolactin.

Yiying Zhang et al., in *Nature (London)*, 372:425–32 (1994) report the cloning of the murine obese (ob) mouse gene and present mouse DNA and the naturally occurring amino acid sequence of the obesity protein for the mouse and human. This protein is speculated to be a hormone that is secreted by fat cells and controls body weight.

The present invention provides methods employing biologically active proteins that provide effective treatment for conditions associated with neuropeptide Y and related peptides, as described infra.

The claimed proteins ordinarily are prepared by recombinant techniques. Techniques for making substitutional mutations at predetermined sites in DNA having a known sequence are well known, for example M13 primer mutagenesis. The mutations that might be made in the DNA encoding the present anti-obesity proteins must not place the sequence out of reading frame and preferably will not create complementary regions that could produce secondary mRNA structure. See, DeBoer, et al., European Patent Publication, 075,444 A (1983).

The compounds of the present invention may be produced either by recombinant DNA technology or well known chemical procedures, such as solution or solid-phase peptide synthesis, or semi-synthesis in solution beginning with protein fragments coupled through conventional solution methods.

Solid Phase Synthesis

The synthesis of the claimed protein may proceed by solid phase peptide synthesis or by recombinant methods. The principles of solid phase chemical synthesis of polypeptides are well known in the art and may be found in general texts in the area such as H. Dugas and C. Penney, BIOORGANIC CHEMISTRY, (1981) at pages 54–92. For example, peptides may be synthesized by solid-phase methodology utilizing an PE-Applied Biosystems 430A peptide synthesizer (commercially available from Applied Biosystems, Foster City Calif.) and synthesis cycles supplied by Applied Biosystems. t-Butoxycarbonyl (Boc)-protected amino acids and other reagents are commercially available from chemical supply houses. Sequential Boc chemistry using double couple protocols are applied to the starting p-methyl benzhydryl amine resins for the production of C-terminal carboxamides. For the production of C-terminal acids, the corresponding PAM resin is used. Arginine, Asparagine, Glutamine, Histidine and Methionine are coupled using preformed hydroxy benzotriazole esters. The following side chain protection may be used:

Arg, Tosyl

Asp, cyclohexyl or benzyl

Cys, 4-methylbenzyl

Glu, cyclohexyl

His, benzyloxymethyl

Lys, 2-chlorobenzyloxycarbonyl

Met, sulfoxide

Ser, Benzyl

Thr, Benzyl

Trp, formyl

Tyr, 4-bromo carbobenzoxy

Boc deprotection may be accomplished with trifluoroacetic acid (TFA) in methylene chloride. Formyl removal from Trp is accomplished by treatment of the peptidyl resin with 20% piperidine in dimethylformamide for 60 minutes at 4° C. Met(O) can be reduced by treatment of the peptidyl resin with TFA/dimethylsulfide/concHCl (95/5/1) at 25° C. for 60 minutes. Following the above pre-treatments, the peptides may be further deprotected and cleaved from the resin with anhydrous hydrogen fluoride containing a mixture of 10% m-cresol or m-cresol/10% p-thiocresol or m-cresol/p-thiocresol/dimethyl-sulfide. Cleavage of the side chain protecting group(s) and of the peptide from the resin is carried out at zero degrees Centigrade or below, preferably −20° C. for thirty minutes followed by thirty minutes at 0° C. After removal of the HF, the peptide/resin is washed with ether. The peptide is extracted with glacial acetic acid and lyophilized. Purification is accomplished by reverse-phase C18 chromatography (Vydac) column in 0.1% TFA with a gradient of increasing acetonitrile concentration.

One skilled in the art recognizes that the solid phase synthesis could also be accomplished using the FMOC strategy and a TFA/scavenger cleavage mixture.

B. Recombinant Synthesis

The claimed proteins may also be produced by recombinant methods. Recombinant methods are preferred if a high yield is desired. The basic steps in the recombinant production of protein include:

a) construction of a synthetic or semi-synthetic (or isolation from natural sources) DNA encoding the claimed protein, b) integrating the coding sequence into an expression vector in a manner suitable for the expression of the protein either alone or as a fusion protein, c) transforming an appropriate eukaryotic or prokaryotic host cell with the expression vector, and d) recovering and purifying the recombinantly produced protein.

a. Gene Construction

Synthetic genes, the in vitro or in vivo transcription and translation of which will result in the production of the protein may be constructed by techniques well known in the art. Owing to the natural degeneracy of the genetic code, the skilled artisan will recognize that a sizable yet definite number of DNA sequences may be constructed which encode the claimed proteins. In the preferred practice of the invention, synthesis is achieved by recombinant DNA technology.

Methodology of synthetic gene construction is well known in the art. For example, see Brown, et al. (1979) Methods in Enzymology, Academic Press, N.Y., Vol. 68, pgs. 109–151. The DNA sequence corresponding to the synthetic claimed protein gene may be generated using conventional DNA synthesizing apparatus such as the Applied Biosystems Model 380A or 380B DNA synthesizers (commercially available from Applied Biosystems, Inc., 850 Lincoln Center Drive, Foster City, Calif. 94404).

It may be desirable in some applications to modify the coding sequence of the claimed protein so as to incorporate a convenient protease sensitive cleavage site, e.g., between the signal peptide and the structural protein facilitating the controlled excision of the signal peptide from the fusion protein construct.

The gene encoding the claimed protein may also be created by using polymerase chain reaction (PCR). The template can be a cDNA library (commercially available from CLONETECH or STRATAGENE) or mRNA isolated from human adipose tissue. Such methodologies are well known in the art Maniatis, et al. *Molecular Cloning: A Laboratory Manual*, Cold Spring Harbor Press, Cold Spring Harbor Laboratory, Cold Spring Harbor, N.Y. (1989).

b. Direct expression or Fusion protein

The claimed protein may be made either by direct expression or as fusion protein comprising the claimed protein followed by enzymatic or chemical cleavage. A variety of peptidases (e.g. trypsin) which cleave a polypeptide at specific sites or digest the peptides from the amino or carboxy termini (e.g. diaminopeptidase) of the peptide chain are known. Furthermore, particular chemicals (e.g. cyanogen bromide) will cleave a polypeptide chain at specific sites. The skilled artisan will appreciate the modifications necessary to the amino acid sequence (and synthetic or semi-synthetic coding sequence if recombinant means are employed) to incorporate site-specific internal cleavage sites. See e.g., P. Carter, "Site Specific Proteolysis of Fusion Proteins", Ch. 13 in PROTEIN PURIFICATION: FROM MOLECULAR MECHANISMS TO LARGE SCALE PROCESSES, American Chemical Society, Washington, D.C. (1990).

c. Vector Construction

Construction of suitable vectors containing the desired coding and control sequences employ standard ligation techniques. Isolated plasmids or DNA fragments are cleaved, tailored, and religated in the form desired to form the plasmids required.

To effect the translation of the desired protein, one inserts the engineered synthetic DNA sequence in any of a plethora of appropriate recombinant DNA expression vectors through the use of appropriate restriction endonucleases. The claimed protein is a relatively large protein. A synthetic coding sequence is designed to possess restriction endonuclease cleavage sites at either end of the transcript to facilitate isolation from and integration into these expression and amplification and expression plasmids. The isolated cDNA coding sequence may be readily modified by the use of synthetic linkers to facilitate the incorporation of this sequence into the desired cloning vectors by techniques well known in the art. The particular endonucleases employed will be dictated by the restriction endonuclease cleavage pattern of the parent expression vector to be employed. The choice of restriction sites are chosen so as to properly orient the coding sequence with control sequences to achieve proper in-frame reading and expression of the claimed protein.

In general, plasmid vectors containing promoters and control sequences which are derived from species compatible with the host cell are used with these hosts. The vector ordinarily carries a replication site as well as marker sequences which are capable of providing phenotypic selection in transformed cells. For example, *E. coli* is typically transformed using pBR322, a plasmid derived from an *E. coli* species (Bolivar, et al., *Gene*, 2:95 (1977)). Plasmid pBR322 contains genes for ampicillin and tetracycline resistance and thus provides easy means for identifying transformed cells. The pBR322 plasmid, or other microbial plasmid must also contain or be modified to contain promoters and other control elements commonly used in recombinant DNA technology.

The desired coding sequence is inserted into an expression vector in the proper orientation to be transcribed from a promoter and ribosome binding site, both of which should be functional in the host cell in which the protein is to be expressed. An example of such an expression vector is a plasmid described in Belagaje, et al., U.S. Pat. No. 5,304,493, the teachings of which are herein incorporated by reference. The gene encoding A-C-B proinsulin described in U.S. Pat. No. 5,304,493 can be removed from the plasmid pRB182 with restriction enzymes NdeI and BamHI. The genes encoding the protein of the present invention can be inserted into the plasmid backbone on a NdeI/BamHI restriction fragment cassette.

d. Procaryotic expression

In general, procaryotes are used for cloning of DNA sequences in constructing the vectors useful in the invention. For example, *E. coli* K12 strain 294 (ATCC No. 31446) is particularly useful. Other microbial strains which may be used include *E. coli* B and *E. coli* X1776 (ATCC No. 31537). These examples are illustrative rather than limiting.

Prokaryotes also are used for expression. The aforementioned strains, as well as *E. coli* W3110 (prototrophic, ATCC No. 27325), bacilli such as *Bacillus subtilis*, and other enterobacteriaceae such as *Salmonella typhimurium* or *Serratia marcescans*, and various pseudomonas species may be used. Promoters suitable for use with prokaryotic hosts include the β-lactamase (vector pGX2907 [ATCC 39344] contains the replicon and β-lactamase gene) and lactose promoter systems (Chang et al., *Nature (London)*, 275:615 (1978); and Goeddel et al., *Nature (London)*, 281:544 (1979)), alkaline phosphatase, the tryptophan (trp) promoter system (vector pATH1 [ATCC 37695] is designed to facilitate expression of an open reading frame as a trpE fusion protein under control of the trp promoter) and hybrid promoters such as the tac promoter (isolatable from plasmid pDR540 ATCC-37282). However, other functional bacterial promoters, whose nucleotide sequences are generally known, enable one of skill in the art to ligate them to DNA encoding the protein using linkers or adaptors to supply any required restriction sites. Promoters for use in bacterial systems also will contain a Shine-Dalgarno sequence operably linked to the DNA encoding protein.

e. Eucaryotic expression

The protein may be recombinantly produced in eukaryotic expression systems. Preferred promoters controlling transcription in mammalian host cells may be obtained from various sources, for example, the genomes of viruses such as: polyoma, Simian Virus 40 (SV40), adenovirus, retroviruses, hepatitis-B virus and most preferably cytomegalovirus, or from heterologous mammalian promoters, e.g. β-actin promoter. The early and late promoters of the SV40 virus are conveniently obtained as an SV40 restriction fragment which also contains the SV40 viral origin of replication. Fiers, et al., *Nature (London)*, 273:113 (1978). The entire SV40 genome may be obtained from plasmid pBRSV, ATCC 45019. The immediate early promoter of the human cytomegalovirus may be obtained from plasmid pCMBβ (ATCC 77177). Of course, promoters from the host cell or related species also are useful herein.

Transcription of a DNA encoding the claimed protein by higher eukaryotes is increased by inserting an enhancer sequence into the vector. Enhancers are cis-acting elements of DNA, usually about 10–300 bp, that act on a promoter to increase its transcription. Enhancers are relatively orientation and position independent having been found 5' (L. Laimins, et al., *Proceedings of the National Academy of Sciences*, 78:993 (1981)) and 3' (M. L. Lusky, et al., *Molecular and Cellular Biology*, 3:1108 (1983)) to the transcription unit, within an intron (J. L. Banerji, et al., *Cell*, 33:729 (1983)) as well as within the coding sequence itself (T. F. Osborne, et al., *Molecular and Cellular Biology*, 4:1293 (1984)). Many enhancer sequences are now known from mammalian genes (globin, RSV, SV40, EMC, elastase, albumin, α-fetoprotein and insulin). Typically, however, one will use an enhancer from a eukaryotic cell virus. Examples include the SV40 late enhancer, the cytomegalovirus early promoter enhancer, the polyoma enhancer on the late side of the replication origin, and adenovirus enhancers.

Expression vectors used in eukaryotic host cells (yeast, fungi, insect, plant, animal, human or nucleated cells from other multicellular organisms) will also contain sequences necessary for the termination of transcription which may affect mRNA expression. These regions are transcribed as polyadenylated segments in the untranslated portion of the mRNA encoding protein. The 3' untranslated regions also include transcription termination sites.

Expression vectors may contain a selection gene, also termed a selectable marker. Examples of suitable selectable markers for mammalian cells are dihydrofolate reductase (DHFR, which may be derived from the BglII/HindIII restriction fragment of pJOD-10 [ATCC 68815]), thymidine kinase (herpes simplex virus thymidine kinase is contained on the BamHI fragment of vP-5 clone [ATCC 2028]) or neomycin (G418) resistance genes (obtainable from pNN414 yeast artificial chromosome vector [ATCC 37682]). When such selectable markers are successfully transferred into a mammalian host cell, the transfected mammalian host cell can survive if placed under selective pressure. There are two widely used distinct categories of selective regimes. The first category is based on a cell's metabolism and the use of a mutant cell line which lacks the ability to grow without a supplemented media. Two examples are: CHO DHFR⁻ cells (ATCC CRL-9096) and mouse LTK⁻ cells (L-M(TK-) ATCC CCL-2.3). These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in nonsupplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, Southern P. and Berg, P., *J. Molec. Appl. Genet.* 1: 327 (1982), mycophenolic acid, Mulligan, R. C. and Berg, P. *Science* 209:1422 (1980), or hygromycin, Sugden, B. et al., *Mol Cell. Biol.* 5:410–413 (1985). The three examples given above employ bacterial genes under eukaryotic control to convey resistance to the appropriate drug G418 or neomycin (geneticin), xgpt (mycophenolic acid) or hygromycin, respectively.

A preferred vector for eucaryotic expression is pRc/CMV. pRc/CMV is commercially available from Invitrogen Corporation, 3985 Sorrento Valley Blvd., San Diego, Calif. 92121. To confirm correct sequences in plasmids constructed, the ligation mixtures are used to transform *E. coli* K12 strain DH5α (ATCC 31446) and successful transformants selected by antibiotic resistance where appropriate. Plasmids from the transformants are prepared, analyzed by restriction and/or sequence by the method of Messing, et al., *Nucleic Acids Res.* 9:309 (1981).

Host cells may be transformed with the expression vectors of this invention and cultured in conventional nutrient media modified as is appropriate for inducing promoters, selecting transformants or amplifying genes. The culture conditions, such as temperature, pH and the like, are those previously used with the host cell selected for expression, and will be apparent to the ordinarily skilled artisan. The techniques of transforming cells with the aforementioned vectors are well known in the art and may be found in such general references as Maniatis, et al., *Molecular Cloning: A Laboratory Manual*, Cold Spring Harbor Press, Cold Spring Harbor Laboratory, Cold Spring Harbor, N.Y. (1989), or *Current Protocols in Molecular Biology* (1989) and supplements.

Preferred suitable host cells for expressing the vectors encoding the claimed proteins in higher eukaryotes include: African green monkey kidney line cell line transformed by SV40 (COS-7, ATCC CRL-1651); transformed human primary embryonal kidney cell line 293,(Graham, F. L. et al., *J. Gen Virol.* 36:59–72 (1977), *Virology* 77:319–329, *Virology* 86:10–21); baby hamster kidney cells (BHK-21(C-13), ATCC CCL-10, *Virolooy* 16:147 (1962)); chinese hamster ovary cells CHO-DHFR⁻ (ATCC CRL-9096), mouse Sertoli cells (TM4, ATCC CRL-1715, *Biol. Reprod.* 23:243–250 (1980)); african green monkey kidney cells (VERO 76, ATCC CRL-1587); human cervical epitheloid carcinoma cells (HeLa, ATCC CCL-2); canine kidney cells (MDCK, ATCC CCL-34); buffalo rat liver cells (BRL 3A, ATCC CRL-1442); human diploid lung cells (WI-38, ATCC CCL-75); human hepatocellular carcinoma cells (Hep G2, ATCC HB-8065);and mouse mammary tumor cells (MMT 060562, ATCC CCL51).

f. Yeast expression

In addition to prokaryotes, eukaryotic microbes such as yeast cultures may also be used. *Saccharomyces cerevisiae*, or common baker's yeast is the most commonly used eukaryotic microorganism, although a number of other strains are commonly available. For expression in Saccharomyces, the plasmid YRp7, for example, (ATCC-40053, Stinchcomb, et al., *Nature* 282:39 (1979); Kingsman et al., *Gene* 7:141 (1979); Tschemper et al., *Gene* 10:157

(1980)) is commonly used. This plasmid already contains the trp gene which provides a selection marker for a mutant strain of yeast lacking the ability to grow in tryptophan, for example ATCC no. 44076 or PEP4-1 (Jones, *Genetics* 85:12 (1977)).

Suitable promoting sequences for use with yeast hosts include the promoters for 3-phosphoglycerate kinase (found on plasmid pAP12BD ATCC 53231 and described in U.S. Pat. No. 4,935,350, Jun. 19, 1990) or other glycolytic enzymes such as enolase (found on plasmid PAC1 ATCC 39532), glyceraldehyde-3-phosphate dehydrogenase (derived from plasmid pHcGAPC1 ATCC 57090, 57091), zymomonas mobilis (U.S. Pat. No. 5,000,000 issued Mar. 19, 1991), hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein (contained on plasmid vector pCL28XhoLHBPV ATCC 39475, U.S. Pat. No. 4,840,896), glyceraldehyde 3-phosphate dehydrogenase, and enzymes responsible for maltose and galactose (GAL1 found on plasmid pRY121 ATCC 37658) utilization. Suitable vectors and promoters for use in yeast expression are further described in R. Hitzeman et al., European Patent Publication No. 73,657A. Yeast enhancers such as the UAS Gal from *Saccharomyces cerevisiae* (found in conjunction with the CYC1 promoter on plasmid YEpsec--hI1beta ATCC 67024), also are advantageously used with yeast promoters.

The following examples are presented to further illustrate the preparation of the claimed proteins. The scope of the present invention is not to be construed as merely consisting of the following examples.

Example 1

A gene encoding the human obesity sequence with a Met-Arg leader sequence of SEQ ID NO:5 is assembled from a ~220 base pair and a ~240 base pair segment which are derived from chemically synthesized oligonucleotides.

in length from between 34 and 83 bases. The 240 base pair segment which extends from the XbaI to the BamHI site is also assembled from 7 overlapping oligonucleotides which range in length from between 57 and 92 bases.

To assemble these fragments, the respective 7 oligonucleotides are mixed in equimolar amounts, usually at concentrations of about 1–2 picomoles per microliters. Prior to assembly, all but the oligonucleotides at the 5"-ends of the segment are phosphorylated in standard kinase buffer with T4 DNA kinase using the conditions specified by the supplier of the reagents. The mixtures are heated to 95 degrees and allowed to cool slowly to room temperature over a period of 1–2 hours to ensure proper annealing of the oligonucleotides. The oligonucleotides are then ligated to each other and into an appropriated cloning vector such as pUC18 or pUC 19 using T4 DNA ligase. The buffers and conditions are those recommended by the supplier of the enzyme. The vector for the 220 base pair fragment is digested with NdeI and XbaI, whereas the vector for the 240 base pair fragment is digested with XbaI and BamHI prior to use. The ligation mixes are used to transform *E. coli* DH10B cells (commercially available from Gibco/BRL) and the transformed cells are plated on tryptone-yeast (TY) plates containing 100 µg/ml of ampicillin, X-gal and IPTG. Colonies which grow up overnight are grown in liquid TY medium with 100 µg/ml of ampicillin and are used for plasmid isolation and DNA sequence analysis. Plasmids with the correct sequence are kept for the assembly of the complete gene. This is accomplished by gel-purification of the 220 base-pair and the 240 base-pair fragments and ligation of these two fragments into an expression vector such as pRB182 from which the coding sequence for A-C-B proinsulin is deleted and is digested with NdeI and BamHI prior to use.

Example 2

The plasmid containing the DNA sequence encoding the desired protein, is digested with PmlI and Bsu36I. The recognition sequences for these enzymes lie within the coding region for the protein at nucleotide positions 275 and 360 respectively. The cloning vector does not contain these recognition sequences. Consequently, only two fragments are seen following restriction enzyme digestion with PmlI and Bsu36I, one corresponding to the vector fragment, the

```
  1  CATATGAGGG TACCTATCCA AAAAGTACAA GATGACACCA AAACACTGAT SEQ ID NO: 5

51  AAAGACAATA GTCACAAGGA TAAATGATAT CTCACACACA CAGTCAGTCT

101  CATCTAAACA GAAAGTCACA GGCTTGGACT TCATACCTGG GCTGCACCCC

151  ATACTGACAT TGTCTAAAAT GGACCAGACA CTGGCAGTCT ATCAACAGAT

201  CTTAACAAGT ATGCCTTCTA GAAACGTGAT ACAAATATCT AACGACCTGG

251  AGAACCTGCG GGATCTGCTG CACGTGCTGG CCTTCTCTAA AAGTTGCCAC

301  TTGCCATGGG CCAGTGGCCT GGAGACATTG GACAGTCTGG GGGGAGTCCT

351  GGAAGCCTCA GGCTATTCTA CAGAGGTGGT GGCCCTGAGC AGGCTGCAGG

401  GGTCTCTGCA AGACATGCTG TGGCAGCTGG ACCTGAGCCC CGGGTGCTAA

451  TAGGATCC
```

The 220 base pair segment extends from the NdeI site to the XbaI site at position 220 within the coding region and is assembled from 7 overlapping oligonucleotides which range other corresponding to the ~85 base pair fragment liberated from within the protein coding sequence. This sequence can be replaced by any DNA sequence encoding the amino acid substitutions listed in Table 1. These DNA sequences are synthesized chemically as two oligonucleotides with complementary bases and ends that are compatible with the ends generated by digestion with PmlI and Bsu36I. The chemically synthesized oligonucleotides are mixed in equimolar amounts (1–10 picomoles/microliter), heated to 95 degrees and allow to anneal by slowly decreasing the temperature to 20–25 degrees. The annealed oligonucleotides are used in a standard ligation reaction. Ligation products are tranformed and analysed as described in Example 1.

Example 3

A DNA sequence encoding Compound 255 with a Met Arg leader sequence was obtained using the plasmid and procedures described in Example 2. The plasmid was digested with Pm1I and Bsu36I. A synthetic DNA fragment was inserted between the PmlI and the Bsu36I sites. Following ligation, transformation and plasmid isolation, the sequence of the synthetic fragment was verified by DNA sequence analysis.

The techniques of transforming cells with the aforementioned vectors are well known in the art and may be found in such general references as Maniatis, et al., MOLECULAR CLONING: A LABORATORY MANUAL, Cold Spring Harbor Press, Cold Spring Harbor Laboratory, Cold Spring Harbor, N.Y. (1988), or CURRENT PROTOCOLS IN MOLECULAR BIOLOGY, (F. Ausabel, ed., 1989) and supplements thereof. The techniques involved in the transformation of $E.$ $coli$ cells used in the preferred practice of the invention as exemplified herein are well known in the art. The precise conditions under which the transformed $E.$ $coli$ cells are cultured is dependent on the nature of the $E.$ $coli$ host cell line and the expression or cloning vectors employed. For example, vectors which incorporate thermoinducible promoter-operator regions, such as the c1857 thermoinducible lambda-phage promoter-operator region, require a temperature shift from about 30° C. to about 40° C. in the culture conditions so as to induce protein synthesis.

In the preferred embodiment of the invention $E.$ $coli$ K12 RV308 cells are employed as host cells but numerous other cell lines are available such as, but not limited to, $E.$ $coli$ K12 L201, L687, L693, L507, L640, L641, L695, L814 ($E.$ $coli$ B). The transformed host cells are then plated on appropriate media under the selective pressure of the antibiotic corresponding to the resistance gene present on the expression plasmid. The cultures are then incubated for a time and temperature appropriate to the host cell line employed.

Proteins which are expressed in high-level bacterial expression systems characteristically aggregate in granules or inclusion bodies which contain high levels of the overexpressed protein. See, e.g., Kreuger et al., PROTEIN FOLDING, (Gierasch and King, eds., 1990) at pages 136–142, American Association for the Advancement of Science Publication No. 89-18S, Washington, D.C. Such protein aggregates must be solubilized to provide further purification and isolation of the desired protein product. Id. A variety of techniques using strongly denaturing solutions such as guanidinium-HCl and/or weakly denaturing solutions such as dithiothreitol (DTT) are used to solubilize the proteins.

Gradual removal of the denaturing agents (often by dialysis) in a solution allows the denatured protein to assume its native conformation. The particular conditions for denaturation and folding are determined by the particular protein expression system and/or the protein in question.

Example 4

Compound 255 with a Met Arg leader sequence (MR 255) was folded either by dilution into PBS or by dilution into 8M urea (both containing 5 mM cysteine) and exhaustive dialysis against PBS. Little to no aggregation of protein was seen in either of these procedures. Following final purification of the proteins by size exclusion chromatography the proteins were concentrated to 3–3.5 mg/mL in PBS. Virtually no aggregation of either protein was noted in contrast to the native human protein for which substantial aggregation is noted upon concentration.

Analysis of the proteins by reverse phase HPLC indicated that the human Ob protein eluted at approximately 56.6% acetonitrile, the mouse protein at 55.8%, and Compound 255 with a Met Arg leader sequence at 53.7%. Thus, unexpectedly the human with the mouse insert appears to have higher hydrophilicity than either the human or mouse molecules.

Preferably, the present proteins are expressed as Met-Arg-SEQ ID NO: 1 so that the expressed proteins may be readily converted to the claimed protein with cathepsin C (also known as diaminopeptidase). The purification of proteins is by techniques known in the art and includes reverse phase chromatography, affinity chromatography, and size exclusion chromatography.

The claimed proteins contain two cysteine residues. Thus, a di-sulfide bond may be formed to stabilize the protein. The present invention includes proteins of SEQ ID NO:1 and SEQ ID NO:2 wherein the Cys at position 96 is crosslinked to Cys at position 146 as well as those proteins without such di-sulfide bonds.

In addition the proteins of the present invention may exist, particularly when formulated, as dimers, trimers, tetramers, and other multimers. Such multimers are included within the scope of the present invention.

The present invention provides a method for treating conditions associated with an excess of neuropeptide Y. The method comprises administering to the organism an effective amount of anti-obesity protein in a dose between about 1 and 1000 µg/kg. A preferred dose is from about 10 to 100 µg/kg of active compound. A typical daily dose for an adult human is from about 0.5 to 100 mg. In practicing this method, compounds of SEQ ID NO:1 or SEQ ID NO:2 can be administered in a single daily dose or in multiple doses per day. The treatment regime may require administration over extended periods of time. The amount per administered dose or the total amount administered will be determined by the physician and depend on such factors as the nature and severity of the disease, the age and general health of the patient and the tolerance of the patient to the compound.

The instant invention further provides pharmaceutical formulations comprising compounds of the present invention. The proteins, preferably in the form of a pharmaceutically acceptable salt, can be formulated for parenteral administration for the therapeutic or prophylactic treatment of obesity. For example, compounds of SEQ ID NO:2 can be admixed with conventional pharmaceutical carriers and excipients. The compositions comprising claimed proteins contain from about 0.1 to 90% by weight of the active protein, preferably in a soluble form, and more generally from about 10 to 30%. Furthermore, the present proteins may be administered alone or in combination with other anti-obesity agents or agents useful in treating diabetes.

For intravenous (iv) use, the protein is administered in commonly used intravenous fluid(s) and administered by infusion. Such fluids, for example, physiological saline, Ringers solution or 5% dextrose solution can be used.

For intramuscular preparations, a sterile formulation, preferably a suitable soluble salt form of a protein of SEQ ID NO:1, for example the hydrochloride salt, can be dissolved and administered in a pharmaceutical diluent such as pyrogen-free water (distilled), physiological saline or 5% glucose solution. A suitable insoluble form of the compound may be prepared and administered as a suspension in an aqueous base or a pharmaceutically acceptable oil base, e.g. an ester of a long chain fatty acid such as ethyl oleate.

The methods of the present invention, in addition to the obesity proteins, examples of which are described above, also employ various neuropeptide Y antagonsits. Recent publications and co-pending patent applications describe various groups of such antagonists.

Patent Cooperation Treaty Patent Publication WO 94/00486, published Jan. 6, 1994 describes a series of neuropeptide Y antagonists of a peptidyl nature.

A multimer as employed in the present invention includes a dimer or trimer. Such normally occur when peptides containing Gly residues are bridged at the alpha position by a group selected from the following:

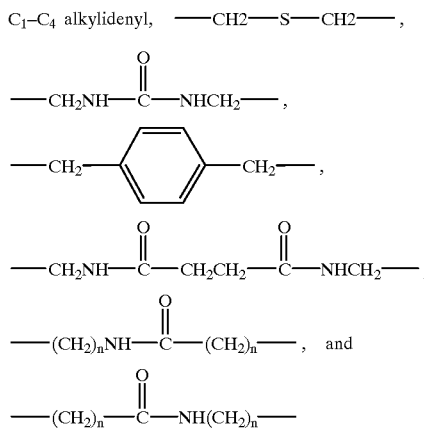

in which n is as defined herein. Alternatively, such multimers may also occur when peptides are lactam bridged. Such multimers can contain one or more such bridges, preferably two. It is preferred that a peptidyl neuropeptide Y antagonist employed the methods of the present invention is used in the form of a dimer.

European Patent Publication 716,854, published Jun. 19, 1996, describes a series of non-peptidyl neuropeptide Y antagonists of the formula

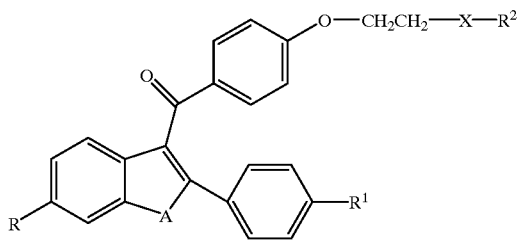

wherein:

A is —O—, —S(O)$_m$—, —N(R$^{11}$)—, —CH$_2$CH$_2$—, or —CH═CH—;

m is 0, 1, or 2;

X is a bond or C$_1$–C$_4$ alkylidenyl;

R$^2$ is a group of the formula

wherein R$^4$ and R$^5$ are independently C$_1$–C$_6$ alkyl or combine to form, along with the nitrogen to which they are attached, a heterocyclic ring selected from the group consisting of hexamethyleneiminyl, piperazino, heptamethyleneiminyl, 4-methylpiperidinyl, imidazolinyl, piperidinyl, pyrrolidinyl, or morpholinyl;

R is hydroxy, halo, hydrogen, C$_3$–C$_8$ cycloalkyl, C$_2$–C$_7$ alkanoyloxy, C$_1$–C$_6$ alkoxy, or phenyl, said phenyl being optionally substituted with one, two, or three moieties selected from the group consisting of C$_1$–C$_4$ alkyl, C$_1$–C$_4$ alkoxy, nitro, chloro, fluoro, trifluoromethyl —OSO$_2$—(C$_1$–C$_{10}$ alkyl) or

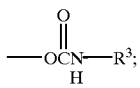

R$^1$ is hydroxy, halo, hydrogen, C$_3$–C$_8$ cycloalkyl, C$_2$–C$_7$ alkanoyloxy, C$_1$–C$_6$ alkoxy, or phenyl, said phenyl being optionally substituted with one, two, or three moieties selected from the group consisting of C$_1$–C$_4$ alkyl, C$_1$–C$_4$ alkoxy, nitro, chloro, fluoro, trifluoromethyl —OSO$_2$—(C$_1$–C$_{10}$ alkyl) or

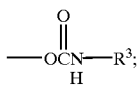

each R$^3$ is independently C$_1$–C$_6$ alkyl, C$_3$–C$_8$ cycloalkyl, unsubstituted or substituted phenyl where the substituent is halo, C$_1$–C$_6$ alkyl or C$_1$–C$_6$ alkoxy;

or a pharmaceutically acceptable salt or solvate thereof.

As used herein, the term "C$_1$–C$_{10}$ alkyl" refers to straight or branched, monovalent, saturated aliphatic chains of 1 to 10 carbon atoms and includes, but is not limited to, methyl, ethyl, propyl, isopropyl, butyl, isobutyl, t-butyl, pentyl, isopentyl, and hexyl. The term "C$_1$–C$_{10}$ alkyl" includes within its definition the terms "C$_1$–C$_4$ alkyl" and "C$_1$–C$_6$ alkyl".

"C$_1$–C$_6$ alkoxy" represents a straight or branched alkyl chain having from one to six carbon atoms attached to an oxygen atom. Typical C$_1$–C$_6$ alkoxy groups include methoxy, ethoxy, propoxy, isopropoxy, butoxy, t-butoxy, pentoxy and the like. The term "C$_1$–C$_6$ alkoxy" includes within its definition the term "C$_1$–C$_4$ alkoxy".

"C$_1$–C$_6$ alkylidenyl" refers to a straight or branched, divalent, saturated aliphatic chains of 1 to 6 carbon atoms and includes, but is not limited to, methylenyl, ethylenyl, propylenyl, isopropylenyl, butylenyl, isobutylenyl, t-butylenyl, pentylenyl, isopentylenyl, hexylenyl, and the like. The term "C$_1$–C$_4$ alkylidenyl" is encompassed within the term "C$_1$–C$_6$ alkylidenyl".

The term "halo" encompasses chloro, fluoro, bromo and iodo.

The term "leaving group" as used herein refers to a group of atoms that is displaced from a carbon atom by the attack of a nucleophile in a nucleophilic substitution reaction. The term "leaving group" as used in this document encompasses, but is not limited to, activating groups.

The term "activating group" as used herein refers a leaving group which, when taken with the carbonyl (—C=O) group to which it is attached, is more likely to take part in an acylation reaction than would be the case if the group were not present, as in the free acid. Such activating groups are well-known to those skilled in the art and may be, for example, succinimidoxy, phthalimidoxy, benzotriazolyloxy, benzenesulfonyloxy, methanesulfonyloxy, toluenesulfonyloxy, azido, or —O—CO—($C_4$-$C_7$ alkyl).

Many of the compounds employed in the present invention are derivatives of naphthalene which are named and numbered according to the RING INDEX, The American Chemical Society, as follows.

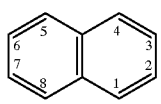

In a similar manner some of the compounds employed in the present invention are derivatives of 1,2-dihydronaphthalene which are named and numbered according to the RING INDEX as follows.

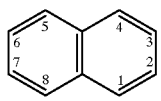

Many of the compounds of the present invention are derivatives of benzofuran which are named and numbered according to the RING INDEX, The American Chemical Society, as follows.

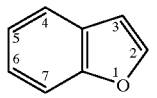

Some of the compounds of the present invention are derivatives of benzo[b]thiophene which are named and numbered according to the RING INDEX as follows.

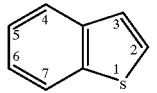

In a similar manner some of the compounds of the present invention are derivatives of indole which are named and numbered according to the RING INDEX as follows.

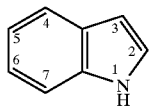

The more preferred compounds employed in the methods of this invention are those compounds of Formula I wherein
a) A is —O—, —S—, —$CH_2$—$CH_2$—, or —CH=CH—;
b) R is hydrogen, hydroxy, $C_1$-$C_3$ alkoxy, or —$OSO_2$—($C_1$-$C_{10}$ alkyl);

c) $R^1$ is hydrogen, hydroxy, $C_1$-$C_3$ alkoxy, or —$OSO_2$—($C_1$-$C_{10}$ alkyl);

d) X is a bond or methylene; and e) $R^2$ is piperidinyl, hexamethyleneiminyl, pyrrolidinyl, or —$NR^4R^5$, where $R^4$ and $R^5$ are $C_1$-$C_4$ alkyl; and the pharmaceutically acceptable acid addition salts and solvates.

The most preferred compounds employed in the methods of this invention are those compounds of Formula I wherein a) A is —S—;

b) R is hydrogen, hydroxy, $C_1$-$C_3$ alkoxy, or —$OSO_2$—($C_1$-$C_{10}$ alkyl);

c) $R^1$ is hydrogen, hydroxy, $C_1$-$C_3$ alkoxy, or —$OSO_2$—($C_1$-$C_{10}$ alkyl);

d) X is a bond or methylene; and e) $R^2$ is piperidinyl, hexamethyleneiminyl, pyrrolidinyl, or —$NR^4R^5$, where $R^4$ and $R^5$ are $C_1$-$C_4$ alkyl; and f) at least one of R and $R^1$ is —$OSO_2$—($C_1$-$C_{10}$ alkyl);

and the pharmaceutically acceptable acid addition salts and solvates thereof.

The most preferred compound employed in the methods of the present invention is raloxifene, a compound having the structure

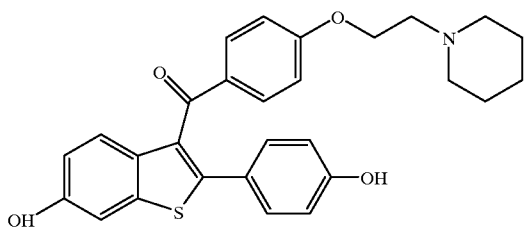

and the chemical name 6-hydroxy-2-(4-hydroxyphenyl)-3-{4-[2-(piperidin-1-yl)ethoxy]benzoyl}benzo[b]thiophene hydrochloride. This compound may be synthesized as described in U.S. Pat. Nos. 4,133,814, 4,418,068, and 4,380,635, all of which are incorporated by reference herein.

The compounds of the present invention can be prepared by a variety of procedures well known to those of ordinary skill in the art. The particular order of steps required to produce the compounds of Formula I is dependent upon the particular compound being synthesized, the starting compound, and the relative lability of the substituted moieties.

A. Preparation of Dihydronapthalenyl Compounds

The compounds employed in the present invention in which A is —$CH_2$—$CH_2$— or —CH=CH— may be prepared essentially as described in U.S. Pat. No. 4,230,862, issued to T. Suarez and C. D. Jones on Oct. 28, 1990, which is herein incorporated by reference.

These compounds are generally prepared by the following sequences, the dihydronaphthalene structures in general being precursors to the napthalene compounds.

The naphthalenes and dihydronaphthalenes employed in the methods of the instant invention may be prepared by reacting a tetralone of Formula II

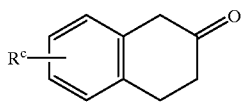

in which $R^c$ is hydrogen, $C_1$–$C_6$ alkoxy, or benzyloxy with a phenyl benzoate of Formula III

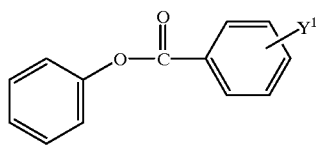

in which $Y^1$ is methoxy, benzyloxy, or —O—$(CH_2)_n$—$NR^aR^b$, where n is 1–6, and —$NR^aR^b$ is $R^2$. This reaction is generally carried out in the presence of a moderately strong base such as sodium amide and at room temperature or below.

The product which is obtained is a substituted tetralone of Formula IV.

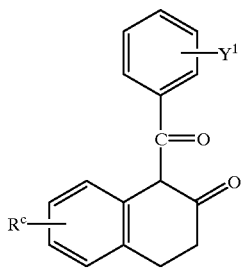

This substituted tetralone is then reacted under Grignard reaction conditions with the Grignard reagent of the formula

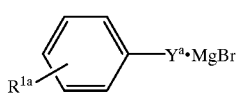

in which $R^{1a}$ is hydrogen, $C_1$–$C_6$ alkoxy, or benzyloxy and $Y^a$ is a bond, methylene, or ethylene.

The compounds which are produced, a 3-phenyl-4-aroyl-1,2-dihydronaphthalenes, have the following formula, Formula V.

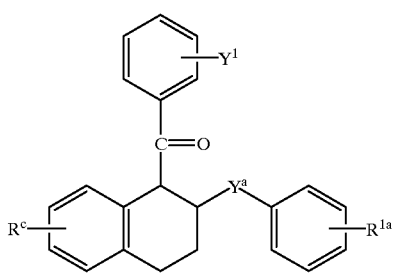

In those instances in which $Y^1$ is methoxy, a compound of Formula V can be treated with pyridine hydrochloride at reflux to produce the corresponding hydroxy compound. Under these conditions, should $R^c$ or $R^{1a}$ be alkoxy or benzyloxy, these groups will also be cleaved, resulting in hydroxy groups.

In those instances in which $Y^1$ is methoxy or benzyloxy, and $R^c$ or $R^{1a}$ is alkoxy or benzyloxy, the group at $Y^1$ can be selectively cleaved by treating a compound of Formula V with an equivalent of sodium thioethoxide in N,N-dimethylformamide at a moderately elevated temperature of about 80° C. to about 90° C. The process of the selective cleavage may be monitored by periodic thin layer chromatography analysis. The reaction is complete when little or no starting material remains.

Once the compound of Formula V in which $Y^1$ has been converted to hydroxy has been generated, that compounds can then be treated with a compound of Formula VII

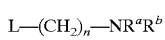

wherein L is a good leaving group such as halo, especially chloro. Under the usual reaction conditions, of course, alkylation will be effected at each of the unprotected hydroxy groups which are present in the molecule. This can be avoided, and alkylation at the 4-benzoyl groups alone can be achieved, by carrying out the reaction in the presence of an excess of finely powdered potassium carbonate and using an equivalent or slight excess of the compound of Formula VII.

Depending upon the intended structure of the final product, the compound containing the substituent of Formula VII can then be further treated with an additional quantity of sodium thioethoxide in N,N-dimethylformamide as aforedescribed to effect cleavage of any remaining alkoxy or benzyloxy groups, thereby providing another sequence for achieving formation of those compounds employed in this invention in which $R^1$ and/or $R^2$ are hydroxy.

In any of the above, it is evident that the particular sequence of synthetic steps designed to produce a compound having substituents of particular definition and location is such as one of ordinary skill in the art will well recognize.

In another route for preparing the compounds of Formula I, compounds of Formula VI

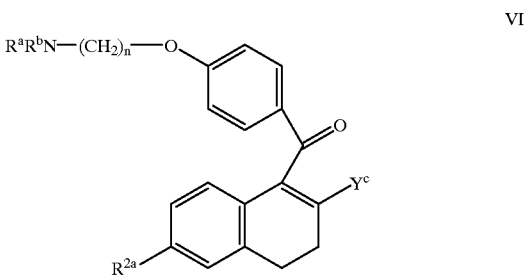

wherein: $R^{2a}$ is —H or $C_1$–$C_6$ alkoxy; and $Y^c$ is $C_1$–$C_6$ alkoxy-substituted phenyl or benzyl, are prepared essentially as described by C. D. Jones, et al., *Journal of Medicinal Chemistry,* 53:931–938 (1992), which is herein incorporated by reference.

Generally, a tetralone, as described above, or a salt thereof, is acylated using standard Friedel Crafts conditions to provide a highly enolized diketone of formula VIa

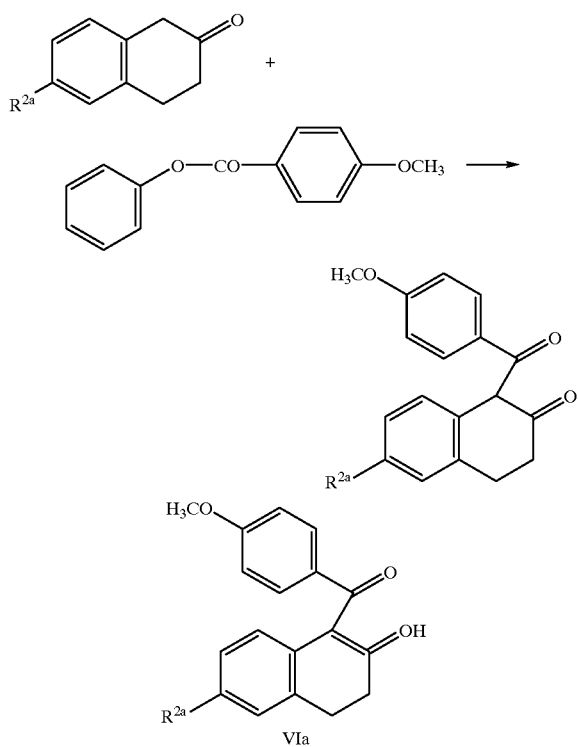

wherein $R^{2a}$ is —H or $C_1$–$C_6$ alkoxy.

Subsequent derivatization using sodium hydride, followed by the addition of diphenyl chlorophosphate, gives the enol phosphate derivative tentatively assigned the Formula VIb

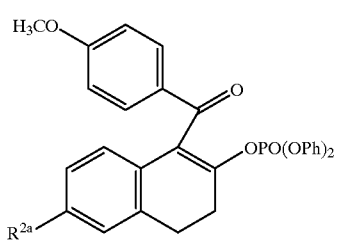

wherein $R^{2a}$ is as defined above.

Addition of phenyl- or benzyl-, substituted phenyl- or substituted benzylmagnesium bromide to a compound of formula VIb, and subsequent selective demethylation provide compounds of formula VIc and VId, respectively, as described by Jones, supra.

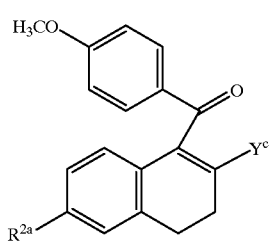

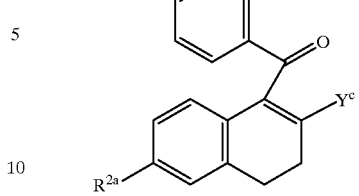

wherein $R^{2a}$ and $Y^c$ are as defined above.

Finally a compound of formula VId is alkylated with a compound of the formula

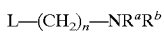

L—(CH$_2$)$_n$—NR$^a$R$^b$ in which L is a bromo or, preferably, a chloro moiety, and $R^{2a}$ and $Y^c$ optionally are dealkylated by standard procedures, to provide compounds of formulae VIe and VIf, respectively.

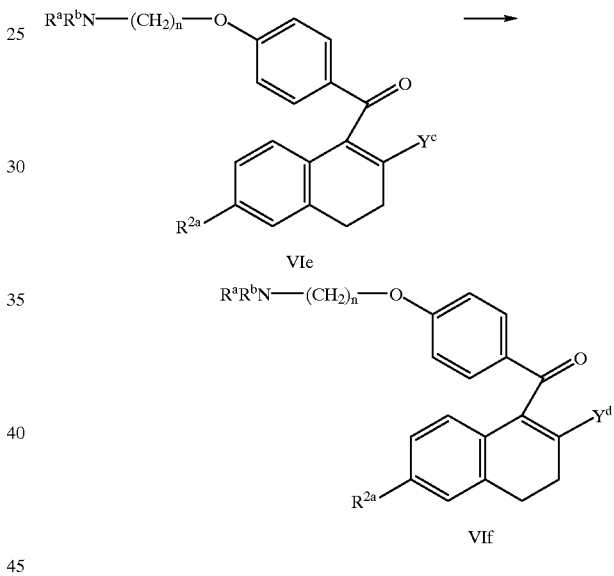

wherein $R^{2b}$ is —H or —OH and $Y^d$ is phenyl, benzyl, hydroxyphenyl, or hydroxybenzyl.

In the process for preparing compounds of formula VIe or VIf, it is evident that the particular sequence of synthetic steps designed to produce a compound having substituents of particular definition and location is such as one of ordinary skill in the art will recognize.

The compounds of Formula VIf can be substituted using standard means, if desired, to produce the corresponding dihydronaphthenyl compounds of Formula I.

B. Preparation of Napthalenyl Compounds

Those compounds of Formula I which are substituted naphthalenes are readily prepared from the corresponding dihydronaphthalenyl compounds. Selective dehydrogenation of the dihydronaphthalene structure to produce specifically the corresponding naphthalene can be accomplished by treatment with 2,3-dichloro-5,6-dicyano-1,4-benzoquinone (DDQ) at a temperature of from about 50° C. to about 100° C. The naphthalene which is produce may be further converted to other naphthalene compounds by means of the derivatizing reactions described supra.

Example 1

Preparation of 3-(4-methoxyphenyl)-4-[4-(2-pyrrolidin-1-ylethoxy)benzoyl-1,2-dihydronaphthalene, citrate salt The title compound was prepared as described in U.S. Pat. No. 4,230,862. To a suspension of sodium amide (15.2 g, 0.38 mol) in 250 ml of tertrahydrofuran were added 50 grams (0.34 mol) of β-tetralone. The mixture was stirred for 15–20 minutes, and 78 grams of phenyl p-methoxybenzoate dissolved in tetrahydrofuran were added. The temperature of the reaction mixture was maintained below 10° C., and the mixture was then stirred at room temperature overnight. The reaction mixture was concentrated and the water was added to the residue. The aqueous mixture was extracted with ethyl acetate, and the ethyl acetate extract was washed and concentrated.

The residue was chromatographed on silica using benzene as eluant. The purer fractions obtained by the chromatographic separation were combined and concentrated, and the residue was dissolved in a minimum of methanol. The methanol was cooled, and 35.2 grams of 1-(4-methoxybenzoyl)-2-tetralone were collected by filtration.

4-Bromoanisole (18.7 g, 0.1 mol) was added dropwise in ether to tetrahydrofuran containing 5 drops of 1,2-dibromoethane and 3.6 grams (0.15 mol) of magnesium. Reaction occurred almost immediately, and the addition was continued at a slow rate with evolution of heat sufficient to maintain a general reflux. Upon completion of the addition, the above substituted β-tetralone dissolved in acetone was added dropwise with stirring over a two hour period, the mixture being maintained at 40° C. The resulting mixture was then poured into cold, dilute hydrochloric acid, and the acidic mixture was extracted with ethyl acetate. The ethyl acetate extract was washed, dried, and concentrated to an oil. The oil was chromatographed over silica using benzene as eluant. A subsequent elution of the column with a mixture of benzene containing two percent ethyl acetate yielded 15 grams of 3-(4-methoxyphenyl)-4-(4-methoxybenzoyl)-1,2-dihydronaphthalene as an oil.

A mixture of 11.1 grams (0.03 mol) of the above dimethoxy product, 7.2 grams of sodium hydride (50 percent in oil), and 11 ml of ethyl mercaptan in N,N-dimethylformamide was prepared. The mixture was heated to 65–70° C. and maintained at that temperature for about two hours. The mixture was then cooled and conetrated. The concentrate was acidified and extracted with ethyl acetate. The ethyl acetate extract was washed, dried, and evaporated. The residue was dissolved in benzene and chromatographed over silica to obtain five grams of an oil comprising relatively pure 3-(4-methoxyphenyl)-4-(4-hydroxybenzoyl)-1,2-dihydronaphthalene.

The above phenolic product (4.3 g, 0.01 mol) was dissolved in N,N-dimethylformamide. To this solution was added 0.7 grams of sodium hydride (50 percent in oil), and the resulting mixture was warmed to 40° C. for one hour and then was cooled to room temperature. To the mixture then were added 1.6 grams of 1-chloro-2-pyrrolidinylethane, and the mixture was warmed to 60° C. and maintained at this temperature for about two hours. The reaction mixture was then stirred at room temperature overnight.

The mixture was concentrated, and water was added to the residue. The aqueous mixture was extracted with ethyl acetate. The ethyl acetate extract was washed and concentrated to a residue. The residue was extracted with hexanes, the insoluble portion was dissolved in ethyl acetate, and the ethyl acetate solution was extracted with 1 N hydrochloric acid. The acid extract was rendered alkaline, and then was extracted with ethyl acetate. The ethyl acetate extract was washed and concentrated. One equivalent of citric acid in acetone then was added to the concentrate, and the mixture was concentrated to dryness. The residue was dissolved in a large volume of methyl ethyl ketone. The ketone solution was concentrated to about 300 ml and was cooled to 0° C. The title product, the citrate salt of 3-(4-methoxyphenyl)-4-[4-(2-pyrrolidin-1-ylethoxy)benzoyl-1,2-dihydronaphthalene, was collected by filtration and vacuum dried. mp 82–85° C.

Analysis for $C_{36}H_{39}NO_{10}$: Theory: C, 66.96; H, 6.09; N, 2.17; O, 24.78. Found: C, 66.70; H, 6.27; N, 2.27; O, 24.54.

Example 2

Preparation of 3-phenyl-4-[4-(2-pyrrolidin-1-ylethoxy)benzoyl]-7-methoxy-1,2-dihydronaphthalene The title product was prepared as described in U.S. Pat. No. 4,230,862. To 300 ml of N,N-dimethylformamide were added 107 grams of phenyl p-hydroxybenzoate and 26 grams of sodium hydride (50 percent in oil). The mixture was heated to 60° C. and maintained at this temperature for about two hours. To this mixture was added 1-chloro-2-pyrrolidin-1-ylethane (67 g), and the mixture was stirred overnight at 85° C. The bulk of the N,N-dimethylformamide then was evaporated from the mixture. Water was added to the residue, and the aqueous mixture was extracted with ethyl acetate. The ethyl acetate extract was concentrated, and the residue was dissolved in a 1:1 mixture of ether and ethyl acetate. The organic solution was then extracted with 2 N hydrochloric acid, and the acid extract was added dropwise to 2 N sodium hydroxide. The resulting mixture was extracted with ethyl acetate, and the ethyl acetate extract was washed and then dried over magnesium sulfate. The ethyl acetate was concentrated to obtain 110 grams of crude phenyl p-(2-pyrrolidin-1-ylethoxy)benzoate.

To a suspension of 20 grams (0.5 mol) of sodium amide in tetrahydrofuran were added dropwise 41.7 grams of 6-methoxy-2-tetralone in tetrahydrofuran, the temperature of the mixture being maintained below 10° C. Upon completion of the addition, the mixture was stirred for 20 minutes, the reaction mixture being maintained below 10° C., after which time an exothermic reaction occurred, the reaction temperature rising to about 20° C.

The above prepared phenyl p-(2-pyrrolidin-1-ylethoxy) benzoate, dissolved in tetrahydrofuran, was then added dropwise, and the mixture was stirred overnight at room temperature. The mixture was poured into water, and the resulting mixture was extracted with ethyl acetate. The ethyl acetate extract was washed several times with water, and dried over magnesium sulfate. The ethyl acetate was concentrated to obtain about 100 grams of crude material which was dissolved in 1.5 liters of acetone, and one equivalent of citric acid in 400 ml of ethyl acetate was added. The resulting solid was isolated by filtration and vacuum dried to obtain 85.9 grams of 6-methoxy-1-[4-(2-pyrrolidin-1-ylethoxy)benzoyl]-2-tetralone. The product was then chromatographed over silica using ethyl acetate as eluant, and the citrate salt was prepared from the recovered product.

The above product (8.6 g, 0.02 mol) was added to a solution of phenylmagnesium bromide in tetrahydrofuran. The resulting mixture was stirred for one hour at room temperature and then was warmed to 50° C. and maintained at this temperature for three hours. The resulting mixture was poured into a mixture of ice and hydrochloric acid, and the acid mixture was extracted with ethyl acetate. The ethyl acetate extract was washed, dried, and concentrated to obtain 10.5 grams of a red-brown oil. The oil was added to 500 ml of acetic acid, and the mixture was heated on a steam bath for about 30 minutes. The acid was stripped off, and water as added to the residue.

The aqueous mixture was rendered alkaline by addition of base, and the alkaline mixture was extracted with ethyl acetate. The extract was dried and concentrated to obtain 8.7 grams of product which was dissolved in acetone, and one equivalent of citric acid was added to the mixture. The acetone was stripped off, and methyl ethyl ketone was added to the residue. The mixture was maintained at 0° C. overnight, and the crystals which formed were collected by filtration and washed with cold methyl ethyl ketone and vacuum dried. The solid was recrystallized from acetone to obtain the title compound in the form of its citrate salt. mp 98–100° C.

Analysis of $C_{36}H_{39}NO_{10}$: Theory: C, 66.96; H, 6.09; N, 2.17; O, 24.78. Found: C, 66.72; H, 6.27; N, 2.09; O, 24.50.

The title compound in the form of its free base was generated by treatment of the citrate salt with dilute alkali.

Analysis for $C_{30}H_{31}NO_5$: Theory: C, 79.44; H, 6.89; N, 3.09. Found: C, 79.19; H, 6.68; N, 2.91.

Example 3

Preparation of 3-phenyl-4-[4-(2-pyrrolidin-1-ylethoxy)benzoyl]-1,2-dihydronaphthalene The title product was prepared as described in U.S. Pat. No. 4,230,862. To a solution of 5.0 grams (18 mmol) of 1-(4-methoxybenzoyl)-2-tetralone (prepared as described in Example 1) in 50 ml of ether was added dropwise at 0° C. a solution of phenylmagnesium bromide (18 mmol) in 9 ml of ether. Upon completion of the addition, the mixture was stirred for twenty minutes. Thin layer chromatography of the reaction mixture indicated the presence of starting material. An additional 13.5 ml of the phenylmagnesium bromide solution were added.

The mixture was refluxed for two hours and then was cooled and poured over iced aqueous ammonium chloride solution. The organic layer was separated and washed with brine. The mixture was then dried over magnesium sulfate, filtered, and evaporated to give about ten grams of a yellow oil. After a wash with hexanes, the product was further purified by chromatography to give 4.67 grams of 3-phenyl-4-(4-methoxybenzoyl)-1,2-dihydronaphthalene.

To 2.0 grams (6 mmol) of the above dihydronaphthalene, dissolved in 10 ml of N,N-dimethylformamide, were added sodium thioethoxide (7.5 mmol), dissolved in 15 ml of N,N-dimethylformamide. The addition was carried out under a nitrogen atmosphere and at 80° C. The mixture was maintained at 80° C. for fifteen hours. The mixture was then cooled and poured into an iced aqueous ammonium chloride solution. The resulting mixture was extracted with ethyl acetate, and the ethyl acetate extract was washed four times with brine.

The ethyl acetate extract was dried over magnesium sulfate an evaporated to give an oil which was further purified by chromatography on a silica column, using benzene to elute impurities. The product was then eluted with ethyl acetate to give, upon evaporation of the ethyl acetate, 1.69 grams of 3-phenyl-4-(4-hydroxybenzoyl)-1,2-dihydronaphthalene as a clear pale yellow oil.

A mixture of 1.61 grams (4.95 mmol) of the above product in 10 ml of dry N,N-dimethylformamide containing 119 mg (4.95 mmol) of sodium hydride and freshly distilled 1-chloro-(2-pyrrolidin-1-yl)ethane. The addition was made under a nitrogen atmosphere with the temperature being maintained at about 10° C. Upon completion of the resulting efferverscence, the mixture was heated to 80° C. and maintained at that temperature for about two hours. The mixture was then poured into water, and the total was extract with ether. The ether extract was washed five times with brine, and dried over magnesium sulfate. The ether layer was then filtered and evaporated to give a gray oil, which was further purified by chromatography to give 3-phenyl-4-[4-(2-pyrrolidin-1-ylethoxy)benzoyl]-1,2-dihydronaphthalene.

The product was converted to the corresponding citrate salt by treatment with 0.59 grams of citric acid in 50 ml of hot acetone. The resulting mixture was evaporated to dryness, and the residue was stirred for about fifteen hours with ether to obtain the citrate salt. mp 89–93° C.

Analysis for $C_{33}H_{37}NO_9 \cdot 0.5\ H_2O$: Theory: C, 67.34; H, 6.13; N, 2.25. Found: C, 67.06; H, 6.41; N, 2.66.

Example 4

Preparation of 1-[4-(2-pyrrolidin-1-ylethoxy)benzoyl]-2-phenylnaphthalene, citrate salt The title product was prepared as described in U.S. Pat. No. 4,230,862. To 30 ml of dioxane were added 3-phenyl-4-(4-methoxybenzoyl)-1,2-dihydronaphthalene (1.90 g, 5.58 mmol), prepared as described in Example 3, supra, and 2,3-dichloro-5,6-dicyano-1,4-benzoquinone (2.00 g, 8.81 mmol). The resulting mixture was heated to reflux and refluxed for twelve hours under a nitrogen atmosphere. The mixture was then cooled and evaporated to dryness. The residue was partitioned between ether and water. The organic fraction was washed 5 N sodium hydroxide (5×20 ml), followed by a wash with brine. The mixture was then dried over magnesium sulfate and evaporated to give 1.9 grams of substantially pure 1-(4-methoxybenzoyl)-2-phenylnaphthalene.

Employing substantially the same demethylation procedure as described in Example 3, 1.83 grams (5.41 mmol) of the above product were treated with sodium thioethoxide to obtain 1.4 grams of 1-(4-hydroxybenzoyl)-2-phenylnaphthalene.

To 10 ml of N,N-dimethylformamide were added 1.25 grams of the above product. The resulting mixture was added at about 10° C. to a mixture of 20 ml of N,N-dimethylformamide containing 120 mg (5.0 mmol) of sodium hydride and 800 mg of 1-chloro-2-(pyrrolidin-1-yl)ethane. Upon completion of the resulting effervescence, the mixture was heated to 80° C. and maintained at that temperature for about three hours, during which time sodium chloride precipitated. The mixture was cooled and evaporated to dryness. The resulting residue was partitioned between water and ethyl acetate. The organic fraction was washed with brine (5×25 ml). The organic fraction was dried and evaporated to give 1.62 grams of 1-[4-[2-(pyrrolidin-1-yl)ethoxy]benzoyl]-2-phenylnaphthalene as a yellow oil.

The above free base was converted to the corresponding citrate salt in accordance with the method of Example 3, employing 0.811 grams of citric acid hydrate. The title compound was obtained as an amorphous solid which crystallized on standing overnight in ether. mp 105–108° C.

Analysis for $C_{33}H_{35}NO_9 \cdot H_2O$: Theory: C, 65.55; H, 5.90; N, 2.22. Found: C, 66.90; H, 5.85; N, 2.25.

Example 5

Preparation of 3-(4-methoxyphenyl)-4-[4-[2-(piperidin-1-yl)ethoxy]benzoyl]-1,2-dihydronaphthalene, citrate salt The title compound was prepared as described in U.S. Pat. No. 4,230,862. To a suspension of sodium hydride (0.269 g, 11 mmol), washed free of mineral oil, and 1-chloro-2-(piperidin-1-yl)ethane (1.82 g, 12 mmol) in N,N-dimethylformamide (50 ml) at 0° C., and under a nitrogen atmosphere, were added 4.0 grams (10 mmol) of 3-(4-methoxyphenyl)-4-(4-hydroxybenzoyl)-1,2-dihydronaphthalene, prepared as described in Example 1, dissolved in 20 ml of N,N-dimethylformamide. The solution was added dropwise with stirring. When the effervescence had ceased for the most part, the mixture was heated to 50° C. and maintained at that temperature for several hours. The progress of the reaction was monitored by thin layer chromatography.

Once the reaction had progressed sufficiently, the N,N-dimethylformamide was evaporated, and the concentrated mixture was poured over ice water and ethyl acetate. The ethyl acetate fraction was washed with brine, dried over potassium carbonate, filtered, and evaporated, The resulting oil was chromatographed over a 1.5"×12" silica column using the following as a double gradient:

(i) 10 percent ethyl acetate in benzene (500 ml) →20 percent ethyl acetate in benzene (2 liters);

(ii) 20 percent ethyl acetate in benzene (1.5 liters) →1:1 mixture of methanol and ethyl acetate (1.5 liters).

The appropriate fractions were concentrated to give an almost colorless oil. The oil was dissolved in ethyl acetate, and the ethyl acetate solution was dried over potassium carbonate, filtered, and evaporated to give 4.7 grams of the free base of the title compound as a pale yellow oil.

The free base (3.4 g, 7.28 mmol) was treated with citric acid monohydrate (1.49 g, 7.1 mmol) in about 20 ml of boiling acetone. When a clear solution was obtained, the acetone was evaporated, 300 ml of anhydrous ether was added, and the resulting precipitate was stirred overnight. The title compound (5.2 grams) was collected as a white powder.

Analysis for $C_{37}H_{41}NO_{10}$: Theory: C, 67.36; H, 6.26; N, 2.12. Found: C, 67.25; H, 5.96; N, 1.84.

Example 6

Preparation of 3-(4-methoxyphenyl)-4-[4-(2-dimethylaminoethoxy)benzoyl]-1,2-dihydronaphthalene, citrate salt The title compound was prepared as described in U.S. Pat. No. 4,230,862. To 50 ml of acetone were added 4.0 grams (11.2 mmol) of 3-(4-methoxyphenyl)-4-(4-hydroxybenzoyl)-1,2-dihydronaphthalene, prepared as described in Example 1, 1.81 grams (16.8 mmol) of 1-chloro-2-dimethylaminoethane (freshly prepared from the hydrohloride), and 2.32 grams (16.8 mol) of finely powdered potassium chloride. The resulting mixture was refluxed under nitrogen with stirring for about 72 hours. The progress of the reaction was monitored by thin layer chromatography.

The resulting mixture was then poured over ice, and the resulting mixture was extracted with ether. The ether was washed three times with brine, dried over potassium carbonate, filtered, and evaporated to obtain 4.51 grams of the free base of the title compound as a brown oil.

The oil was vacuum dried and then was converted to the citrate salt by treatment with 2.17 grams (10.4 mmol) of citric acid monohydrate in 50 ml of hot acetone. Evaporation of the acetone and stirring of the residue with ether gave 5.2 grams of the title compound as an amorphous solid.

Analysis for $C_{34}H_{37}NO_{10}$: Theory: C, 65.90; H, 6.02; N, 2.26. Found: C, 66.17; H, 6.23; N, 2.37.

Example 7

Preparation of 3-(4-hydroxyphenyl)-4-[4-[2-(pyrrolidin-1-yl)ethoxy]benzoyl]-1,2-dihydronaphthalene, mesylate salt The title compound was prepared as described in U.S. Pat. No. 4,230,862. To 25 ml of methyl ethyl ketone were 10 grams (2.92 mmol) of 3-(4-hydroxyphenyl)-4-(4-hydroxybenzoyl)-1,2-dihydronaphthalene, 0.497 grams (2.92 mmol) of 1-chloro-2-(pyrrolidin-1-yl)ethane, and 1.21 grams (8.77 mmol) offinely powdered potassium carbonate. The resulting mixture was refluxed for 16 hours. The mixture was then cooled and poured into a mixture of water and ethyl acetate. The resulting mixture was rendered acidic by addition of 1 N hydrochloric acid and then alkaline by the addition of sodium bicarbonate.

The organic fraction was washed with brine, dried over magnesium sulfate, and evaporated to give a yellow oil. The resulting oil was further purified by chromatography. The free base (362 mg, 0.825 mmol) as converted to the mesylate aslt by treatment with an equivalent of methanesulfonic acid in acetone to yield the title compound as an amorphous solid.

Analysis for $C_{31}H_{37}NO_6S$: Theory: C, 67.27; H, 6.21; N, 2.61. Found: C, 67.25; H, 6.19; N, 2.69.

Example 8

Preparation of 3-(4-methoxyphenyl)-4-[4-[2-(hexamethyleneimin-1-yl)benzoyl]-1,2-dihydronaphthalene, mesylate salt The title compound was prepared as described in U.S. Pat. No. 4,230,826. To 50 ml of methyl ethyl ketone were added 3.0 g (8.43 mmol) of 3-(4-methoxyphenyl)-4-(4-hydroxybenzoyl)-1,2-dihydronaphthalene, 1.84 g (9.27 mmol) of 1-chloro-2-(hexamethyleneimin-1-yl)ethane hydrochloride, and 3.25 grams (25.3 mmol) of finely powdered potassium carbonate. The mixture was refluxed for 48 hours.

The mixture was then poured into water, and ethyl acetate was added. The resulting organic layer was separated, washed with brine, dried, and evaporated to a yellow oil. The oil was further purified by chromatography. The free base of the title compound was recovered (2.51 g) as a pale yellow oil. The oil was treated with 0.431 g (4.48 mmol) of methanesulfonic acid in 10 ml of acetone. Upon scratching and cooling of the mixture, crystals formed. The mixture was cooled overnight and 1.97 grams of the title compound were obtained as a white crystals. mp 123–125° C.

Analysis for $C_{34}H_{41}NO_6S$: Theory: C, 68.61; H, 6.80; N, 2.42. Found: C, 68.38; H, 6.62; N, 2.40.

Example 9

Preparation of 3-(4-methoxyphenyl)-4-[4-[2-(piperidin-1-yl)ethoxy]benzoyl]-1,2-dihydronaphthalene, mesylate salt The title compound was prepared as described in U.S. Pat. No. 4,230,862. To 150 ml of methyl ethyl ketone were added 7.8 g (21.9 mmol) of 3-(4-methoxyphenyl)-4-(4-hydroxybenzoyl)-1,2-dihydronaphthalene, 4.84 grams (23.6 mmol) of 1-chloro-2-(piperidin-1-yl)ethane hydrochloride, and 14.5 grams (109 mmol) of potassium carbonate. The resulting mixture was refluxed overnight.

The mixture was then poured into a mixture of water and ethyl acetate. The resulting orgnaic fraction was spearated, washed with brine, dried over magnesium sulfate, and evaporated in vacuo to obtain the free base of the title compound as a yellow oil.

The oil was dissolved in 30 ml of acetone and was treated with 2.105 grams (21.9 mmol) of methanesulfonic acid. The mixture was cooled and scratched, and the title compound was collected at −40° C. and ashed well with acetone and ether cooled to about −60° C. The solid was then vacuum dried at 100° C. to obtain 11.21 grams of the title compound as a white crystalline solid. mp 157–158° C.

Analysis for $C_{33}H_{39}NO_6S$: Theory: C, 68.18; H, 6.62; N, 2.48. Found: C, 68.11; H, 6.76; N, 2.50.

Example 10

Preparation of 3-(4-methoxyphenyl)-4-(4-diethylaminoethoxybenzoyl)-1,2-dihydronaphthalene, mesylate salt To 75 ml of methyl ethyl ketone were added 4.0 grams (11.2 mmol) of 3-(4-methoxyphenyl)-4-(4-hydroxybenzoyl)-1,2-dihydronaphthalene, 2.41 grams (14 mmol) of 1-chloro-2-diethylaminoethane hydrochloride, and 7.93 grams (56 mmol) of finely powdered potassium carbonate. The mixture was refluxed overnight, and, employing the method of Example 9, 5.67 grams of the free base of the title compound were obtained as a yellow oily material.

The oil was treated with 1.07 grams (11.2 mmol) of methanesulfonic acid in about 15 ml of acetone. The resulting mixture was maintained with cooling for several days after which white crystals appeared. The crystals were somewhat hygroscopic and were collected as quickly as possible and vacuum-dried. There were obtained 4.3 grams of the title compound as a white crystalline solid.

Analysis for $C_{31}H_{39}NO_6S$: Theory: C, 67.24; H, 7.10; N, 2.53. Found: C, 67.48; H, 6.92; N, 2.43.

Example 11

Preparation of 3-(4-methoxyphenyl)-4-(4-diisopropylaminoethoxybenzoyl)-1,2-dihydronaphthalene, mesylate salt To 75 ml of methyl ethyl ketone were added 3.84 grams (10.8 mmol) of 3-(4-methoxyphenyl)-4-(4-hydroxybenzoyl)-1,2-dihydronaphthalene, 2.70 grams (13.5 mmol) of 1-chloro-2-diisopropylaminoethane hydrochloride, and 7.11 grams (54 mmol) of finely powdered potassium carbonate. The mixture was allowed to reflux overnight, and, upon workup, in accordance with the procedure of Example 9, 5.64 grams of the free base of the title compound were obtained as a yellow oily substance. The oily product was treated with 1.04 grams (10.8 mmol) of methanesulfonic acid in about 25 ml of acetone. The mixture was cooled, and crystals slowly appeared. The crystals collected at −40° C. with the aid of acetone cooled to −60° C. Vacuum drying of the product gave 5.1 grams.

Analysis for $C_{33}H_{41}NO_6S$: Theory: C, 68.37; H, 7.31; N, 2.42. Found: C, 68.08; H, 6.91; N, 2.21.

The following compounds were prepared essentially as described in the above examples:

Example 12

3-hydroxy-4-[4-[2-(pyrrolidin-1-yl)ethoxy]benzoyl]-1,2-dihydronaphthalene, sodium salt Example 13

2-(4-methoxyphenyl)-1-[4-[2-(pyrrolidin-1-yl)ethoxy]benzoyl]naphthalene, mesylate salt Example 14

3-(4-methoxyphenyl)-4-[4-[2-(piperidin-1-yl)ethoxy]benzoyl]-7-methoxy-1,2-dihydronaphthalene, mesylate salt Example 15

3-(4-methoxyphenyl)-4-[4-(2-dimethylaminoethoxy)benzoyl]-1,2-dihydronaphthalene, 2-hydroxy-1,2,3-propanetricarboxylic acid salt Example 16

3-(4-methoxyphenyl)-4-[4-[2-(N-methyl-1-pyrrolidinium)ethoxy]benzoyl]-1,2-dihydronaphthalene, iodide salt Example 17

3-(4-methoxyphenyl)-4-[4-[2-(pyrrolidin-1-yl)ethoxy]benzoyl]-1,2-dihydronaphthalene, mesylate salt C. Preparation of Indoles, Benzofurans and Benzothiophenes The benzofurans, benzothiophenes and indoles employed in the methods of the instant invention were made essentially as described in U.S. Pat. No. 4,133,814, issued Jan. 9, 1979, U.S. Pat. No. 4,418,068, issued Nov. 29, 1983, and U.S. Pat. No. 4,380,635, issued Apr. 19, 1983, all of which are herein incorporated by reference. This process provides a convenient process which acylates a methylated starting compound and then optionally demethylates it to obtain the desired dihydroxy product. The acylation and demethylation may be performed in successive steps in a single reaction mixture or the intermediate may be isolated and the demethylation step be performed in a separate reaction.

The methyl-protected compound of Formula VII

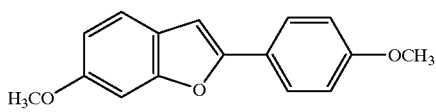

VII is most easily obtained by reacting 3-methoxyphenol and α-bromo-4-methoxyacetophenone in the presence of a strong base at a relatively low temperature, to form α-(3-methoxyphenoxy)-4-methoxyacetophenone, which is then ring closed with an agent such as polyphosphoric acid at a high temperature to obtain the intermediate compound of Formula VII.

The acylation of this invention is a Friedel-Crafts acylation, and is carried out in the usual way, using aluminum chloride or bromide, preferably the chloride, as the acylation catalyst.

The acylation is ordinarily carried out in a solvent, and any inert organic solvent which is not significantly attacked by the conditions may be used. For example, halogenated solvents such as dichloromethane, 1,2-dichloroethane, chloroform, and the like may be used, as can aromatics such as benzene, chlorobenzene, and the like. It is preferred to use a halogenated solvent, especially dichloromethane.

It has been found that toluene is rather easily acylated under the conditions used in the Friedel-Crafts acylation, and so it is important, when toluene is used in an earlier step of the process, to remove it as completely as possible from the protected starting compound, to avoid wasting the acylating agent.

The acylations may be carried out at temperatures from about −30° C. to about 100° C., preferably at about ambient temperature, in the range of from about 15° C. to about 30° C.

The acylating agent is an active form of the appropriate benzoic acid of Formula VIII

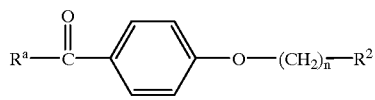

VIII wherein $R^a$ is chloro or bromo. The preferred acylating agents are those wherein $R^a$ is chloro. Thus, the most highly preferred individual acylating agents are 4-[2-(piperidin-1-yl)ethoxy]benzoyl chloride, 4-[2-(hexamethyleneimin-1-yl)ethoxy]benzoyl chloride, 4-[2-(pyrrolidin-1-yl)ethoxy]benzoyl chloride, 4-[2 -(dimethylamino)ethoxy]-benzoyl chloride, 4-[2-(diethylamino)ethoxy]benzoyl chloride, and 4-[2-(diisopropylamino)ethoxy]benzoyl chloride.

The acyl chloride used as an acylating agent may be prepared from the corresponding carboxylic acid by reaction with a typical chlorinating agent such as thionyl chloride. Care must be taken to remove any excess chlorinating agent from the acyl chloride. Most conveniently, the acyl chloride is formed in situ, and the excess chlorinating agent is distilled off under vacuum.

It is generally preferred that an equimolar amount of the compounds of Formula VII and VIII are reacted together. If desired, a small excess of either reactant may be added to assure the other is fully consumed. It is generally preferred to use a large excess of the acylation catalyst, such as about 2–12 moles per mole of product, preferably about 5–10 moles of catalyst per mole of product.

The acylation is rapid. Economically brief reaction times, such as from about 15 minutes to a few hours provide high yields of the acylated intermediate. Longer reaction times may be used if desired, but are not usually advantageous. As usual, the use of lower reaction temperatures call for relatively longer reaction times.

The acylation step is ended and the optional demethylation step is begun by the addition of a sulfur compound selected from the group consisting of methionine and compounds of the formula

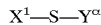

wherein $X^1$ is hydrogen or unbranched $C_1$–$C_4$ alkyl, and $Y^\alpha$ is $C_1$–$C_4$ alkyl or phenyl. The sulfur compounds are, preferably, the alkylthiols, such as methanethiol, ethanethiol, isopropanethiol, butanethiol, and the like; dialkyl sulfides, such as diethyl sulfide, ethyl propyl sulfide, butyl isopropyl sulfide, dimethyl sulfide, methyl ethyl sulfide, and the like; benzenethiol; methionine; and alkyl phenyl sulfides, such as methyl phenyl sulfide, ethyl phenyl sulfide, butyl phenyl sulfide, and the like.

It has been found that demethylation is most efficient when a substantial excess of the sulfur compound is used, in the range of about 4 to about 10 moles per mole of the starting benzofuran. The process may be carried out, although less efficiently, with a smaller amount of the sulfur compound (in the range of about 2 to 3 moles per mole of the starting compound). It is also possible to use a small amount of the sulfur compound, and to improve the yield by the addition of about 1 to 3 moles of an alkali metal halide, such as sodium, potassium, or lithium chloride, bromide, or iodide.

The demethylation reaction goes well at about ambient temperature, in the range of from about 15° C. to about 30° C., and such operation is preferred. The demethylation may be carried out, however, at temperatures in the range of from about −30° C. to about 50° C. if it is desired to do so. Short reaction times, in the range of about one hour, have been found to be sufficient.

After the product has been demethylated, it is recovered and isolated by conventional means. It is customary to add water to decompose the complex of the acylation catalyst. Addition of dilute aqueous acid is advantageous. The product precipitates in many instances, or may be extracted with an organic solvent according to conventional methods. The examples below further illustrate the isolation.

In an alternative process an intermediate compound of Formula IX

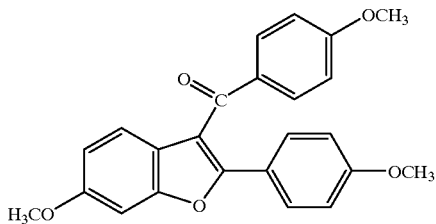

IX is synthesized by the reaction of 2-hydroxy-4-methoxybenzaldehyde and 1-(4-methoxyphenyl)-2-(4-methoxyphenyl)ethanone, essentially as described in Preparation 3a, infra. This reaction usually employs equimolar amounts of the two reactants although other ratios are operable. The reaction is performed in a non-reactive solvent such as ethyl acetate, chloroform, and the like, in the presence of an acid. Hydrochloric acid, particularly when created by bubbling anhydrous hydrogen chloride, is an especially preferred acid. Lower alkyl alcohols are usually added to the non-polar solvent so as to retain more of the hydrochloric acid created in situ, with ethanol and methanol being especially preferred. The reaction is performed at temperatures ranging from ambient temperature up to the reflux temperature of the mixture. This reaction results in the synthesis of a compound of Formula X

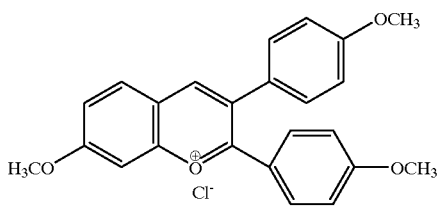

X or an equivalent anion if hydrochloric acid is not used, which is then oxidized to the compound of Formula IX by the addition of hydrogen peroxide. The intermediate of Formula X may be isolated or may preferably be converted to the compound of Formula IX in the same reaction vessel.

The compound of Formula IX is then selectively demethylated, essentially as described in Preparation 4a, infra to yield the compound of Formula XI

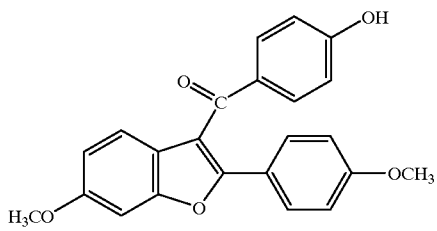

XI

The ether of the compounds of Formula I is then produced by the substitution of the hydrogen on the hydroxy group by an alkyl or halide.

Those compounds of Formula I in which "A" equals —N($R^{11}$)— are prepared in essentially the same manner as the substituted benzofurans described supra. Example 33, infra, provides one such protocol for synthesizing the substituted indoles of this invention.

Those compounds of Formula I in which "A" equals —S(O)$_m$— are prepared in essentially the same manner as the substituted benzofurans described supra. The examples infra provide several exemplifications of these benzothiophenes and the oxidated derivatives thereof.

Those compounds of Formula I in which m is one or two may be prepared by oxidation of the corresponding benzothiophene in which m is zero. Oxidation may be carried out by treating the benzothiophene with an oxidizing agent, for example, m-chloroperbenzoic acid, or the like, for a time sufficient to achieve formation of the sulfoxide group. The progress of the oxidation reaction may be monitored by thin layer chromatography methods.

The compounds used in the methods of this invention form pharmaceutically acceptable acid and base addition salts with a wide variety of organic and inorganic acids and bases and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dicarboxylate, hexyne-1,4-dicarboxylate, caprate, caprylate, cinnamate, citrate, formate, fumarate, glycollate, heptanoate, hippurate, hydrochloride, lactate, malate, maleate, hydroxymaleate, malonate, mandelate, mesylate, nicotinate, isonicotinate, nitrate, oxalate, phthalate, teraphthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromobenzenesulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferable salt is the hydrochloride salt.

The pharmaceutically acceptable acid addition salts are typically formed by reacting a compound of Formula I with an equimolar or excess amount of acid. The reactants are generally combined in a mutual solvent such as diethyl ether or benzene. The salt normally precipitates out of solution within about one hour to 10 days and can be isolated by filtration or the solvent can be stripped off by conventional means.

Bases commonly used for formation of salts include ammonium hydroxide and alkali and alkaline earth metal hydroxides and carbonates, as well as aliphatic and aromatic amines, aliphatic diamines and hydroxy alkylamines. Bases especially useful in the preparation of addition salts include ammonium hydroxide, potassium carbonate, calcium hydroxide, methylamine, diethylamine, ethylene diamine, cyclohexylamine and ethanolamine.

The pharmaceutically acceptable salts frequently have enhanced solubility characteristics compared to the compound from which they are derived, and thus are often more amenable to formulation as liquids or emulsions.

EXAMPLES

The following experiments illustrate the preparation of the benzofurans, benzothiophenes and indoles employed in the present invention. The terms "NMR", "IR" or "MS" following a synthesis protocol indicates that the nuclear magnetic resonance spectrum, infrared spectrum, or the mass spectrometry was performed and was consistent with the title product.

Preparation 1a

Synthesis of 2-(3-methoxyphenoxy)-1-(4-methoxyphenyl)ethanone

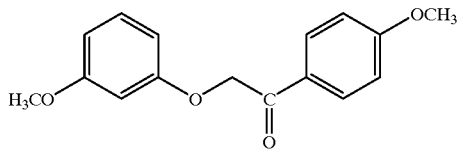

In a one liter round-bottom flask, fitted with a condenser and nitrogen inlet, were added 3-methoxyphenol (12.4 g, 0.1 mole), 4-methoxyphenacyl bromide (22.9 g, 0.1 mole), potassium carbonate (17.3 g, 0.125 mole) in 100 ml of 2-butanone. This mixture was heated to 80° C. and was maintained at this temperature for about four hours. The progress of the reaction was monitored by thin layer chromatography (silica gel, 9:1 toluene:ethyl acetate).

After the four hours at 80° C. the reaction mixture was cooled and the reaction mixture was partitioned by the addition of water. The organic phase was removed and the aqueous layer was washed with 2-butanone. The organic layers were then combined, dried over magnesium sulfate, and the solvents were removed in vacuo to yield 31.1 grams of a yellow oil. The yellow oil was further purified by chromatography, the fractions containing the desired product were then crystallized. All of the crystalline fractions were combined and then dissolved in 80 ml of hot ethanol. Fifteen milliliters of hot water was then added, the product was crystallized, and subsequently washed with an ethanol/water mixture to yield 19.1 g (70%) of the desired title product. mp 52.5°–53.5° C.

Analysis for $C_{16}H_{16}O_4$: Theory: C, 68.08; H, 5.71; N, 2.84. Found: C, 67.86; H, 5.51; N, 2.88.

Preparation 2a

Synthesis of 2-methoxyphenyl-6-methoxybenzofuran

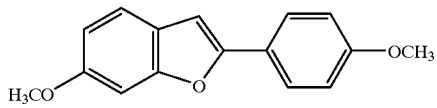

The cyclization of the product of Preparation 1a was performed essentially as described in C. Goldenberg, et al., *Chimie Therapeutique*, 398–411 (1973). In a 500 ml 3-neck round bottom flask polyphosphoric acid (30 g) was added to 200 ml of xylene. The mixture was then heated to about 120° C. To this heated mixture was then added 2-(3-methoxyphenoxy)-1-(4-methoxyphenyl)ethanone (10 g, 0.037 mole), prepared as described supra, and the temperature was raised to about 170° C., and maintained at that temperature for about eight hours. The reaction mixture was then cooled and water was added.

The dark aqueous layer was separated from the yellow organic phase. The organics were washed with water and by aqueous sodium carbonate, and then dried over anhydrous magnesium sulfate. The solvents were removed in vacuo, resulting in a yellow-orange solid. The product was recrystallized from a minimum of hot acetone, followed by the addition of ethanol and water. The residual acetone was removed by boiling. Cooling to room temperature yielded white crystals (2.09 g, 22% yield). mp 158° C.

Analysis for $C_{16}H_{14}O_3$: Theory: C, 75.58; H, 5.55; O, 18.88. Found: C, 75.33; H, 5.67; O, 18.62.

Preparation 3a

Synthesis of 2-(4-methoxyphenyl)-3-(4-methoxybenzoyl)-6-methoxybenzofuran

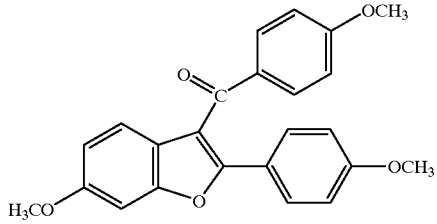

In a 250 ml 3-neck round bottom flask were added 2-hydroxy-4-methoxybenzaldehyde (10 g, 65.7 mmol), 1-(4-methoxyphenyl)-2-(4-methoxyphenyl)ethanone (16 g, 62.6 mmol), ethyl acetate (100 ml) and ethanol (25 ml). The reaction mixture was then warmed to about 45° C. until all the starting materials were dissolved. Hydrogen chloride gas was then bubbled in for about 30 minutes, resulting in the formation of a bright red coloration. The reaction was then allowed to stand at room temperature for about two hours at which time the solvents were removed in vacuo to leave a bright red oil.

The red oil was dissolved in 180 ml of methanol and 30 ml of 20% sulfuric acid was added with stirring and cooling. Hydrogen peroxide (30 ml) was added dropwise and the mixture was allowed to stir for about 30 minutes. A saturated sodium chloride solution (500 ml) and ethyl acetate (300 ml) were added to the reaction mixture and the organic fraction was removed. The organic layer was washed with a saturated sodium chloride solution, dried, and the solvents were removed in vacuo to provide 25 g of a reddish brown oil which was further purified by chromatography to yield the title product (1.25 g) as a yellow oil. mp 106–109° C.

Analysis for $C_{24}H_{20}O_5$: Theory: C, 74.21; H, 5.19; O, 20.60. Found: C, 74.07; H, 5.22; O, 20.38.

Preparation 4a

Synthesis of 2-(4-methoxyphenyl)-3-(4-hydroxybenzoyl)-6-methoxybenzofuran

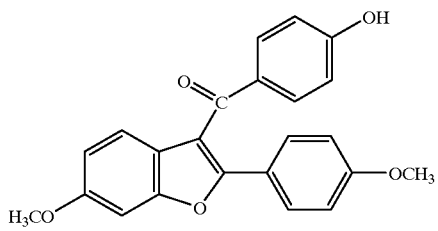

In a three-neck round bottom flask under a nitrogen atmosphere and cooled in an ice bath, ethanethiol (0.95 ml, 1.288 mmol) was dissolved in 10 ml of anhydrous N,N-dimethylformamide. To this solution was added n-butyllithium (0.60 ml of a 1.6 M in hexane solution, 0.966 mmole) followed by the addition of 2-(4-methoxyphenyl)-3-(4-methoxybenzoyl)-6-methoxybenzofuran (250 mg, 0.644 mmole), prepared as described in Preparation 3, supra. The reaction mixture was then heated to 80° C. and allowed to remain at that tempeature for about 16 hours.

The reaction mixture was then poured into 1 N hydrochloric acid and extracted with ethyl acetate. The organic layer was then washed with a saturated sodium chloride solution, dried over magnesium sulfate, filtered and the solvents were removed in vacuo. The desired product was further purified by column chromatography. The product was then crystallized from methanol yielding 130 mg (81%) of the desired product. mp 148–149° C.

Analysis for $C_{23}H_{18}O_5$:

Theory: C, 73.79; H, 4.85; O, 21.37.

Found: C, 73.68; H, 5.12; O, 21.17.

Example 18

Synthesis of 2-(4-methoxyphenyl)-3-[4-[2-(piperidin-1-yl)ethoxy]benzoyl]-6-methoxybenzofuran

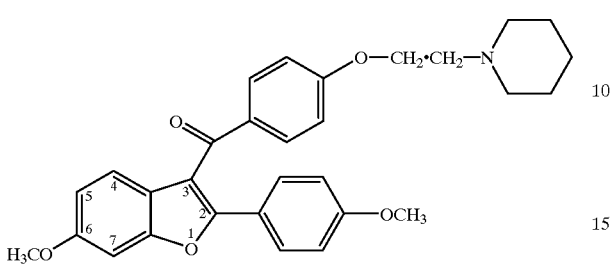

Method A: Acylation of Benzofuran

4-[2-(Piperidin-1-yl)ethoxy]benzoyl chloride (0.562 g, 1.96 mmol) was added to ethylene chloride (20 ml), followed by the addition of 2-methoxyphenyl-6-methoxybenzofuran (0.500 g, 1.96 mmol), prepared as described in Preparation 2a, supra. This mixture was stirred at room temperature as aluminum trichloride (1.96 g, 14.7 mmol) was added. This reaction mixture was then stirred overnight.

The reaction mixture was then poured over ice, and extracted with warm chloroform (3×50 ml). The chloroform was removed by evaporation. Sodium carbonate, water and ethyl acetate were then added and the organic layer was removed, dried over magnesium sulfate, and the solvents were removed in vacuo to provide a yellow oil. The desired product was further purified by chromatography of the yellow oil to yield the desired title product. NMR, IR, MS.

Analysis for $C_{30}H_{31}NO_5$: Theory: C, 74.21; H, 6.44; N, 2.88; O, 16.47. Found: C, 74.11; H, 6.71; N, 2.75; O, 16.57.

Method B: Alkylation of 2-(4-methoxyphenyl)-3-(4-hydroxybenzoyl)-6-methoxybenzofuran.

In 100 ml of anhydrous N,N-dimethylformamide in a 500 ml round bottom flask were added 2-(4-methoxyphenyl)-3-(4-hydroxybenzoyl)-6-methoxybenzofuran (10.50 g, 28 mmol), prepared as described in Preparation 4a, supra, and potassium carbonate (6.20 g, 34 mmol). This mixture was heated to 100° C. and then 2-(piperidin-1-yl)ethyl chloride (6.20 g, 34 mmol) was added gradually. The reaction mixture was kept at 100° C. for about one hour.

The N,N-dimethylformamide was evaporated and the residue was dissolved in ethyl acetate and water. The ethyl acetate layer was removed and the aqueous layer was washed with more ethyl acetate. The organic fractions were combined, dried over magnesium sulfate, and the solvents were removed in vacuo, yielding 13.3 g of a yellow oil which crystallized upon standing. The product was recrystallized from methanol cooled to −30° C. prior to filtration, yielding 11.4 g (84%) of the desired product as pale yellow crystals. mp 87–89° C.

Analysis for $C_{30}H_{31}NO_5$: Theory: C, 74.21; H, 6.44; N, 2.88; O, 16.47. Found: C, 74.31; H, 6.34; N, 2.63; O, 16.47.

Example 19

Synthesis of 2-(4-hydroxyphenyl)-3-[4-[2-(piperidin-1-yl)ethoxy]benzoyl]-6-hydroxybenzofuran

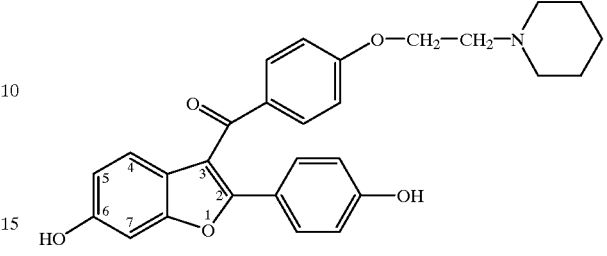

The title product was prepared by the demethylation of 2-(4-methoxyphenyl)-3-[4-[2-(piperidin-1-yl)ethoxy]benzoyl]-6-methoxybenzofuran, the product of Example 1a, supra. In a 250 ml three-neck round bottom flask were combined ethylene chloride (50 ml) and aluminum trichloride (9.60 g, 72 mmol) and ethanethiol (6.39 g, 103 mmol) to create a pale yellow liquid. To this liquid was then added the product of Example 1a (5.00 g, 10.3 mmol) in a gradual fashion. A red oil precipitated and the mixture was stirred for about 20 minutes. After cooling the reaction mixture in an ice bath 100 ml of tetrahydrofuran was added and the mixture was allowed to stir until all of the oil had gone into solution.

The reaction mixture was then poured over ice (200 ml) and water (500 ml) and concentrated hydrochloric acid (10 ml) were added. The oil which precipitated was separated from the liquid by decantation. The liquid was extracted with chloroform (warm, 2×300 ml). The oil was dissolved by mixing with ethyl acetate, chloroform, sodium bicarbonate, and a small amount of sodium hydroxide. The chloroform extract and the dissolved oil were transferred to separatory funnel and washed with sodium bicarbonate. The organic phase was then dried over magnesium sulfate and the solvents were removed by evaporation to yield a yellow foam, which was further purified by high performance liquid chromatography.

NMR, IR, MS.

Analysis for $C_{28}H_{27}NO_5$: Theory: C, 73.51; H, 5.95; N, 3.06. Found: C, 70.45; H, 6.34; N, 4.02.

Example 20

Synthesis of 2-(4-methoxyphenyl)-3-[4-[2-(pyrrolidin-1-yl)ethoxy]benzoyl]-6-methoxybenzofuran hydrochloride

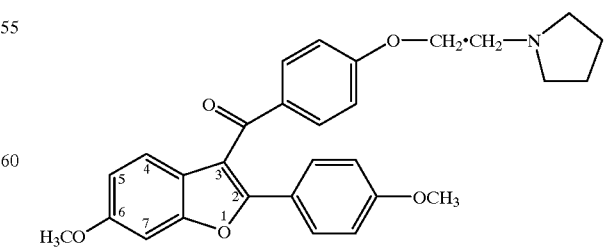

The title compound is prepared essentially as described in the process for preparing the compound of Example 18 except that 4-[2-(pyrrolidin-1-yl)ethoxy]benzoyl chloride is employed in the synthesis of Method A in place of 4-[2-(piperidin-1-yl)ethoxy]benzoyl chloride or 2-(pyrrolidin-1-yl)ethyl chloride is employed in the synthesis of Method B in place of the 2-(piperidin-1-yl)ethyl chloride.

Example 21

Synthesis of 2-(4-hydroxyphenyl)-3-[4-[2-(pyrrolidin-1-yl)ethoxy]benzoyl]-6-hydroxybenzofuran hydrochloride

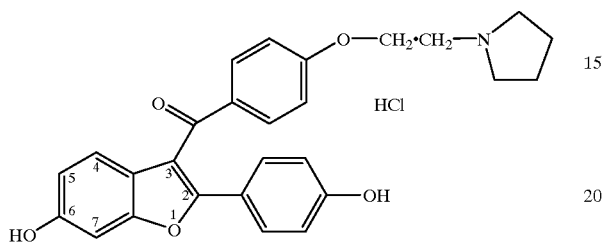

The title compound is prepared essentially as described in Example 19 except that 2-(4-methoxyphenyl)-3-[4-[2-(pyrrolidin-1-yl)ethoxy]benzoyl]-6-methoxybenzofuran is used as the starting material instead of 2-(4-methoxyphenyl)-3-[4-[2-(piperidin-1-yl)ethoxy]benzoyl]-6-methoxybenzofuran.

NMR, IR, MS.

Analysis for $C_{27}H_{26}NO_5Cl$: Theory: C, 67.57; H, 5.46; N, 2.92. Found: C, 67.84; H, 5.56; N, 2.87.

Example 22

Synthesis of 2-(4-methoxyphenyl)-3-[4-[2-(diethylamino)ethoxy]benzoyl]-6-methoxybenzofuran

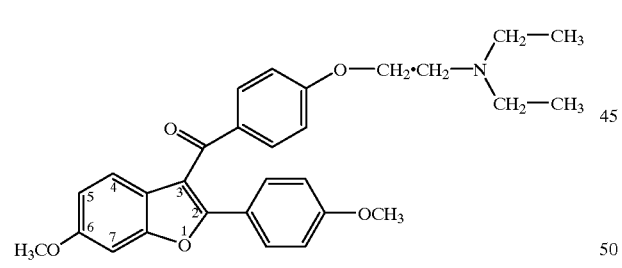

The title compound was prepared by reacting the compound of Preparation 4a supra, 2-(4-methoxyphenyl)-3-(4-hydroxybenzoyl)-6-methoxybenzofuran (10 g, 26.7 mmol) which is dissolved in 200 ml of N,N-dimethylformamide with an equimolar amount of 2-(N,N-diethylamino)ethyl chloride (6.4 g, 32 mmol) and potassium carbonate (11.06 g, 80.2 mmol). The mixture was heated to 100° C. and was maintained at that temperature for about two hours. The reaction mixture was then cooled to room temperature and maintained at this temperature overnight while stirring.

The solvents were then removed by evaporation and the residue was extracted from water with ethyl acetate and washed twice with a saturated sodium chloride solution. The organic phase was dried over sodium sufate and the solvents were removed in vacuo. The material was crystallized from hexane and recrystallized in methanol.

NMR, IR, MS.

Analysis for $C_{29}H_{31}NO_5$: Theory: C, 73.55; H, 6.60; N, 2.96. Found: C, 73.29; H, 6.50; N, 2.84.

Example 23

Synthesis of 2-(4-hydroxyphenyl)-3-[4-[2-(diethylamino)ethoxy]benzoyl]-6-hydroxybenzofuran hydrochloride

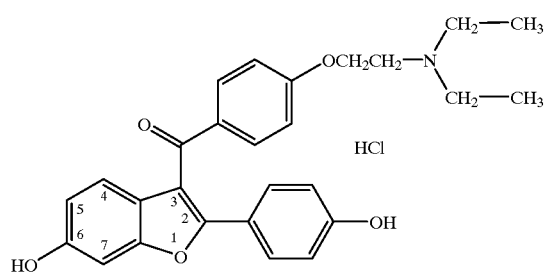

The title compound was prepared essentially as described in Example 19, supra, except that the compound of Example 5, 2-(4-methoxyphenyl)-3-[4-[2-(diethylamino)ethoxy]benzoyl]-6-methoxybenzofuran, was used as the starting material to be demethylated.

NMR, IR, MS.

Analysis for $C_{27}H_{28}NO_5Cl$: Theory: C, 67.29; H, 5.86; N, 2.91. Found: C, 67.54; H, 5.64; N, 2.92.

Example 24

Synthesis of 2-(4-methoxyphenyl)-3-[4-[2-(diisopropylamino)ethoxy]benzoyl]-6-methoxybenzofuran

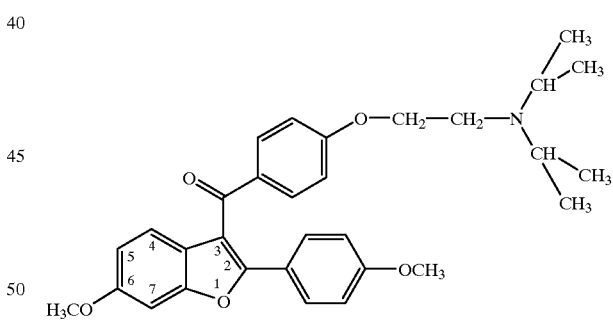

The title compound was prepared by reacting the compound of Preparation 4a supra, 2-(4-methoxyphenyl)-3-(4-hydroxybenzoyl)-6-methoxybenzofuran (10 g, 26.7 mmol) which is dissolved in 200 ml of N,N-dimethylformamide with 2-(N,N-diisopropylamino)ethyl chloride (6.4 g, 32 mmol) and potassium carbonate (11.06 g, 80.2 mmol). The mixture was heated to 100° C. and was maintained at that temperature for about two hours. The reaction mixture was then cooled to room temperature and maintained at this temperature overnight while stirring.

The solvents were then removed by evaporation and the residue was extracted from water with ethyl acetate and washed twice with a saturated sodium chloride solution. The organic phase was dried over sodium sufate and the solvents were removed in vacuo. The material was crystallized from hexane and recrystallized in methanol.

NMR, IR, MS.

Analysis for $C_{33}H_{39}NO_5$: Theory: C, 74.83; H, 7.42; N, 2.64. Found: C, 74.68; H, 7.14; N, 2.76.

Example 25

Synthesis of 2-(4-hydroxyphenyl)-3-[4-[2-(diisopropylamino)ethoxy]benzoyl]-6-hydroxybenzofuran hydrochloride

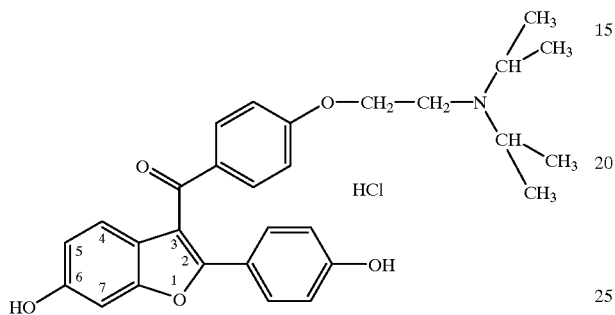

The title compound was prepared essentially as described in Example 19, supra, except that the compound of Example 24, 2-(4-methoxyphenyl)-3-[4-[2-(diisopropylamino)ethoxy]benzoyl]-6-methoxybenzofuran, was used as the starting material to be demethylated.

NMR, IR, MS.

Analysis for $C_{29}H_{32}NO_5Cl$: Theory: C, 68.29; H, 6.32; N, 2.75. Found: C, 68.53; H, 6.49; N, 2.74.

Example 26

Synthesis of 2-(4-methoxyphenyl)-3-[4-[2-(dimethylamino)ethoxy]benzoyl]-6-methoxybenzofuran

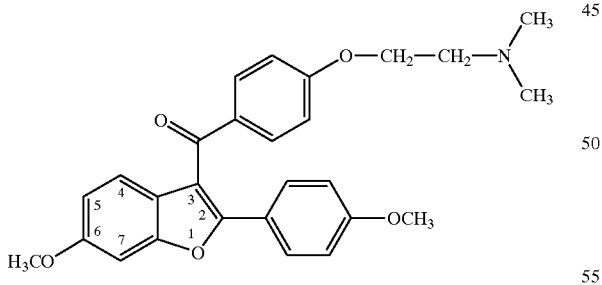

The title compound was prepared essentially as described in Example 24, supra, except that 2-(N,N-dimethylamino) ethyl chloride was reacted with 2-(4-methoxyphenyl)-3-(4-hydroxybenzoyl)-6-methoxybenzofuran instead of the 2-(N,N-diisopropylamino)ethyl chloride employed in that example.

NMR, IR, MS.

Analysis for $C_{27}H_{27}NO_5$: Theory: C, 72.79; H, 6.11; N, 3.14. Found: C, 72.51; H, 6.27; N, 3.10.

Example 27

Synthesis of 2-(4-hydroxyphenyl)-3-[4-[2-(dimethylamino)ethoxy]benzoyl]-6-hydroxybenzofuran

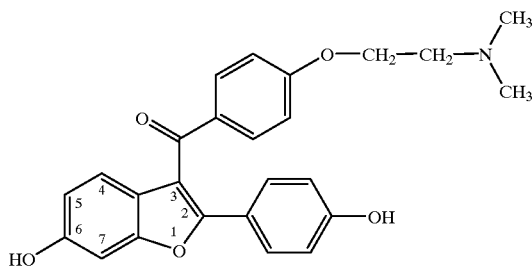

The title compound was prepared essentially as described in Example 19, supra, except that the compound of Example 26, 2-(4-methoxyphenyl)-3-[4-[2-(dimethylamino)ethoxy] benzoyl]-6-methoxybenzofuran, was used as the starting material to be demethylated.

NMR, IR, MS.

Analysis for $C_{25}H_{23}NO_5$: Theory: C, 71.93; H, 5.55; N, 3.36. Found: C, 70.69; H, 5.51; N, 3.16.

Example 28

Synthesis of 2-(4-methoxyphenyl)-3-[4-[2-(hexamethyleneimin-1-yl)ethoxy]benzoyl]-6-methoxybenzofuran

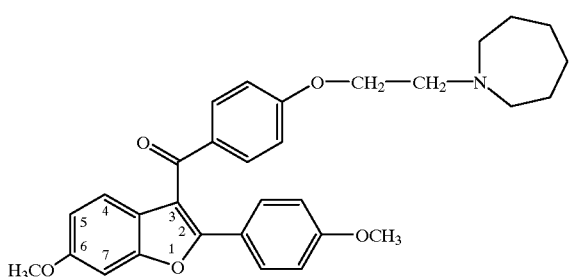

The title compound was prepared essentially as described in Example 24, supra, except that 2-(hexamethyleneimin-1-yl)ethyl chloride was reacted with 2-(4-methoxyphenyl)-3-(4-hydroxybenzoyl)-6-methoxybenzofuran instead of the 2-(N,N-diisopropylamino)ethyl chloride employed in that example.

NMR, IR, MS.

Analysis for $C_{31}H_{33}NO_5$: Theory: C, 74.53; H, 6.66; N, 2.80. Found: C, 74.69; H, 6.70; N, 2.75.

Example 29

Synthesis of 2-(4-hydroxyphenyl)-3-[4-[2-(hexamethyleneimin-1-yl)ethoxy]benzoyl]-6-hydroxybenzofuran hydrochloride

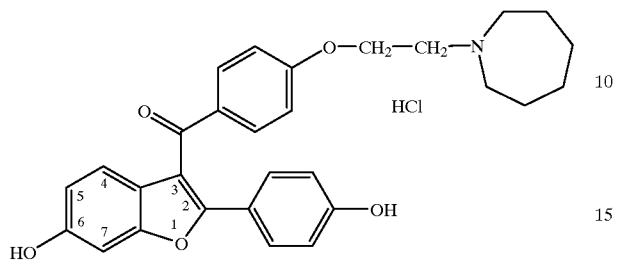

The title compound was prepared essentially as described in Example 19, supra, except that the compound of Example 28, 2-(4-methoxyphenyl)-3-[4-[2-(hexamethyleneimin-1-yl)ethoxy]benzoyl]-6-methoxybenzofuran, was used as the starting material to be demethylated.

NMR, IR, MS

Analysis for $C_{29}H_{30}ClNO_5$: Theory: C, 68.57; H, 5.95; N, 2.76. Found: C, 67.28; H, 6.13; N, 2.66.

Example 30

Synthesis of 2-(4-hydroxyphenyl)-3-[4-[2-(piperidin-1-yl)ethoxy]benzoyl]-6-hydroxybenzofuran hydrochloride

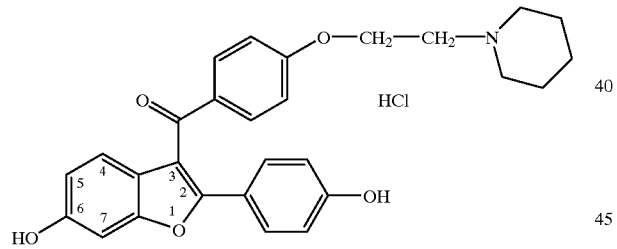

The title compound was prepared by dissolving the compound of Example 19, 2-(4-hydroxyphenyl)-3-[4-[2-(piperidin-1-yl)ethoxy]benzoyl]-6-hydroxybenzofuran, (3.1 g, 6.8 mmol) in 15 ml of methanol and treating with an excess of 3% hydrochloric acid in methanol. The volume was then reduced by boiling to 15 ml. Warm water (20 ml) was then added and the reaction mixture was further warmed to clarify. The reaction mixture was then filtered, followed by gradual cooling to 0° C., at which temperature the mixture was maintained for about one hour. The crystals, which had precipitated, were collected by filtration and washed with cold water. The pale yellow crystals were dried overnight, resulting in 2.82 g (84%) of the desired title product. mp 213–215° C.

NMR, IR, MS.

Analysis for $C_{28}H_{28}NO_5Cl$: Theory: C, 68.08; H, 5.71; N, 2.84; O, 16.19. Found: C, 67.86; H, 5.51; N, 2.88; O, 15.93.

Example 31

Synthesis of 2-(4-hydroxyphenyl)-3-[4-[2-(piperidin-1-yl)ethoxy]benzoyl]benzofuran hydrochloride

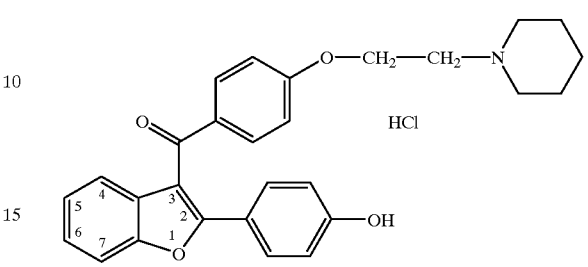

The 2-(4-hydroxyphenyl)-3-[4-[2-(piperidin-1-yl)ethoxy]benzoyl]benzofuran was prepared essentially as described in Example 19, except that phenol was used as a starting material in the synthesis described in Preparation 2a instead of 3-methoxy phenol. The hydrochloride salt of this substituted benzofuran was prepared essentially as described in Example 30, supra.

NMR, IR, MS.

Analysis for $C_{28}H_{28}NO_4Cl$: Theory: C, 70.36; H, 5.91; N, 2.93. Found: C, 70.46; H, 5.84; N, 2.84.

Example 32

Synthesis of 2-phenyl-3-[4-[2-(piperidin-1-yl)ethoxy]benzoyl]-6-hydroxybenzofuran hydrochloride

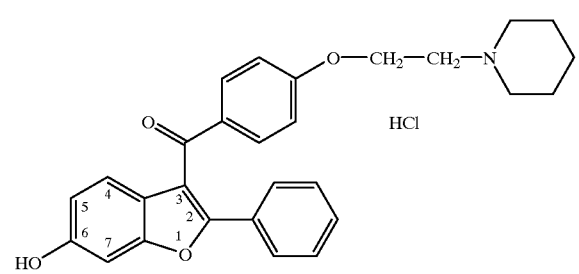

The 2-phenyl-3-[4-[2-(piperidin-1-yl)ethoxy]benzoyl]-6-hydroxybenzofuran was prepared essentially as described in Example 19, except that phenacylbromide (also known as α-bromoacetophenone) was used as a starting material in the synthesis described in Preparation 1a instead of 4-methoxyphenacylbromide. The hydrochloride salt of this substituted benzofuran was prepared essentially as described in Example 30, supra.

NMR, IR, MS.

Analysis for $C_{28}H_{28}NO_4Cl$: Theory: C, 70.36; H, 5.90; N, 2.93. Found: C, 70.39; H, 6.01; N, 2.91.

Example 33

Synthesis of 1-ethyl-2-(4-methoxyphenyl)-3-[4-[2-(piperidin-1-yl)ethoxy]benzoyl]-6-hydroxyindole hydrochloride salt

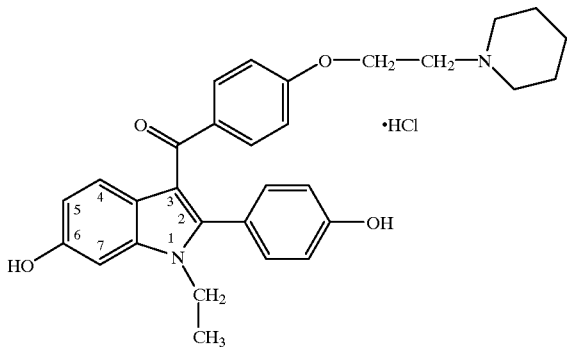

To 814 milliliters of concentrated hydrochloric acid in a 3 liter, 3-neck round bottom flask which had been cooled to 0° C. was added 3-methoxyaniline (99.26 g, 0.806 mole). Sodium nitrate (55.61 g, 0.806 mole), dissolved in 249 milliliters of water, was added dropwise to the 3-methoxyaniline solution at such a rate that the reaction temperature never exceeded 0° C. This mixture was then stirred for about 90 minutes.

Stannous chloride (545.57 g, 2.418 mol), dissolved in 497 milliliters of concentrated hydrochloric acid, was added dropwise to the reaction mixture at such a rate that the reaction temperature never exceeded 5° C. This mixture was then stirred for about two hours after the addition of the stannous chloride was completed, resulting in the formation of a thick, beige, chalky emulsion. The solid was removed by filtration, stored overnight in one liter of water and then basified with a 25% solution of sodium hydroxide. This aqueous solution was extracted with diethyl ether (3×1 liter) and then dried over sodium sulfate. The solvents were removed in vacuo, resulting in a brown oil of 3-methoxyphenylhydrazine (76.3 g, 69% yield).

The 3-methoxyphenylhydrazine (76.3 g, 0.552 mole) prepared supra, was dissolved in 400 milliliters of ethanol. To this mixture was added p-methoxyacetophenone (82.80 g, 0.552 mole) followed by the addition of about 6 drops of hydrochloric acid. This mixture was then stirred for about seven hours under a nitrogen atmosphere, followed by storage at 4° C. for about 3 days.

The white solid was then removed from the suspension by filtration under vacuum and then dried in vacuo, resulting in 135.2 grams (91% yield) of [(3-methoxyphenyl)hydrazono]-1-methyl-4-methoxybenzylidene of the following formula as a pale gray solid.

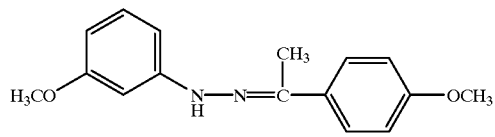

Zinc chloride (66.5 g, 0.49 mole) was added to a 3-neck round bottom flask under a nitrogen atmosphere. The flask and its contents were then heated to 200° C. at which time the hydrazone (26.4 g, 0.098 mole) prepared supra was added. The mixture was stirred for about 17 minutes, resulting in the formation of a brown tar and the evolution of some gas. The brown tar was then poured into two liters of 0.075 N hydrochloric acid and this mixture was stirred for about 48 hours, resulting in the formation of a yellow solid.

The solids were removed by filtration and were then recrystallized from methanol. The solids were again removed by filtration and the solvents were removed in vacuo to yield the desired 2-(4-methoxyphenyl)-6-methoxyindole (5.50 g, 22% yield) as a white crystalline product.

The 2-(4-methoxyphenyl)-6-methoxyindole (2.0 g, 8 mmol) was dissolved in 40 milliliters of N,N-dimethylformamide. This solution was added dropwise to a solution of sodium hydride (0.48 g, 12 mmol) in ten milliliters of N,N-dimethylformamide. This reaction mixture was then stirred at room temperature for 1 hour at which time a solution of ethyl iodide (1.9 g, 12 mmol) in N,N-dimethylformamide (10 ml) was added dropwise over five minutes. This mixture was then stirred at room temperature for about two hours.

The reaction was quenched by the addition of methanol. The volume of the solvents was reduced by vacuum, leaving a brown oil. This oil was diluted with chloroform, washed with 5 N sodium hydroxide (3×75 ml), followed by washing with water (2×200 ml). The organic layer was dried over sodium sulfate and the solvents were removed in vacuo leaving 2.3 g of the desired intermediate 1-ethyl-2-(4-methoxyphenyl)-6-methoxyindole as white crystals.

The preceding intermediate was acylated at the 3-position by first placing N,N-dimethyl-4-methoxybenzamide (1.43 g, 8 mmol), in a 100 ml flask cooled to 0° C. To this was then added phosphorous oxychloride (6.1 g, 40 mmol) dropwise at such a rate that the reaction temperature never exceeded 20° C. The reaction mixture was allowed to warm to room temperature and was stirred for about 30 minutes. The reaction mixture was then cooled to 0° C. and the 1-ethyl-2-(4-methoxyphenyl)-6-methoxyindole (1.5 g, 5.33 mmol) prepared supra, was added and the reaction mixture was then heated to 75° C. and maintained at this temperature for about three hours.

After this incubation, the reaction mixture was poured over ice and diluted with water. The layers were separated and the organic phase was washed with water (150 ml). The organic layer was dried over sodium sulfate and the oslvents were removed in vacuo to yield a dark brown/black oil. This oil was taken up in 50 milliliters of methanol and cooled to 0° C. This solution was then basified by the dropwise addition of 2N sodium hydroxide (50 ml). The mixture was then heated to reflux for about 5 minutes, then cooled overnight at 4° C.

The precipitate was then removed by filtration and recrystallized from methanol, resulting in 2.21 grams (86% yield) of the intermediate 1-ethyl-2-(4-methoxyphenyl)-3-(4-methoxybenzoyl)-6-methoxyindole as a yellow precipitate.

The above intermediate (2.1 g, 5.05 mmol) was then admixed with sodium thioethoxide (0.85 g, 10.11 mmol) in N,N-dimethylformamide (12 ml). The reaction mixture was then heated to 85° C. and maintained at this temperature for about six hours. The desired intermediate 1-ethyl-2-(4-methoxyphenyl)-3-(4-hydroxybenzoyl)-6-methoxyindole was then recrystallized from ethyl acetate.

This intermediate (1.5 g, 3.74 mmol) was then reacted with 2-(piperidin-1-yl)ethyl chloride hydrochloride (1.38 g, 7.5 mmol) in N,N-dimethylformamide (60 ml) in the presence of cesium carbonate (3.26 g, 10 mmol). This admixture was heated to 80° C. and maintained at this temperature for about two hours.

The precipitate was collected by filtration and then taken up in chloroform, and washed with 2 N sodium hydroxide (3×125 ml) and water (3×100 ml). The organic fraction was then dried over sodium sulfate and the solvents were removed in vacuo to yield 2.05 grams (95% yield) of 1-ethyl-2-(4-methoxyphenyl)-3-[4-[2-(piperidin-1-yl)ethoxy]benzoyl]-6-methoxyindole as a gray foam.

This intermediate (1.0 g, 1.82 mmol) was dissolved in dichloromethane (10 ml) and cooled to 0° C. To this mixture was then added the Lewis acid aluminum chloride (1.2 g, 9 mmol) and the reaction mixture was then stirred for five minutes. Ethanol (3 ml) were then added and the reaction mixture was stirred on ice for about 15 minutes. The temperature of the reaction mixture was slowly raised to reflux and maintained at reflux for about 1.5 hours.

The reaction mixture was then cooled to 0° C. and this temperature was maintained as tetrahydrofuran (5 ml) was added. To this mixture was then added 20% hydrochloric acid in water (5 ml) and the reaction mixture was cooled back to 0° C. at which time five milliliters of water was then added, resulting in the formation of a yellow gum. This suspension was then placed at −40° C. and kept at this temperature for about 48 hours, after which time a grayish material was removed from the mixture by filtration. Thin layer chromatography confirmed this precipitate as the desired title product.

NMR, MS.

Analysis for $C_{30}H_{33}ClN_2O_4$: Theory: C, 69.15; H, 6.38; N, 5.38. Found: C, 69.09; H, 6.43; N. 5.53.

Example 34

Synthesis of 2-(4-hydroxyphenyl)-3-[4-[3-(piperidin-1-yl)propoxy]benzoyl]-6-hydroxybenzo[b]thiophene hydrochloride

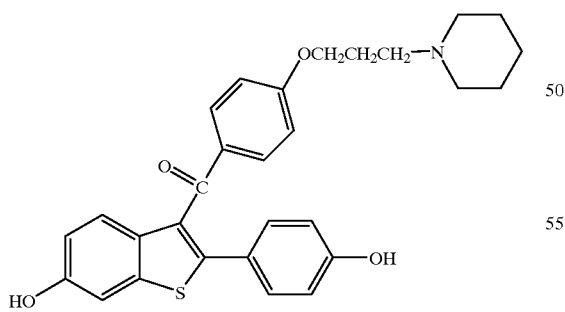

The title compound was prepared essentially as described in U.S. Pat. No. 4,380,635, which is herein incorporated by reference with the exception that 4-[3-(piperidin-1-yl)propoxy]benzoyl chloride was used to acylate the substituted benzo[b]thiophene rather than the 4-[2-(piperidin-1-yl)ethoxy]benzoyl chloride employed therein.

Example 35

Synthesis of 2-phenyl-3-[4-[2-(pyrrolidin-1-yl)ethoxy]benzoyl]benzo[b]thiophene

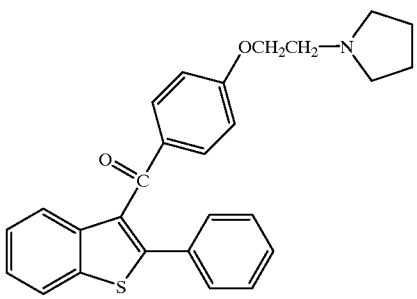

The title compound was prepared as described in U.S. Pat. No. 4,133,814, which is herein incorporated by reference.

Example 36

Synthesis of 2-phenyl-3-[4-[2-(pyrrolidin-1-yl)ethoxy]benzoyl]-6-methoxybenzo[b]thiophene citrate

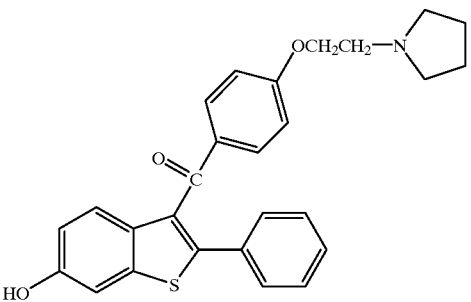

The title compound was prepared as described in U.S. Pat. No. 4,133,814, which is herein incorporated by reference.

Example 37

Synthesis of 2-(4-methoxyphenyl)-3-[4-[2-(pyrrolidin-1-yl)ethoxy]benzoyl]benzo[b]thiophene citrate

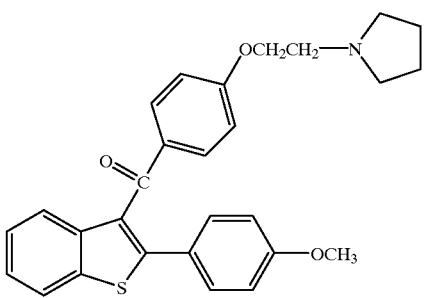

The title compound was prepared as described in U.S. Pat. No. 4,133,814, which is herein incorporated by reference.

Example 38

Synthesis of 2-(4-ethoxyphenyl)-3-[4-[2-(pyrrolidin-1-yl)ethoxy]benzoyl]-6-methoxybenzo[b]thiophene citrate

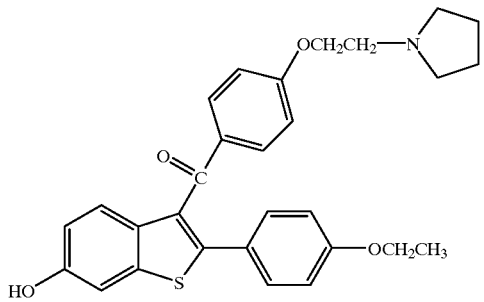

The title compound was prepared as described in U.S. Pat. No. 4,133,814, which is herein incorporated by reference.

Example 39

Synthesis of 2-(4-acetoxyphenyl)-3-[4-[2-(pyrrolidin-1-yl)ethoxy]benzoyl]benzo[b]thiophene citrate

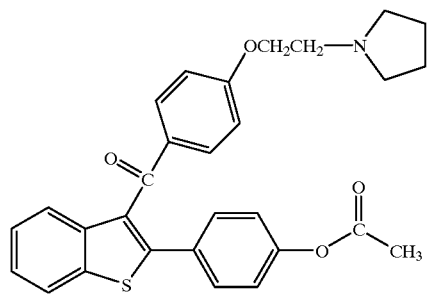

The title compound was prepared as described in U.S. Pat. No. 4,133,814, which is herein incorporated by reference.

Example 40

Synthesis of 2-phenyl-3-[4-[2-(piperidin-1-yl)ethoxy]benzoyl]benzo[b]thiophene

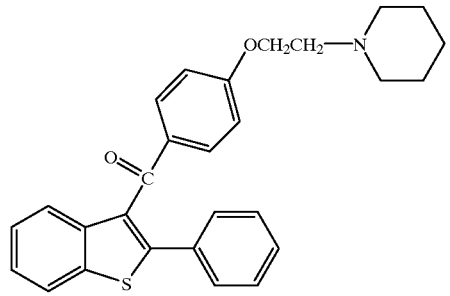

The title compound was prepared as described in U.S. Pat. No. 4,133,814, which is herein incorporated by reference.

Example 41

Synthesis of 2-phenyl-3-[4-[2-(piperidin-1-yl)ethoxy]benzoyl]-6-methoxybenzo[b]thiophene citrate

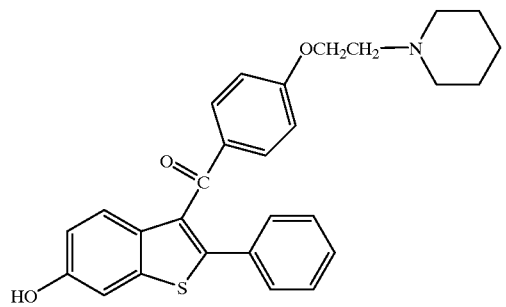

The title compound was prepared as described in U.S. Pat. No. 4,133,814, which is herein incorporated by reference.

Example 42

Synthesis of 2-(4-methoxyphenyl)-3-[4-[2-(piperidin-1-yl)ethoxy]benzoyl]benzo[b]thiophene citrate

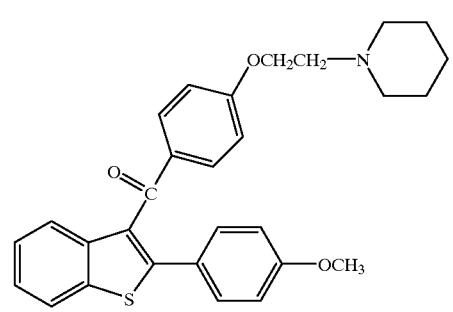

The title compound was prepared as described in U.S. Pat. No. 4,133,814, which is herein incorporated by reference.

Example 43

Synthesis of 2-(4-ethoxyphenyl)-3-[4-[2-(piperidin-1-yl)ethoxy]benzoyl]-6-methoxybenzo[b]thiophene citrate

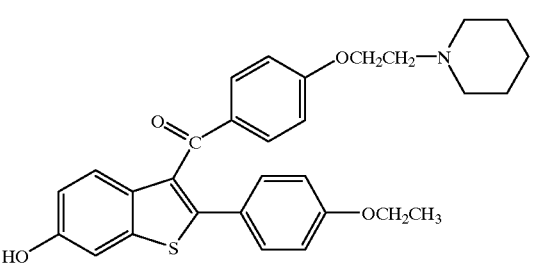

The title compound was prepared as described in U.S. Pat. No. 4,133,814, which is herein incorporated by reference.

Example 44

Synthesis of 2-(4-acetoxyphenyl)-3-[4-[2-(piperidin-1-yl)ethoxy]benzoyl]benzo[b]thiophene citrate

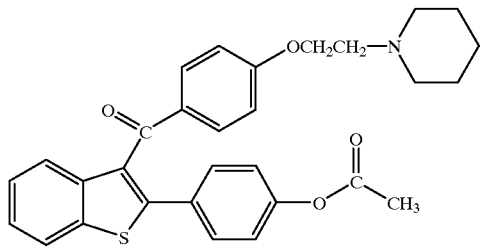

The title compound was prepared as described in U.S. Pat. No. 4,133,814, which is herein incorporated by reference.

Example 45

Synthesis of 2-(4-pentanoylphenyl)-3-[4-[2-(piperidin-1-yl)ethoxy]benzoyl]benzo[b]thiophene citrate

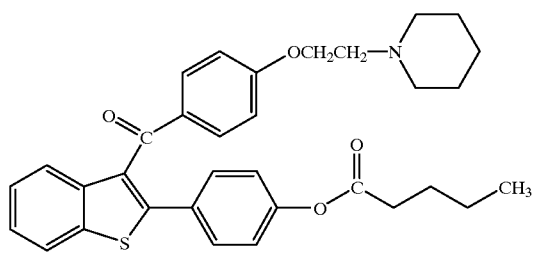

The title compound, also known as 2-(4-valerylphenyl)-3-[4-[2-(piperidin-1-yl)ethoxy]benzoyl]benzo[b]thiophene citrate, was prepared as described in U.S. Pat. No. 4,133,814, which is herein incorporated by reference.

Example 46

Synthesis of 2-(4-chlorophenyl)-3-[4-[2-(piperidin-1-yl)ethoxy]benzoyl]benzo[b]thiophene citrate

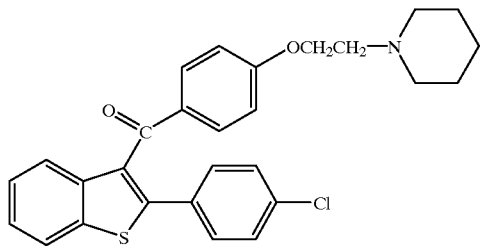

The title compound was prepared as described in U.S. Pat. No. 4,133,814, which is herein incorporated by reference.

Example 47

Synthesis of 2-phenyl-3-[4-[2-(hexamethyleneimin-1-yl)ethoxy]benzoyl]benzo[b]thiophene

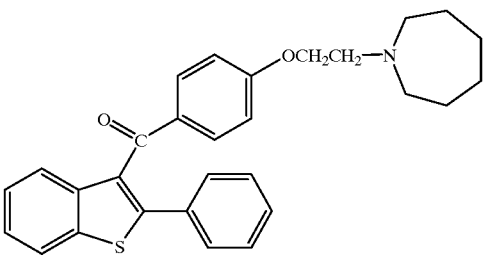

The title compound was prepared as described in U.S. Pat. No. 4,133,814, which is herein incorporated by reference.

Example 48

Synthesis of 2-phenyl-3-[4-[2-(hexamethyleneimin-1-yl)ethoxy]benzoyl]-6-methoxybenzo[b]thiophene citrate

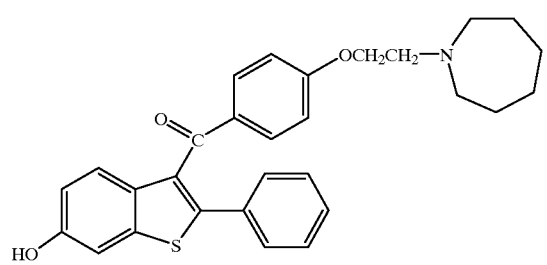

The title compound was prepared as described in U.S. Pat. No. 4,133,814, which is herein incorporated by reference.

Example 49

Synthesis of 2-(4-methoxyphenyl)-3-[4-[2-(hexamethyleneimin-1-yl)ethoxy]benzoyl]benzo[b]thiophene citrate The title compound was prepared as described in U.S. Pat. No. 4,133,814, which is herein incorporated by reference.

Example 50

Synthesis of 2-(4-ethoxyphenyl)-3-[4-[2-(hexamethyleneimin-1-yl)ethoxy]benzoyl]-6-methoxybenzo[b]thiophene citrate

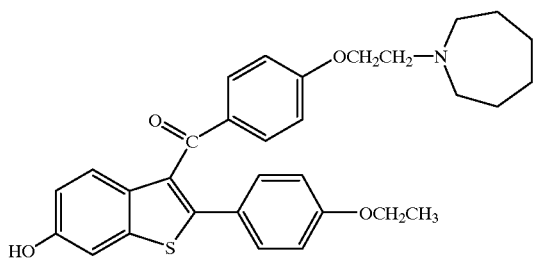

The title compound was prepared as described in U.S. Pat. No. 4,133,814, which is herein incorporated by reference.

Example 51

Synthesis of 2-(4-acetoxyphenyl)-3-[4-[2-(hexamethyleneimin-1-yl)ethoxy]benzoyl]benzo[b]thiophene citrate

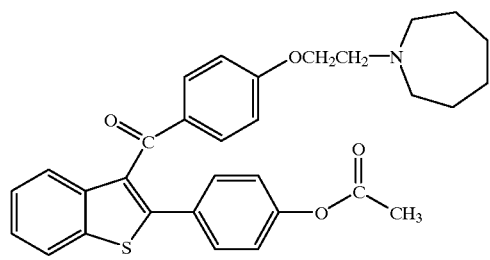

The title compound was prepared as described in U.S. Pat. No. 4,133,814, which is herein incorporated by reference.

Example 52

Synthesis of 2-(4-pentanoylphenyl)-3-[4-[2-(hexamethyleneimin-1-yl)ethoxy]benzoyl]benzo[b]thiophene citrate

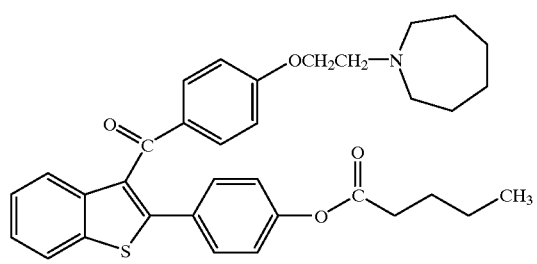

The title compound, also known as 2-(4-valerylphenyl)-3-[4-[2-(hexamethyleneimin-1-yl)ethoxy]benzoyl]benzo[b]thiophene citrate, was prepared as described in U.S. Pat. No. 4,133,814, which is herein incorporated by reference.

Example 53

Synthesis of 2-(4-chlorophenyl)-3-[4-[2-(hexamethyleneimin-1-yl)ethoxy]benzoyl]benzo[b]thiophene citrate

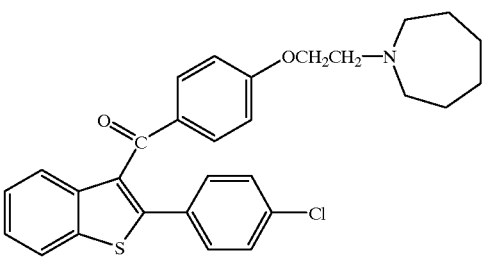

The title compound was prepared as described in U.S. Pat. No. 4,133,814, which is herein incorporated by reference.

Example 54

Synthesis of 2-(4-chlorophenyl)-3-[4-[2-(piperidin-1-yl)ethoxy]benzoyl]benzo[b]thiophene-1-oxide

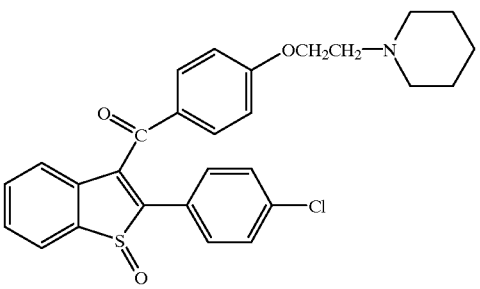

The title compound was prepared as described in U.S. Pat. No. 4,133,814, which is herein incorporated by reference.

Example 55

Synthesis of 2-(4-chlorophenyl)-3-[4-[2-(pyrrolidin-1-yl)ethoxy]benzoyl]benzo[b]thiophene-1-oxide

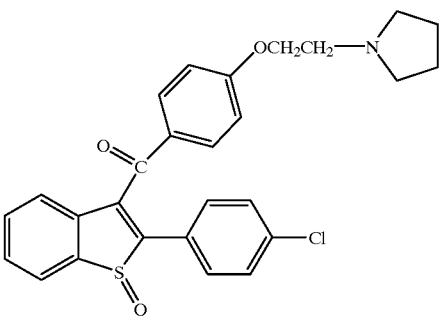

The title compound was prepared as described in U.S. Pat. No. 4,133,814, which is herein incorporated by reference.

Those compounds employed in the methods of the instant invention in which R or $R^1$ are $-OSO_2-(C_1-C_{10}$ alkyl)

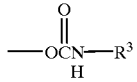

were made essentially as described in European Patent Application 617,030, published Sep. 28, 1994. Those compounds employed in the methods of the instant invention wherein at least one of $R^1$ and R is $-OSO_2-(C_1-C_{10}$ alkyl) were generally prepared by reacting a compound of Formula II

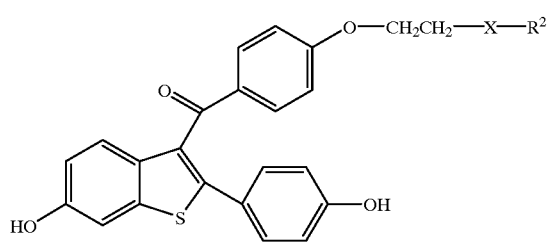

with an alkyl sulfonyl of Formula IIa

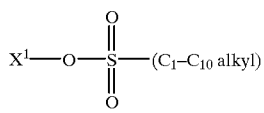

where $X^1$ is a leaving group, preferably a chloro or bromo group. This reaction is usually performed in a basic environment in the presence of a coupling catalyst such as 4-dimethylaminopyridine (DMAP). Most preferred solvents include the lower alkyl amines, especially triethylamine.

While this thioester formation reaction may be performed at equal molar ratios of the two reactants, it is usually preferred to employ a 2–3 molar excess of the alkyl sulfonyl compound so as to complete the reaction.

The following examples will illustrate preparation of these compounds of this invention but are not intended to limit it in any way.

Example 56

Preparation of [6-(n-butylsulfonoyl)-2-[4-(n-butylsulfonoyl)phenyl]benzo[b]thien-3-yl][4-[2-(1-piperidinyl)ethoxy]-phenyl] methanone

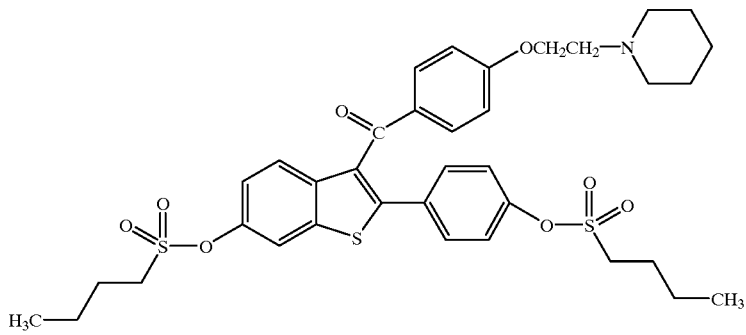

In dry tetrahydrofuran (250 ml) [6-hydroxy-2-(4-hydroxyphenyl)-benzo[b]thien-3-yl]-[4-[2-(1-piperidinyl) ethoxyphenyl]-methanone, hydrochloride (5.1 g, 10 mmol) was suspended and 7.1 g (70 mmol) of triethylamine was added. The reaction mixture was cooled to 0° C. in an ice bath and 10 mg of 4-dimethylaminopyridine (DMAP) was added, followed by the slow addition of n-butylsulfonyl chloride (4.7 g, 30 mmol). The reaction mixture was placed under a nitrogen atmosphere and allowed to warm slowly to room temperature and continued for 72 hours. The reaction mixture was filtered and evaporated to an oil. The oily residue was dissolved in chloroform and chromatographed on a silica gel column and eluted with a linear gradient of chloroform to chloroform-methanol (19:1; V:V). The desired fractions were combined and evaporated to dryness to afford 5.60 g of the title compound as a tan amorphous powder.

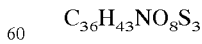

MS (FD) m/e=714 (M+1)

NMR was consistent with the proposed structure.

Example 57

Preparation of [6-(n-butylsulfonoyl)-2-[4-(n-butylsulfonoyl)phenyl]benzo[b]thien-3-yl][4-[2-(1-piperidinyl)ethoxy]-phenyl] methanone, Hydrochloride

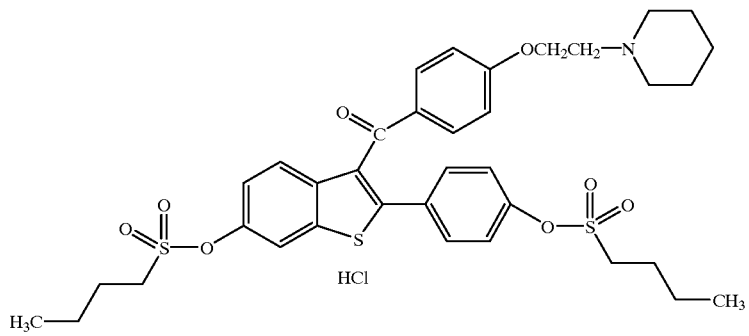

The commpound of Example 1, [6-(n-Butylsulfonoyl)-2-[4-(n-butylsulfonoyl)phenyl]-benzo[b]thien-3-yl][4-[2-(1-piperidinyl)ethoxy]-phenyl] methanone (5.4 g) was dissolved in ethyl acetate (EtOAc) and a solution of ether, saturated with hydrochloric acid, was added until no more precipitate was formed. The liquid was decanted off and the solid was triturated with ether. The title compound was crystallized from hot ethyl acetate to afford 3.74 g, as a white powder.

$C_{36}H_{43}NO_8S_3$-HCl

| Elemental Analysis: | C | H | N |
|---|---|---|---|
| Calculated: | 57.7 | 5.88 | 1.87 |
| Found: | 57.75 | 5.93 | 1.93 |

NMR was consistent with the proposed structure.

Example 58

Preparation of [6-(n-pentylsulfonoyl)-2-[4-(n-pentylsulfonoyl)phenyl]benzo[b]thien-3-yl][4-[2-(1-piperidinyl)ethoxy]-phenyl] methanone

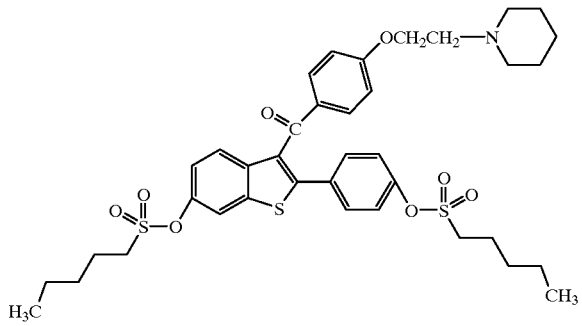

In dry tetrahydrofuran (100 ml) of [6-hydroxy-2-(4-hydroxyphenyl)-benzo[b]thien-3-yl]-[4-[2-(1-piperidinyl)ethoxy]phenyl-]methanone, hydrochloride (3 g, 5.9 mmol) was suspended and 10 mg of DMAP was added followed by 3 g (30 mmol) of triethylamine. The reaction mixture was stirred at room temperature and under a nitrogen blanket for about 20 minutes. n-Pentyl sulfonyl chloride (2.5 g, 14.7 mmol) was dissolved in 25 ml of tetrahydrofuran and slowly added to the stirring reaction mixture. The reaction was allowed to proceed at room temperature and under nitrogen for eighteen hours. The reaction mixture was filtered and the volatiles were removed in vacuo. The resulting material was dissolved in a small amount of chloroform and chromatographed (HPLC) on a silica gel column eluted with a linear gradient starting with chloroform and ending with chloroform-methanol (19:1 v/v). The desired fractions were determined by thin layer chromatography, combined and evaporated down to afford 3.82 g of the title compound as thick oil.

$C_{38}H_{47}NO_8S_3$

NMR: consistent with the proposed structure

MS: (FD) m/e=743 (M+2)

| Elemental Analysis: | C | H | N |
|---|---|---|---|
| Calculated: | 61.51 | 6.39 | 1.89 |
| Found: | 57.63 | 6.44 | 1.50 |

Example 59

Preparation of [6-(n-pentylsulfonoyl)-2-[4-(n-pentylsulfonoyl)phenyl]benzo[b]thien-3-yl][4-[2-(1-piperidinyl)ethoxy]-phenyl] methanone, Hydrochloride

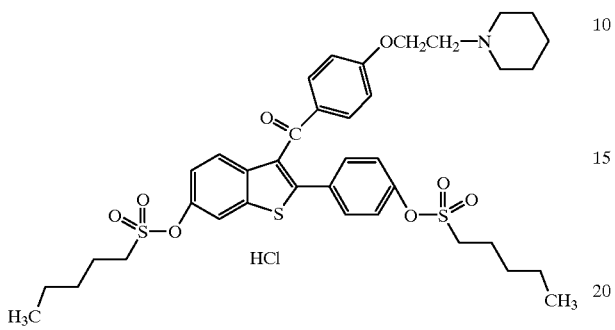

[6-(n-Pentylsulfonoyl)-2-[4-(n-pentylsulfonoyl)phenyl] benzo[b]thien-3-yl][4-[2-(1-piperidinyl)ethoxy]-phenyl] methanone (3.7 g) was dissolved in 25 ml of ethyl acetate and a solution of hydrochloric acid saturated diethyl ether was added. A precipitate formed and the liquid decanted off. The gummy solid was triturated with diethyl ether and dried in vacuo at room temperature to afford 2.12 g of the title compound as a white amorphous and hygroscopic solid.

NMR: consistent with the proposed structure

| Elemental Analysis: | C | H | N |
|---|---|---|---|
| Calculated: | 58.63 | 6.22 | 1.80 |
| Found: | 57.35 | 6.45 | 1.38 |

Example 60

Preparation of [6-(n-hexylsulfonoyl)-2-[4-(n-hexylsulfonoyl)phenyl]benzo[b]thien-3-yl][4-[2-(1-piperidinyl)ethoxy]-phenyl] methanone

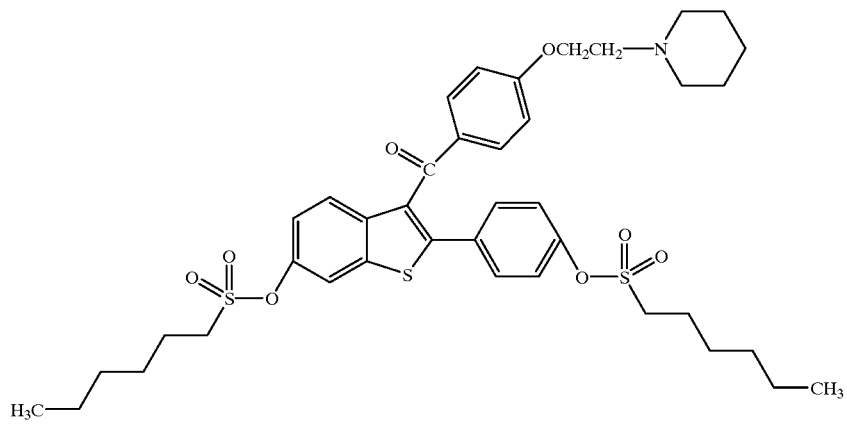

In dry tetrahydrofuran (250 ml) 3 g (5.9 mmol) of [6-hydroxy-2-(4-hydroxyphenyl)-benzo[b]thien-3-yl][4-[2-(1-piperidinyl)ethoxy]phenyl]-methanone hydrochloride was suspended and 10 mg of DMAP was added. Triethylamine (4 g, 40 mmol) was then added and the reaction mixture was stirred for 20 minutes at room temperature under a nitrogen blanket. n-Hexylsulfonyl chloride (3.6 g, 19.6 mmol) in 25 ml of tetrahydrofuran was slowly added to the reaction mixture. The reaction was allowed to proceed at room temperature and under nitrogen for 3 days. The reaction mixture was evaporated down in vacuo and resuspended in ethyl acetate and washed with water. The organic layer was dried by filtering it through anhydrous sodium sulfate and evaporated to a yellow oil. The oil was dissolved in chloroform and chromatographed (HPLC) on a silica gel column and eluted with a linear gradient starting with chloroform and ending with chloroform-methanol (19:1 v/v). The desired fractions were determined by thin layer chromatography, combined and evaporated down to afford 3.14 g of the title compound as a thick oil.

$C_{40}H_{51}NO_8S_3$
NMR: consistent with the proposed structure
MS: (FD) m/e=771 (M+1)

| Elemental Analysis: | C | H | N |
|---|---|---|---|
| Calculated: | 62.39 | 6.68 | 1.82 |
| Found: | 62.33 | 6.62 | 2.03 |

Example 61

Preparation of [6-(n-Hexylsulfonoyl)-2-[4-(n-hexylsulfonoyl)phenyl]benzo[b]thien-3-yl][4-[2-(1-piperidinyl)ethoxy]-phenyl] methanone, Hydrochloride

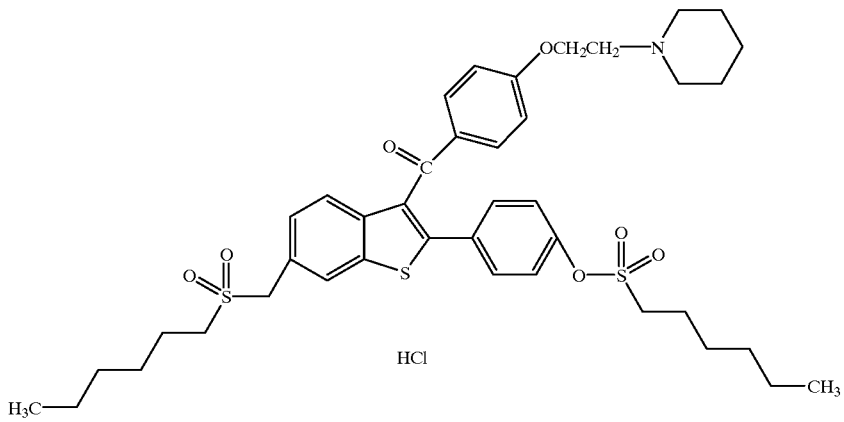

[6-(n-Hexylsulfonoyl)-2-[4-(n-hexylsulfonoyl)phenyl]benzo[b]thien-3-yl][4-[2-(1-piperidinyl)ethoxy]-phenyl] methanone (3 g) was dissolved in 20 ml of ethyl acetate and hydrochloric acid-saturated diethyl ether was added. No precipitate formed. The reaction mixture was evaporated to a thick oil and was triturated several times with diethyl ether and dried in vacuo at room temperature to afford 1.64 g of the title compound as a white amorphous and hygroscopic powder.

NMR: consistent with the proposed structure

| Elemental Analysis: | C | H | N |
|---|---|---|---|
| Calculated: | 59.67 | 6.50 | 1.74 |
| Found: | 59.47 | 6.59 | 1.77 |

$C_{40}H_{51}NO_8S_3 \cdot HCl$

Example 62

Preparation of [6-(n-Butylsulfonoyl)-2-[4-(n-butylsulfonoyl)phenyl]benzo[b]thien-3-yl][4-[2-(1-piperidinyl)ethoxy]-phenyl] methanone, Citrate 2 g (2.8 mmol) of [6-(n-Butylsulfonoyl)-2-[4-(n-butylsulfonoyl)phenyl]benzo[b]thien-3-yl][4-[2-(1-piperidinyl)ethoxy]-phenyl] methanone was dissolved in 200 ml of acetone and 0.63 g (3 mmol) of citric acid was added. The reaction mixture remained at room temperature and under a nitrogen blanket for eighteen hours. The reaction mixture was evaporated in vacuo at 50° C. The reaction mixture was triturated several times with ether and dried at room temperature in vacuo to afford 2.35 g of the title compound as a white amorphous and hygroscopic powder.

| Elemental Analysis: | C | H | N |
|---|---|---|---|
| Calculated: | 55.68 | 5.67 | 1.55 |
| Found: | 55.39 | 5.60 | 1.60 |

NMR: consistent with the proposed structure

Example 63

Preparation of [6-(n-butylsulfonoyl)-2-[4-(n-butylsulfonoyl)phenyl]benzo[b]thien-3-yl][4-[3-(1-piperidinyl)propoxy]phenyl]methanone

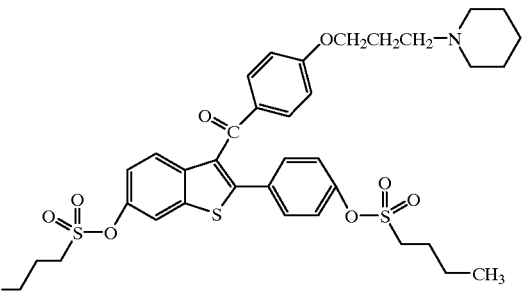

2.5 g (4.77 mmol) of [6-hydroxy-2-[4-hydroxyphenyl]benzo-[b]thien-3-yl][4-[3-(1-piperidinyl)propoxy]-phenyl] methanone hydrochloride was dissolved in 100 ml of tetrahydrofuran, 3.9 g (39 mmol) of triethylamine and 10 mg of DMAP were added. The reaction mixture was stirred for 15 minutes at room temperature and under a nitrogen blanket. 4 g (25.5 mmol) of n-butylsulfonyl chloride in 15 ml of tetrahydrofuran was slowly added. The reaction was allowed to proceed for eighteen hours at room temperature and under nitrogen. The reaction was quenched with the addition of 25 ml methanol and volume reduced in vacuo. The crude product was chromatographed on a silica gel column, eluted with chloroform-methanol (19:1 v/v). The desired fractions were determined by thin layer chromatography, combined, and evaporated to a tan oil.

Example 64

Preparation of [6-(n-butylsulfonoyl)-2-[4-(n-butylsulfonoyl)phenyl]benzo[b]thien-3-yl][4-[3-(1-piperidinyl)propoxy]-phenyl] methanone, hydrochloride

[6-(n-Butylsulfonoyl)-2-[4-(n-butylsulfonoyl)phenyl]-benzo[b]thien-3-yl][4-[3-(1-piperidinyl)propoxy]-phenyl] methanone was dissolved in ethyl acetate-hexane and hydrogen chloride gas was bubbled in. The reaction mixture was evaporated down and chromatographed (HPLC) on a silica gel column eluted with chloroform and then with chloroform-methanol (19:1 v/v). The desired fractions were determined by thin layer chromatography and combined and evaporated down to a tan amorphous powder to afford 2.5 g of the title compound.

NMR: consistent with the proposed structure

MS: (FD) m/e=728 (M-HCl)

| Elemental Analysis: | C | H | N |
|---|---|---|---|
| Calculated: | 58.14 | 6.07 | 1.83 |
| Found: | 57.90 | 6.05 | 1.82 |

$C_{37}H_{46}NO_8S_3$-HCl

Example 65

Preparation of [6-(n-butylsulfonoyl)-2-[4-(n-butylsulfonoyl)phenyl]benzo[b]thien-3-yl][4-[2-(1-pyrrolidinyl)ethoxy]phenyl]methanone 1.5 g of [6-hydroxy-2-[4-hydroxyphenyl]benzo[b]thien-3-yl][4-[2-(1-pyrrolidinyl)ethoxy]-phenyl]methanone hydrochloride (3 mmol) was suspended in 200 ml of tetrahydrofuran. 1.5 g of triethylamine (15 mmol) and 10 mg of 4-N,N-dimethylaminopyridine were added. The reaction mixture was stirred for several minutes under a nitrogen atmosphere. 1.56 g of n-butylsulfonyl chloride (10 mmol) was dissolved in 50 ml of tetrahydrofuran and slowly added to the reaction mixture over a twenty minute period. The reaction mixture was stirred for eighteen hours at room temperature and under a nitrogen atmosphere. The reaction mixture was evaporated to a gum in vacuo. The crude product was suspended in 100 ml of ethyl acetate and washed with sodium bicarbonate solution and subsequently with water. The organic layer was dried by filteration through anhydrous sodium sulfate and evaporated to a yellow oil. The final product was crystallized from hot ethyl acetate-hexane to afford 410 mg of the title compound.

NMR was consistent with the proposed structure

MS: m/e=700 (M+1) FD

| Elemental Analysis: | C | H | N |
|---|---|---|---|
| Calculated: | 60.20 | 5.86 | 2.01 |
| Found: | 59.94 | 5.94 | 2.00 |

MW=699
$C_{35}H_{41}NO_8S$

Example 66

Preparation of [6-(n-butylsulfonoyl)-2-[4-(n-butylsulfonoyl)-phenyl]benzo[b]thien-3-yl]-[4-[2-(1-pyrrolidinyl)ethoxy]-phenyl]methanone hydrochloride;

350 mg of [6-(n-Butylsulfonoyl)-2-[4-Butylsulfonoyl)-phenyl]benzo[b]thien-3-yl]-[4-[2-(1-pyrrolidinyl)ethoxy]-phenyl]methanone (0.5 mmol) was dissolved in 10 ml of ethyl acetate and a saturated solution of hydrogen chloride in ether was added. No precipitate formed and the reaction mixture was evaporated to a gummy, white solid. The product was triturated with diethyl ether (2×) and filtered and dried in vacuo at room temperature to afford 220 mg of the title compound.

NMR: consistent with the proposed structure

| Elemental Analysis: | C | H | N |
|---|---|---|---|
| Calculated | 57.09 | 5.75 | 1.90; |
| Found: | 57.27 | 5.91 | 1.86 |

MW=736.37
$C_{35}H_{41}NO_8S_3$ - HCl

Example 67

Preparation of [6-hydroxy-2-[4-(n-butylsulfonoyl)-phenyl]benzo[b]-thien-3-yl]-[4-[2-(1-piperidinyl)-ethoxy]phenyl]methanone

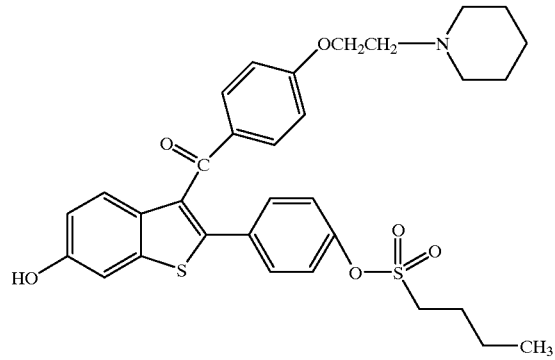

20 g of [6-hydroxy-2-[4-hydroxyphenyl]benzo[b]thien-3-yl]-[4-[2-(1-piperidinyl)ethoxy]phenyl]methanone (Raloxifene) hydrochloride (0.04 mol) was suspended in 250 ml of tetrahydrofuran. Ten grams of triethylamine (0.1 mol) and 10 mg of 4-N,N-dimethylaminopyridine were added. The reaction mixture was stirred for several minutes under nitrogen. 6.25 g of n-butylsulfonylchloride (0.04 mol) was dissolved in 25 ml of tetrahydrofuran and slowly added to the reaction mixture over a period of twenty minutes. The reaction was allowed to continue for 5 days at room temperature and under nitrogen atmosphere. The reaction mixture was evaporated to a gum and suspended in ethyl acetate. The ethyl acetate mixture was washed successively with water, dilute sodium bicarbonate, and water. The ethyl acetate solution was dried by filteration through anhydrous sodium sulfate and evaporated to an amorphous solid.

The resulting solid was dissolved in 50 ml of methylene chloride and chromatographed (HPLC) on a silica gel column eluted with a linear gradient of chloroform to chloroform-methanol (19:1)(v/v). Four fractions were determined by thin layer chromatography and evaporated in vacuo to amorphous solids:

Fraction A: [6-(n-Butylsulfonoyl)-2-[4-(n-butylsulfonoyl)phenyl]benzo[b]thien-3-yl][4-[2-(1-piperidinyl)ethoxy]phenyl] methanone, 5.43 g Fraction B: [6-hydroxy-2-[4-(n-butylsulfonoyl)-phenyl] benzo[b]-thien-3-yl)-[4-[2-(1-piperidinyl)ethoxy] phenyl]methanone, 2.19 g. Rf=0.50, silica gel, CHCl$_3$-MeOH (19:1)v/v Fraction C: [6-(n-butylsulfonoyl)-2-(4-hydroxyphenyl)benzo[b]thien-3-yl]-[4-[2-(1-piperidinyl)ethoxy]phenyl]methanone, 3.60 g Rf=0.41, silica gel, CHCl$_3$-MeOH (19:1)v/v Fraction D: Raloxifene, 3.94 g All of Fraction B was dissolved in hot ethyl acetate and hexane was added and the title compound crystallized out to afford 1.89 g of the title compound.

NMR: consistent with proposed structure
MS: m/e=594(M+1) FD

| Elemental Analysis: | C | H | N |
|---|---|---|---|
| Calculated: | 64.80 | 5.90 | 2.36 |
| Found: | 64.85 | 6.07 | 2.49 |

$C_{32}H_{35}NO_6S_2$

Example 68

Preparation of [6-hydroxy-2-[4-(n-butylsulfonoyl)-phenyl]benzo[b]thien-3-yl]-[4-[2-(1-piperidinyl)ethoxy]phenyl]methanone hydrochloride 1.7 g of [6-hydroxy-2-[4-(n-butylsulfonoyl)-phenyl] benzo[b]-thien-3-yl]-[4-[2-(1-piperidinyl)ethoxy]phenyl] methanone (2.86 mmol) was dissolved in ethyl acetate and a saturated solution of hydrogen chloride-diethyl ether was added. A thick white precipitate formed. The liquid was decanted off. The remaining solid was triturated with diethyl ether (2×) and dried to afford 1.57 g of the title compound as a white amorphous powder.

NMR: consistent with the proposed structure.

| Elemental Analysis: | C | H | N |
|---|---|---|---|
| Calculated: | 60.99 | 5.76 | 2.22; |
| Found: | 61.17 | 5.88 | 2.27 |

MW=630.23

$C_{32}H_{35}NO_6S_2$ - HCl

MS: m/e=594 (M-HCl)F.D.

Example 69

Preparation of [6-n-butylsulfonoyl-2-[4-hydroxyphenyl]benzo[b]thien-3-yl]-[4-[2-(1-piperidinyl)ethoxy]phenyl]methanone

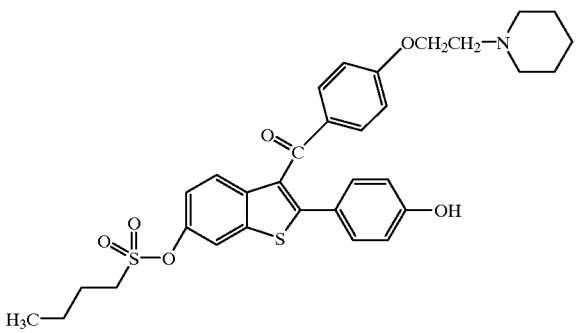

All of fraction C from Example 67 was dissolved in 50 ml of hot ethyl acetate and hexane. No crystallization occurred The solvents were evaporated in vacuo to afford 3.17 g of the title compound as oily, white solid.

NMR: consistent with the proposed structure.

MS: m/e=594 (M+1) FD

| Elemental Analysis: | C | H | N |
|---|---|---|---|
| Calculated: | 64.84 | 5.90 | 2.36. |
| Found: | 64.37 | 5.87 | 2.28. |

MW=593

$C_{32}H_{35}NO_6S$

Example 70

Preparation of [6-n-butylsulfonoyl-2-[4-hydroxyphenyl]benzo[b]thien-3-yl]-[4-[2-(1-piperidinyl)ethoxy]phenyl]methanone hydrochloride 3 g of [6-n-butylsulfonoyl-2-[4-hydroxyphenyl]benzo[b]thien-3-yl]-[4-[2-(1-piperidinyl)ethoxy]phenyl]methanone was dissolved in 50 ml of ethyl acetate and a solution of diethyl ether saturated with hydrogen chloride was added. A thick white precipitate formed and the liquid was decanted off. The solid was triturated (2×) with diethyl ether and dried. This afforded 2.51 g of the title compound as a white amorphous powder.

NMR: consistent with the proposed structure.

| Elemental Analysis: | C | H | N |
|---|---|---|---|
| Calculated: | 60.99 | 5.76 | 2.22; |
| Found: | 60.71 | 5.84 | 2.21 |

MW=630.23

$C_{32}H_{35}NO_6S_2$ - HCl

MS: m/e=594 (M-HCl) F.D.

Example 71

Preparation of [6-[N-(4-chlorophenyl)carbamoyl]-2-[4-[N-(4-chlorophenyl)carbamoyl]phenyl]benzo[b]thien-3-yl][4-[2-(1-piperidinyl)ethoxy]phenyl]methanone

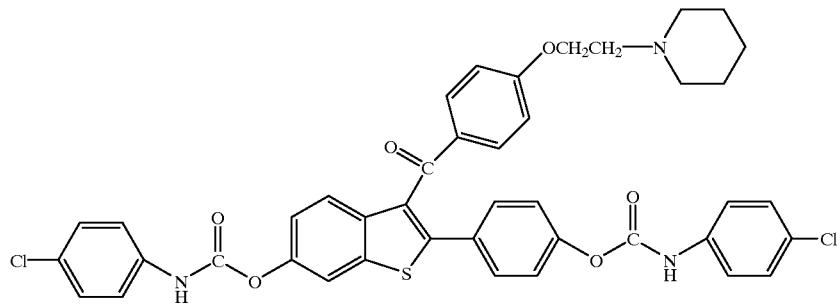

5.56 g (10.7 mmol) of [6-hydroxy-2-(4-hydroxyphenyl)benzo[b]thien-3-yl]-[4-[2-(1-piperidinyl)ethoxy]phenyl]methanone was dissolved in 200 ml of dry tetrahydrofuran and 5.45 g (35.2 mmol) of 4-chlorophenyl isocynate was added. The reaction mixture was stirred at room temperature under an atmosphere of nitrogen. After 18 hours, the solvent was removed by evaporation in vacuo, and redissolved in chloroform. The chloroform solution was cooled to −20° C. for 24 hours and the precipitate formed was filtered off. The remaining solution was chromatographed (Waters Prep 500, HPLC) on a silica gel column, eluted with a linear gradient of chloroform ending with chloroform-methanol (19:1)(v/v). The desired fractions were determined by thin layer chromatography, combined and evaporated to dryness to afford 4.01 g of the title compound as a tan amorphous powder.

$C_{42}C_{35}Cl_2N_3O_6S$

| Elemental Analysis: | C | H | N |
|---|---|---|---|
| Calculated: | 64.64 | 4.48 | 5.38 |
| Found: | 65.69 | 4.81 | 4.83 |

MS (FD) m/e=779,781

Example 72

Preparation of [6-[N-(4-chlorophenyl)carbamoyl]-2-[4-[N-(4-chlorophenyl)carbamoyl]phenyl]benzo[b]thien-3-yl][4-[2-(1-piperidinyl)ethoxy]phenyl]methanone hydrochloride 4.01 g of [6-[N-(4-Chlorophenyl)carbamoyl]-2-[4-[N-(4-chlorophenyl)carbamoyl]phenyl]benzo[b]thien-3-yl][4-[2-(1-piperidinyl)ethoxy]-phenyl] methanone was dissolved in 200 ml of ether and a small amount of tetrahydrofuran added to affect solution. A solution of ether, which had been saturated with hydrogen chloride, was added until no further precipitate formed. The reaction mixture was evaporated to dryness and triturated with ether several times. An attempt was made to crystalize the salt from hot ethyl acetate and absolute EtOH, which did work. Evaporation of the solvent, afforded 2.58 g of the title compound as a tan amorphous powder.

$C_{42}H_{35}Cl_2N_3O_6S \cdot HCl$

| Elemental Analysis: | C | H | N |
|---|---|---|---|
| Calculated: | 61.73 | 4.44 | 5.14 |
| Found: | 57.43 | 4.29 | 4.19 |

NMR: Consistent with the proposed structure and contains an indeterminate amount of solvent.

Example 73

Preparation of [6-(N-(n-butyl)carbamoyl]-2-[4-(N-(n-butyl)carbamoyl)phenyl]benzo[b]thien-3-yl][4-[2-(1-piperidinyl)ethoxy]phenyl] methanone

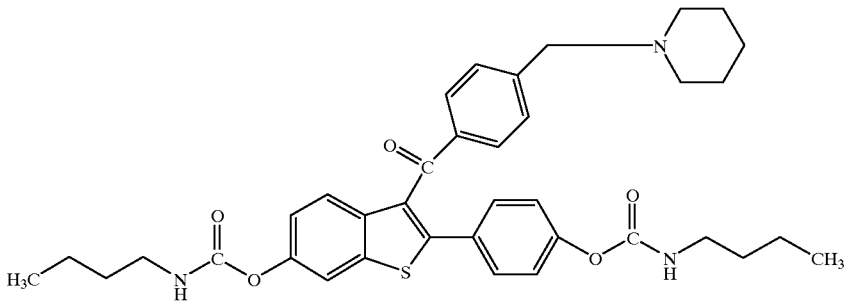

4.47 g (9 mmol) of [6-hydroxy-2-(4-hydroxyphenyl)benzo-[b]thien-3-yl][4-[2-(1-piperidinyl)ethoxy]phenyl] methanone was dissolved in 250 ml of tetrahydrofuran and 4 g (40 mmol) of n-butylisocyanate was added. The reaction mixture, at room temperature and under nitrogen, was allowed to react for 72 hours. The reaction mixture had evaporated by the end of this time and the residue was dissolved in a minimal amount of chloroform. This solution was chromatographed (HPLC) on a silica gel column, eluted with a linear gradient of chloroform to chloroform-methanol (19:1) to afford 4.87 g of the title compound as a tan amorphous powder.

| Elemental Analysis: | C | H | N |
| --- | --- | --- | --- |
| Calculated: | 67.73 | 6.75 | 6.52 |
| Found: | 66.43 | 6.67 | 6.24 |

MS (FD) m/e=672 (M+1)

NMR was consistent with the proposed structure.

Example 74

Preparation of [6-(N-methylcarbamoyl)-2-[4-(N-methylcarbamoyl)phenyl]benzo[b]thien-3-yl][4-[2-(1-piperidinyl)ethoxy]phenyl]methanone

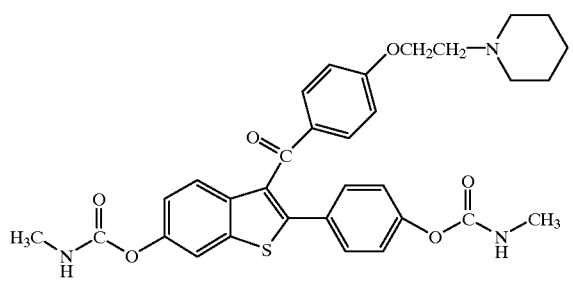

A suspension of 3 g (5.9 mmol) of [6-hydroxy-2(4-hydroxyphenyl)]benzo[b]thien-3-yl][4-[2-(1-piperidinyl)ethoxy]phenyl]methanone hydrochloride in 250 ml of anhydrous tetrahydrofuran was prepared. To this suspension was added 2 g (10 mmol) of triethylamine and the reaction mixture was stirred at room temperature for approximately 15 minutes under a nitrogen atmosphere. To the stirring mixture was added 5.8 g (20 mmol) of methylisocyanate. The reaction was allowed to continue for 36 hours. The reaction mixture was filtered and evapoated to dryness in vacuo. The residue was dissolved in 30 ml of chloroform and chromatographed (HPLC) on a silica gel column, eluted with a linear gradient of solvent of chloroform to chloroform-methanol (19:1). The fractions were analyzed by thin layer chromatography and the desired fractions were combined and evaporated to dryness in vacuo to afford 2.2 g of the title compound as an amorphous powder.

NMR: Consistent with the proposed structure.

IR: 3465, 2942, 1741 cm-1 (CHCl$_3$)

MS: m/e=588 (M+1) FD $C_{32}H_{33}N_3O_6S$.

Example 75

Preparation of [6-(N-methylcarbamoyl)-2[4-(N-methylcarbamoyl)-phenyl]benzo[b]thien-3-yl][4-[2-(1-piperidinyl)ethoxy]phenyl]methanone Hydrochloride Two grams of the compound of [6-(N-Methylcarbamoyl)-2-[4-(N-methylcarbamoyl)-phenyl]benzo[b]thien-3-yl][4-[2-(1-piperidinyl)ethoxy]phenyl]methanone was disolved in 20 ml of ethyl acetate and a solution of hydrochloric acid-ether was added, forming a white precipitate. The reaction mixture was evaporated to dryness in vacuo. The solids were crystallized from acetone-ethyl acetate, filtered and washed with ethyl acetate and dried to afford 1.98 g of the title compound.

NMR: Consistent with the desired structure.

| Elemental Analysis: | C | H | N |
| --- | --- | --- | --- |
| Calculated: | 61.58 | 5.49 | 6.73 |
| Found: | 61.25 | 5.96 | 5.97. |

$C_{32}H_{34}ClN_3O_6S$.

Example 76

Preparation of [6-(N-ethylcarbamoyl)-2-[4-(N-ethylcarbamoyl)phenyl]benzo[b]thien-3-yl][4-[2-(1-piperidinyl)ethoxy]phenyl]methanone

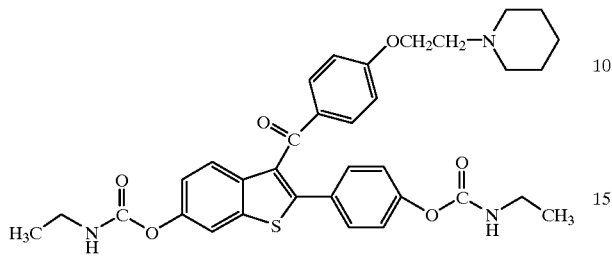

4 g (7.85 mmol) of [6-hydroxy-2-(4-hydroxyphenyl)benzo[b]thien-3-yl][4-[2-(1-piperidinyl)ethoxy]phenyl]methanone hydrochloride was suspended in 250 ml of anhydrous tetrahydrofuran and 3 g (30 mmol) of triethylamine was added. The reaction mixture was stirred at room temperature under nitrogen for 15 minutes.

1.67 g (23.5 mmol) of ethylisocyanate was added. After 24 hours, the reaction was checked by thin layer chromatography, and was not complete. An additional 4.5 g of the isocyanate was added. After 96 hours, the reaction mixture was filtered and chromatographed as in Example 74 to afford 4.23 g of the title compound as a white amorphous powder.

NMR: Consistent with the proposed structure.

EMS: m/e=616 (M+1) FD $C_{34}H_{37}N_3O_6S$.

Example 77

Preparation of [6-(N-ethylcarbamoyl)-2-[4-(N-ethylcarbamoyl)phenyl]benzo[b]thien-3-yl][4-[2-(1-piperidinyl)ethoxy]phenyl]methanone hydrochloride This compound was prepared by substantially the same procedures of Example 75, to afford 3.58 g of the title compound.

NMR: Consistent with the proposed structure.

| Elemental Analysis: | C | H | N |
|---|---|---|---|
| Calculated: | 62.61 | 5.87 | 6.44; |
| Found: | 62.33 | 6.16 | 6.41. |

$C_{34}H_{38}ClN_3O_6S$.

Example 78

Preparation of [6-(N-isopropylcarbamoyl)-2-[4-(N-isopropylcarbamoyl)phenyl]benzo[b]thien-3-yl][4-[2-(1-piperidinyl)ethoxy]phenyl]methanone

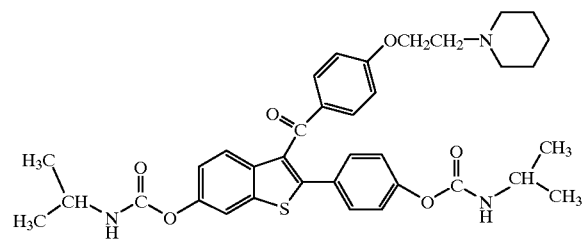

4 g (7.85 mmol) of [6-hydroxy-2-(4-hydroxyphenyl)benzo[b]thien-3-yl][4-[2-(1-piperidinyl)ethoxy]phenyl]methanone hydrochloride was suspended in 250 ml of anhydrous tetrahydrofuran and 3 g (30 mmol) of triethylamine was added. The reaction mixture was stirred for 15 minutes at room temperature and under nitrogen. 2.77 g (32.6 mmol) of isopropylisocyanate was added. After 24 hours, the reaction was checked by thin layer chromatography for completeness and was not complete. An additional 10.8 g (130.4 mmol) of the isocyanate was added and the reaction was allow to continue for another 96 hours. The desired compound was isolated substantially according to the procedures described in Example 19 to afford 4.01 g of the title compound as a tan amorphous powder.

NMR: Consistent with the proposed structure.

Ms: m/e=644 (M+1) FD $C_{36}H_{41}N_3O_6S$.

Example 79

Preparation of [6-(N-isopropylcarbamoyl)-2-[4-(N-isopropylcarbamoyl)phenyl]benzo[b]thien-3-yl]-[4-[2-(1-piperidinyl)ethoxy]phenyl]methanone hydrochloride This compound was prepared by substantially following the procedures of Example 75 to afford 3.58 g of the title compound as a white crystalline powder.

NMR: Consistent with the proposed structure.

| Elemental Analysis: | C | H | N |
|---|---|---|---|
| Calculated: | 63.56 | 6.22 | 6.18 |
| Found: | 63.63 | 6.52 | 5.95 |

$C_{36}H_{42}ClN_3O_6S$.

Example 80

Preparation of [6-(N-cyclohexylcarbamoyl)-2[4-(N-cyclohexylcarbamoyl)phenyl]benzo[b]thienyl-3-yl][4-[2-(1-piperidinyl)ethoxy]phenyl]methanone

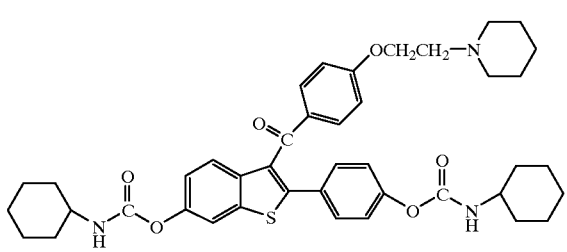

3 g (5.9 mmol) of [6-hydroxy-2-(4-hydroxyphenyl)benzo[b]thien-3-yl][4-[2-(1-piperidinyl)ethoxy]phenyl] methanone hydrochloride was suspended in 250 ml of anhydrous tetrahydrofuran and 2 g (20 mmol) of triethylamine was added. The reaction mixture was stirred for 15 minutes at room temperature under nitrogen. 14.5 g (105 mmol) of cyclohexylisocyanate was added. The reaction was allowed to continue for 48 hours, then an additional 20 mmol of the isocyanate was added. After a further 24 hours, the desired product was isolated substantially according to the procedures of Example 19 to afford 4.07 g of the the title compound as a tan amorphous powder.

NMR: Consistent with the proposed structure.

MS: m/e=724 (M+1) FD $C_{42}H_{49}N_3O_6S$.

Example 81

Preparation of 6-(N-cyclohexylcarbamoyl)-2-[4-(N-cyclohexylcarbamoyl)phenyl]benzo[b]thienyl-3-yl][4-[2-(1-piperidinyl)ethoxy]phenyl]methanone Hydrochloride 3.9 g of 6-(N-cyclohexylcarbamoyl)-2[4-(N-cyclohexylcarbamoyl)phenyl]benzo[b]thienyl-3-yl][4-[2-(1-piperidinyl)ethoxy]phenyl]methanone was converted to its hydrochloride salt by substantially the same procedures as described for Example 75 and crystallized from hot ethyl acetate. This afforded 3 g of the title compound as a white powder.

NMR: Consistent with the proposed structure.

| Elemental Analysis: | C | H | N |
|---|---|---|---|
| Calculated: | 66.34 | 6.63 | 5.53 |
| Found: | 66.32 | 6.92 | 5.62 |

$C_{42}H_{50}ClN_3O_6S$.

Example 82

Preparation of [6-(N-phenylcarbamoyl)-2-[4-(N-phenylcarbamoyl)phenyl]benzo[b]thien-3-yl][4-[2-(1-piperidinyl)ethoxy]phenyl]methanone

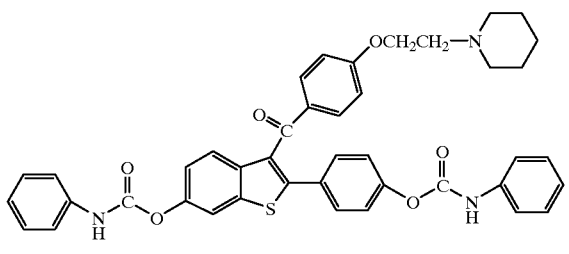

3 g (5.9 mmol) of [6-hydroxy-[2-(4-hydroxyphenyl)benzo [b]thien-3-yl][4-[2-(1-piperidinyl)ethoxy]phenyl] methanone hydrochloride was suspended in 250 ml of anhydrous tetrahydrofuran and 2 g (20 mmol) of triethylamine was added. The reaction mixture was stirred for 15 minutes at room temperature under nitrogen. 15 ml of phenylisocyanate was added and the reaction was allow to continue for 96 hours. An additional 5 ml of isocyanate was added. After a further 48 hours, the reaction mixture was filtered and evaporated to an oil, The oil was triturated with heptane and the liqiud decanted off. The oil was dissolved in chloroform and chromatographed (HPLC) on a silica gel column, eluted with a linear gradient of chloroform to chloroform-methanol (19:1). The desired fractions were combined and evaporated to an oil to afford 3.31 g of the title compound.

NMR: Consistent with the proposed structure.

MS: m/e=711 and some 212 (diphenylurea)

$C_{42}H_{37}N_3O_6S$.

Example 83

Preparation of [6-(N-phenylcarbamoyl)-2-[4-(N-phenylcarbamoyl)phenyl]benzo[b]thien-3-yl][4-[2-(1-piperidinyl)ethoxy]phenyl]methanone Hydrochloride 3.2 g of [6-(N-phenylcarbamoyl)-2[4-(N-phenylcarbamoyl)phenyl]benzo[b]thien-3-yl][4-[2-(1-piperidinyl)ethoxy]phenyl]methanone was disolved in ethyl acetate and filtered. Hydrogen chloride-ether was added to the solution and a white precipitate formed. The liquid was decanted off. The solid was dissolved in a small amount of acetone and filtered, then it is was evaporated to dryness to afford 270 mg of the title compound as a tan amorphous powder.

| Elemental Analysis: | C | H | N |
|---|---|---|---|
| Calculated: | 67.42 | 5.12 | 5.62 |
| Found: | 67.51 | 5.37 | 5.50 |

$C_{42}H_{38}ClN_3O_6S$.

By substantially following the procedures described above one skilled in the art can prepare the other compounds of Formula I. The above groups of compounds are only illustrative of the neuropeptide Y antagonists which are currently under development. This listing of groups of compounds is not meant to be comprehensive, the methods of the present invention may employ any neuropeptide Y antagonist and is not limited to any particular class of compound.

Neuropeptide Y Binding Assay

The ability of the compounds of the instant invention were assessed as to their ability to bind to neuropeptide Y using a protocol essentially as described in M. W. Walker, et al., supra. In this assay the cell line SK-N-MC was employed. This cell line was received from Sloane-Kettering Memorial Hospital, New York. These cells were cultured in T-150 flasks using Dulbecco's Minimal Essential Media (DMEM) supplemented with 5% fetal calf serum. The cells were manually removed from the flasks by scraping, pelleted, and stored at −70° C.

The pellets were resuspended using a glass homogenizer in 25 mM HEPES (pH 7.4) buffer containing 2.5 mM calcium chloride, 1 mM magnesium chloride, and 2 g/L bacitracin. Incubations were performed in a final volume of 200 $\mu$l containing 0.1 nM $^{125}$I-peptide YY (2200 Ci/mmol) and 0.2–0.4 mg protein for about two hours at room temperature.

Nonspecific binding was defined as the amount of radioactivity remaining bound to the tissue after incubating in the presence of 1 $\mu$M neuropeptide Y. In some experiments various concentrations of compounds were included in the incubation mixture.

Incubations were terminated by rapid filtration through glass fiber filters which had been presoaked in 0.3% polyethyleneimine using a 96-well harvester. The filters were washed with 5 ml of 50 mM Tris (pH 7.4) at 4° C. and rapidly dried at 60° C. The filters were then treated with melt-on scintillation sheets and the radioactivity retained on the filters were counted. The results were analyzed using various software packages. Protein concentrations were measured using standard coumassie protein assay reagents using bovine serum albumin as standards.

Many of the compounds prepared supra showed significant activity as neuropeptide Y receptor antagonists.

While it is possible to administer a compound employed in the methods of this invention directly without any formulation, the neuropeptide Y antagonists are usually administered in the form of pharmaceutical compositions comprising a pharmaceutically acceptable excipient and at least one active ingredient. These compositions can be administered by a variety of routes including oral, rectal, transdermal, subcutaneous, intravenous, intramuscular, and intranasal. Many of the compounds employed in the methods of this invention are effective as both injectable and oral compositions. Such compositions are prepared in a manner well known in the pharmaceutical art and comprise at least one active compound. See. e.g., REMINGTON'S PHARMACEUTICAL SCIENCES, (16th ed. 1980).

In making the compositions employed in the present invention the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 0.05 to about 100 mg, more usually about 1.0 to about 30 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

The active compounds are generally effective over a wide dosage range. For examples, dosages per day normally fall within the range of about 0.01 to about 30 mg/kg of body weight. In the treatment of adult humans, the range of about 0.1 to about 15 mg/kg/day, in single or divided dose, is especially preferred. However, it will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

Formulation Preparation 1

Hard gelatin capsules containing the following ingredients are prepared:

| Ingredient | Quantity (mg/capsule) |
| --- | --- |
| Active Ingredient(s) | 30.0 |
| Starch | 305.0 |
| Magnesium stearate | 5.0 |

The above ingredients are mixed and filled into hard gelatin capsules in 340 mg quantities.

Formulation Preparation 2

A tablet formula is prepared using the ingredients below:

| Ingredient | Quantity (mg/tablet) |
|---|---|
| Active Ingredient(s) | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Formulation Preparation 3

A dry powder inhaler formulation is prepared containing the following components:

| Ingredient | Weight % |
|---|---|
| Active Ingredient(s) | 5 |
| Lactose | 95 |

The active mixture is mixed with the lactose and the mixture is added to a dry powder inhaling appliance.

Formulation Preparation 4

Tablets, each containing 30 mg of active ingredient, are prepared as follows:

| Ingredient | Quantity (mg/tablet) |
|---|---|
| Active Ingredient(s) | 30.0 mg |
| Starch | 45.0 mg |
| Microcrystalline cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50–60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Formulation Preparation 5

Capsules, each containing 40 mg of medicament are made as follows:

| Ingredient | Quantity (mg/capsule) |
|---|---|
| Active Ingredient(s) | 40.0 mg |
| Starch | 109.0 mg |
| Magnesium stearate | 1.0 mg |
| Total | 150.0 mg |

The active ingredient, cellulose, starch, and magnesium stearate are blended, passed through a No. 20 mesh U.S. sieve, and filled into hard gelatin capsules in 150 mg quantities.

Formulation Preparation 6

Suppositories, each containing 25 mg of active ingredient are made as follows:

| Ingredient | Amount |
|---|---|
| Active Ingredient(s) | 25 mg |
| Saturated fatty acid glycerides to | 2,000 mg |

The active ingredient(s) is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Preparation 7

Suspensions, each containing 50 mg of medicament per 5.0 ml dose are made as follows:

| Ingredient | Amount |
|---|---|
| Active Ingredient(s) | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 ml |

The medicament, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation Preparation 8

Capsules, each containing 15 mg of medicament, are made as follows:

| Ingredient | Quantity (mg/capsule) |
|---|---|
| Active Ingredient(s) | 15.0 mg |
| Starch | 407.0 mg |
| Magnesium stearate | 3.0 mg |
| Total | 425.0 mg |

The active ingredient(s), cellulose, starch, and magnesium stearate are blended, passed through a No. 20 mesh U.S. sieve, and filled into hard gelatin capsules in 425 mg quantities.

Formulation Preparation 9

An intravenous formulation may be prepared as follows:

| Ingredient | Quantity |
|---|---|
| Active Ingredient(s) | 250.0 mg |
| Isotonic saline | 1000 ml |

Formulation Preparation 10

A topical formulation may be prepared as follows:

| Ingredient | Quantity |
|---|---|
| Active Ingredient(s) | 1–10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Formulation Preparation 11

Sublingual or buccal tablets, each containing 10 mg of active ingredient, may be prepared as follows:

| Ingredient | Quantity Per Tablet |
|---|---|
| Active Ingredient(s) | 10.0 mg |
| Glycerol | 210.5 mg |
| Water | 143.0 mg |
| Sodium Citrate | 4.5 mg |
| Polyvinyl Alcohol | 26.5 mg |
| Polyvinylpyrrolidone | 15.5 mg |
| Total | 410.0 mg |

The glycerol, water, sodium citrate, polyvinyl alcohol, and polyvinylpyrrolidone are admixed together by continuous stirring and maintaining the temperature at about 90° C. When the polymers have gone into solution, the solution is cooled to about 50–55° C. and the medicament is slowly admixed. The homogenous mixture is poured into forms made of an inert material to produce a drug-containing diffusion matrix having a thickness of about 2–4 mm. This diffusion matrix is then cut to form individual tablets having the appropriate size.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system, used for the transport of biological factors to specific anatomical regions of the body, is described in U.S. Pat. No. 5,011,472, issued Apr. 30, 1991, which is herein incorporated by reference.

Indirect techniques, which are generally preferred, usually involve formulating the compositions to provide for drug latentiation by the conversion of hydrophilic drugs into lipid-soluble drugs or prodrugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

The type of formulation employed for the administration of the compounds employed in the methods of the present invention may be dictated by the particular compounds employed, the type of pharmacokinetic profile desired from the route of administration and the compound(s), and the state of the patient.

The administration of the obesity protein may be simultaneous with, before, or after the administration of the neuropeptide Y antagonist. If it is desired to administer the obesity protein simultaneously with the neuropeptide Y antagonist, the two active ingredients may be combined into one pharmaceutical formulation or two formulations may be administered to the patient.

Many factors will dictate the order of administration of the obesity protein and the neuropeptide Y antagonist. Some of these considerations include: the particular compounds employed; the manner in which each active ingredient is formulated; whether the adminstration is prophylactic or curative in nature; and the condition of the patient.

We claim:

1. A method of lowering the production or release of neuropeptide Y which comprises administering to a mammal in need thereof an effective amount of a protein of the formula

```
                     5                  10
Val Pro Ile Gln Lys Val Gln Asp Asp Thr Lys Thr
             15                  20
Leu Ile Lys Thr Ile Val Thr Arg Ile Asn Asp Ile
 25                  30                  35
Ser His Thr Xaa Ser Val Ser Ser Lys Gln Lys Val
                     40                  45
Thr Gly Leu Asp Phe Ile Pro Gly Leu His Pro Ile
     50                  55                  60
Leu Thr Leu Ser Lys Met Asp Gln Thr Leu Ala Val
                     65                  70
Tyr Gln Gln Ile Leu Thr Ser Met Pro Ser Arg Asn
             75                  80
Val Ile Gln Ile Ser Asn Asp Leu Glu Asn Leu Arg
 85                  90                  95
Asp Leu Leu His Val Leu Ala Phe Ser Lys Ser Cys
             100                 105
His Leu Pro Trp Ala Ser Gly Leu Glu Thr Leu Asp
     110                 115                 120
Ser Leu Gly Gly Val Leu Glu Ala Ser Gly Tyr Ser
                     125                 130
Thr Glu Val Val Ala Leu Ser Arg Leu Gln Gly Ser
             135                 140
Leu Gln Asp Met Leu Trp Gln Leu Asp Leu Ser Pro
145
Gly Cys
``` which is SEQ ID NO:1, wherein:
Xaa at position 28 is Gln or absent;
Cys at position 96 is di-sulfide bonded to Cys at position 146;
said protein having at least one of the following substitutions:
Gln at position 4 is replaced with Glu;
Gln at position 7 is replaced with Glu;
Asn at position 22 is replaced with Gln or Asp;
Thr at position 27 is replaced with Ala;
Xaa at position 28 is replaced with Glu;
Gln at position 34 is replaced with Glu;
Met at position 54 is replaced with methionine sulfoxide, Leu, Ile, Val, Ala, or Gly;
Gln at position 56 is replaced with Glu;
Gln at position 62 is replaced with Glu;
Gln at position 63 is replaced with Glu;
Met at position 68 is replaced with methionine sulfoxide, Leu, Ile, Val, Ala, or Gly;
Asn at position 72 is replaced with Gln, Glu, or Asp;
Gln at position 75 is replaced with Glu;
Ser at position 77 is replaced with Ala;
Asn at position 78 is replaced with Gln or Asp;
Asn at position 82 is replaced with Gln or Asp;
His at position 97 is replaced with Gln, Asn, Ala, Gly, Ser, or Pro;
Trp at position 100 is replaced with Ala, Glu, Asp, Asn, Met, Ile, Phe, Tyr, Ser, Thr, Gly, Gln, Val or Leu;
Ala at position 101 is replaced with Ser, Asn, Gly, His, Pro, Thr, or Val;
Ser at position 102 is replaced with Arg;
Gly at position 103 is replaced with Ala;
Glu at position 105 is replaced with Gln;
Thr at position 106 is replaced with Lys or Ser;
Leu at position 107 is replaced with Pro;
Asp at position 108 is replaced with Glu;
Gly at position 111 is replaced with Asp;
Gly at position 118 is replaced with Leu;
Gln at position 130 is replaced with Glu;
Gln at position 134 is replaced with Glu;
Met at position 136 is replaced with methionine sulfoxide, Leu, Ile, Val, Ala, or Gly;
Trp at position 138 is replaced with Ala, Glu, Asp, Asn, Met, Ile, Phe, Tyr, Ser, Thr, Gly, Gln, Val or Leu; or
Gln at position 139 is replaced with Glu;
or a pharmaceutically acceptable salt thereof.

2. A method as claimed in claim 1, employing a protein wherein:
Gln at position 4 is replaced with Glu;
Gln at position 7 is replaced with Glu;
Asn at position 22 is replaced with Gln or Asp;
Thr at position 27 is replaced with Ala;
Gln at position 28 is replaced with Glu;
Gln at position 34 is replaced with Glu;
Met at position 54 is replaced with methionine sulfoxide, Leu, or Ala;
Gln at position 56 is replaced with Glu;
Gln at position 62 is replaced with Glu;
Gln at position 63 is replaced with Glu;
Met at position 68 is replaced with methionine sulfoxide, or Leu;
Asn at position 72 is replaced with Gln or Asp;
Gln at position 75 is replaced with Glu;
Asn at position 78 is replaced with Gln or Asp;
Asn at position 82 is replaced with Gln or Asp;
Gln at position 130 is replaced with Glu;
Gln at position 134 is replaced with Glu;
Met at position 136 is replaced with methionine sulfoxide, Leu, Ile; or
Gln at position 139 is replaced with Glu.

3. A method as claimed in claim 2, employing a protein wherein:
Asn at position 22 is replaced with Gln or Asp;
Thr at position 27 is replaced with Ala;
Met at position 54 is replaced with methionine sulfoxide, Leu, or Ala;
Met at position 68 is replaced with methionine sulfoxide, or Leu;
Asn at position 72 is replaced with Gln or Asp;
Asn at position 78 is replaced with Gln or Asp;
Asn at position 82 is replaced with Gln or Asp; or
Met at position 136 is replaced with methionine sulfoxide, Leu, or Ile.

4. A method as claimed in claim 3, employing a protein wherein:

Asn at position 22 is replaced with Gln or Asp;
Thr at position 27 is replaced with Ala;
Met at position 54 is replaced with Leu, or Ala;
Met at position 68 is replaced with Leu;
Asn at position 72 is replaced with Gln or Asp;
Asn at position 78 is replaced with Gln or Asp;
Asn at position 82 is replaced with Gln or Asp; or
Met at position 136 is replaced with Leu, or Ile.

5. A method as claimed in claim 4, employing the protein:

```
                5                    10
Val Pro Ile Gln Lys Val Gln Asp Asp Thr Lys Thr
            15                   20
Leu Ile Lys Thr Ile Val Thr Arg Ile Asp Asp Ile
25                  30                  35
Ser His Thr Gln Ser Val Ser Ser Lys Gln Lys Val
                40                  45
Thr Gly Leu Asp Phe Ile Pro Gly Leu His Pro Ile
    50                  55                  60
Leu Thr Leu Ser Lys Met Asp Gln Thr Leu Ala Val
                65                  70
Tyr Gln Gln Ile Leu Thr Ser Met Pro Ser Arg Asn
        75                  80
Val Ile Gln Ile Ser Asn Asp Leu Glu Asn Leu Arg
85                  90                  95
Asp Leu Leu His Val Leu Ala Phe Ser Lys Ser Cys
            100                 105
His Leu Pro Trp Ala Ser Gly Leu Glu Thr Leu Asp
    110                 115                 120
Ser Leu Gly Gly Val Leu Glu Ala Ser Gly Tyr Ser
                125                 130
Thr Glu Val Val Ala Leu Ser Arg Leu Gln Gly Ser
        135                 140
Leu Gln Asp Met Leu Trp Gln Leu Asp Leu Ser Pro
```

```
145
Gly Cys
``` which is SEQ ID NO:2.

6. A method as claimed in claim 4 employing the protein

```
                5                    10
Val Pro Ile Gln Lys Val Gln Asp Asp Thr Lys Thr
            15                   20
Leu Ile Lys Thr Ile Val Thr Arg Ile Asn Asp Ile
25                  30                  35
Ser His Ala Gln Ser Val Ser Ser Lys Gln Lys Val
                40                  45
Thr Gly Leu Asp Phe Ile Pro Gly Leu His Pro Ile
    50                  55                  60
Leu Thr Leu Ser Lys Met Asp Gln Thr Leu Ala Val
                65                  70
Tyr Gln Gln Ile Leu Thr Ser Met Pro Ser Arg Asn
        75                  80
Val Ile Gln Ile Ser Asn Asp Leu Glu Asn Leu Arg
85                  90                  95
Asp Leu Leu His Val Leu Ala Phe Ser Lys Ser Cys
            100                 105
His Leu Pro Trp Ala Ser Gly Leu Glu Thr Leu Asp
    110                 115                 120
Ser Leu Gly Gly Val Leu Glu Ala Ser Gly Tyr Ser
                125                 130
Thr Glu Val Val Ala Leu Ser Arg Leu Gln Gly Ser
        135                 140
Leu Gln Asp Met Leu Trp Gln Leu Asp Leu Ser Pro
```

```
145
Gly Cys
``` which is SEQ ID NO:3.

7. A method as claimed in claim 1 employing a protein of the formula:

```
                5              10              15         (II)
        Val Pro Ile Gln Lys Val Gln Asp Asp Thr Lys Thr Leu Ile Lys Thr
                    20                  25                  30
        Ile Val Thr Arg Ile Asn Asp Ile Ser His Thr Xaa Ser Val Ser Ser
                35                  40                  45
        Lys Gln Lys Val Thr Gly Leu Asp Phe Ile Pro Gly Leu His Pro Ile
            50                  55                  60
        Leu Thr Leu Ser Lys Met Asp Gln Thr Leu Ala Val Tyr Gln Gln Ile
        65                  70                  75                  80
        Leu Thr Ser Met Pro Ser Arg Asn Val Ile Gln Ile Ser Asn Asp Leu
                        85                  90                  95
        Glu Asn Leu Arg Asp Leu Leu His Val Leu Ala Phe Ser Lys Ser Cys
                        100                 105                 110
        His Leu Pro Trp Ala Ser Gly Leu Glu Thr Leu Asp Ser Leu Gly Gly
                    115                 120                 125
        Val Leu Glu Ala Ser Gly Tyr Ser Thr Glu Val Val Ala Leu Ser Arg
                130                 135                 140
        Leu Gln Gly Ser Leu Gln Asp Met Leu Trp Gln Leu Asp Leu Ser Pro
```

-continued

```
145
Gly Cys
``` which is SEQ ID NO:4, wherein:

Xaa at position 28 is Gln or absent;

said protein having at least one substitution selected from the group consisting of:

His at position 97 is replaced with Gln, Asn, Ala, Gly, Ser, or Pro;

Trp at position 100 is replaced with Ala, Glu, Asp, Asn, Met, Ile, Phe, Tyr, Ser, Thr, Gly, Gln, Val or Leu;

Ala at position 101 is replaced with Ser, Asn, Gly, His, Pro, Thr, or Val;

Ser at position 102 is replaced with Arg;

Gly at position 103 is replaced with Ala;

Glu at position 105 is replaced with Gln;

Thr at position 106 is replaced with Lys or Ser;

Leu at position 107 is replaced with Pro;

Asp at position 108 is replaced with Glu;

Gly at position 111 is replaced with Asp; or

Trp at position 138 is replaced with Ala, Glu, Asp, Asn, Met, Ile, Phe, Tyr, Ser, Thr, Gly, Gln, Val or Leu;

or a pharmaceutically acceptable salt thereof.

8. A method as claimed in claim 1, employing a protein of the formula

```
                  5                   10
Val Pro Ile Gln Lys Val Gln Asp Asp Thr Lys Thr
             15                  20
Leu Ile Lys Thr Ile Val Thr Arg Ile Asn Asp Ile
 25                  30                  35
Ser His Thr Gln Ser Val Ser Ser Lys Gln Lys Val
                 40                  45
Thr Gly Leu Asp Phe Ile Pro Gly Leu His Pro Ile
     50                  55                  60
Leu Thr Leu Ser Lys Met Asp Gln Thr Leu Ala Val
                 65                  70
Tyr Gln Gln Ile Leu Thr Ser Met Pro Ser Arg Asn
             75                  80
Val Ile Gln Ile Ser Asn Asp Leu Glu Asn Leu Arg
 85                  90                  95
Asp Leu Leu His Val Leu Ala Phe Ser Lys Ser Cys
                100                 105
His Leu Pro Ala Ala Ser Gly Leu Glu Thr Leu Asp
    110                 115                 120
Ser Leu Gly Gly Val Leu Glu Ala Ser Gly Tyr Ser
                125                 130
Thr Glu Val Val Ala Leu Ser Arg Leu Gln Gly Ser
            135                 140
Leu Gln Asp Met Leu Trp Gln Leu Asp Leu Ser Pro
145
Gly Cys
``` which is SEQ ID NO:6, wherein the Cys at position 96 is di-sulfide bonded to Cys at position 146; or a pharmaceutically acceptable salt thereof.

9. A method as claimed in claim 1, employing a protein of the formula:

```
                  5                   10
Val Pro Ile Gln Lys Val Gln Asp Asp Thr Lys Thr
             15                  20
Leu Ile Lys Thr Ile Val Thr Arg Ile Asn Asp Ile
 25                  30                  35
Ser His Thr Gln Ser Val Ser Ser Lys Gln Lys Val
                 40                  45
Thr Gly Leu Asp Phe Ile Pro Gly Leu His Pro Ile
     50                  55                  60
Leu Thr Leu Ser Lys Met Asp Gln Thr Leu Ala Val
                 65                  70
Tyr Gln Gln Ile Leu Thr Ser Met Pro Ser Arg Asn
             75                  80
Val Ile Gln Ile Ser Asn Asp Leu Glu Asn Leu Arg
 85                  90                  95
Asp Leu Leu His Val Leu Ala Phe Ser Lys Ser Cys
                100                 105
His Leu Pro Gln Ala Ser Gly Leu Glu Thr Leu Asp
    110                 115                 120
Ser Leu Gly Gly Val Leu Glu Ala Ser Gly Tyr Ser
                125                 130
Thr Glu Val Val Ala Leu Ser Arg Leu Gln Gly Ser
            135                 140
Leu Gln Asp Met Leu Trp Gln Leu Asp Leu Ser Pro
145
Gly Cys
``` which is SEQ ID NO:7, wherein the Cys at position 96 is di-sulfide bonded to Cys at position 146; or a pharmaceutically acceptable salt thereof.

10. A method as claimed in claim 1, employing a protein of the formula:

```
                  5                   10
Val Pro Ile Gln Lys Val Gln Asp Asp Thr Lys Thr
             15                  20
Leu Ile Lys Thr Ile Val Thr Arg Ile Asn Asp Ile
 25                  30                  35
Ser His Thr Gln Ser Val Ser Ser Lys Gln Lys Val
                 40                  45
Thr Gly Leu Asp Phe Ile Pro Gly Leu His Pro Ile
     50                  55                  60
Leu Thr Leu Ser Lys Met Asp Gln Thr Leu Ala Val
                 65                  70
Tyr Gln Gln Ile Leu Thr Ser Met Pro Ser Arg Asn
             75                  80
Val Ile Gln Ile Ser Asn Asp Leu Glu Asn Leu Arg
 85                  90                  95
Asp Leu Leu His Val Leu Ala Phe Ser Lys Ser Cys
```

-continued

```
                100                     105
His Leu Pro Trp Ala Ser Gly Leu Glu Thr Leu Asp 110                 115                 120
Ser Leu Gly Gly Val Leu Glu Ala Ser Gly Tyr Ser 125                     130
Thr Glu Val Val Ala Leu Ser Arg Leu Gln Gly Ser 135                 140
Leu Gln Asp Met Leu Gln Gln Leu Asp Leu Ser Pro

145
Gly Cys
``` which is SEQ ID NO:8, wherein the Cys at position 96 is di-sulfide bonded to Cys at position 146; or a pharmaceutically acceptable salt thereof.

11. A method as claimed in claim 1, employing a protein of the formula:

```
                  5                      10
Val Pro Ile Gln Lys Val Gln Asp Asp Thr Lys Thr 15                      20
Leu Ile Lys Thr Ile Val Thr Arg Ile Asn Asp Ile 25                       30                      35
Ser His Thr Gln Ser Val Ser Ser Lys Gln Lys Val 40                      45
Thr Gly Leu Asp Phe Ile Pro Gly Leu His Pro Ile 50                      55                      60
Leu Thr Leu Ser Lys Met Asp Gln Thr Leu Ala Val 65                      70
Tyr Gln Gln Ile Leu Thr Ser Met Pro Ser Arg Asn 75                      80
Val Ile Gln Ile Ser Asn Asp Leu Glu Asn Leu Arg 85                       90                      95
Asp Leu Leu His Val Leu Ala Phe Ser Lys Ser Cys 100                     105
His Leu Pro Gln Ala Ser Gly Leu Glu Thr Leu Asp 110                 115                 120
Ser Leu Gly Gly Val Leu Glu Ala Ser Gly Tyr Ser 125                     130
Thr Glu Val Val Ala Leu Ser Arg Leu Gln Gly Ser 135                 140
Leu Gln Asp Met Leu Gln Gln Leu Asp Leu Ser Pro

145
Gly Cys
``` which is SEQ ID NO:9, wherein the Cys at position 96 is di-sulfide bonded to Cys at position 146; or a pharmaceutically acceptable salt thereof.

12. A method as claimed in claim 1, employing a protein of the formula:

```
                  5                      10
Val Pro Ile Gln Lys Val Gln Asp Asp Thr Lys Thr 15                      20
Leu Ile Lys Thr Ile Val Thr Arg Ile Asn Asp Ile 25                       30                      35
Ser His Ala Gln Ser Val Ser Ser Lys Gln Lys Val
```

```
                 40                      45
Thr Gly Leu Asp Phe Ile Pro Gly Leu His Pro Ile 50                      55                      60
Leu Thr Leu Ser Lys Met Asp Gln Thr Leu Ala Val 65                      70
Tyr Gln Gln Ile Leu Thr Ser Met Pro Ser Arg Asn 75                      80
Val Ile Gln Ile Ser Asn Asp Leu Glu Asn Leu Arg 85                       90                      95
Asp Leu Leu His Val Leu Ala Phe Ser Lys Ser Cys 100                     105
His Leu Pro Ala Ala Ser Gly Leu Glu Thr Leu Asp 110                 115                 120
Ser Leu Gly Gly Val Leu Glu Ala Ser Gly Tyr Ser 125                     130
Thr Glu Val Val Ala Leu Ser Arg Leu Gln Gly Ser 135                 140
Leu Gln Asp Met Leu Trp Gln Leu Asp Leu Ser Pro

145
Gly Cys
``` which is SEQ ID NO:10, wherein the Cys at position 96 is di-sulfide bonded to Cys at position 146; or a pharmaceutically acceptable salt thereof.

13. A method as claimed in claim 1, employing a protein of the formula:

```
                  5                      10
Val Pro Ile Gln Lys Val Gln Asp Asp Thr Lys Thr 15                      20
Leu Ile Lys Thr Ile Val Thr Arg Ile Asn Asp Ile 25                       30                      35
Ser His Thr Gln Ser Val Ser Ser Lys Gln Lys Val 40                      45
Thr Gly Leu Asp Phe Ile Pro Gly Leu His Pro Ile 50                      55                      60
Leu Thr Leu Ser Lys Met Asp Gln Thr Leu Ala Val 65                      70
Tyr Gln Gln Ile Leu Thr Ser Met Pro Ser Arg Asn 75                      80
Val Ile Gln Ile Ser Asn Asp Leu Glu Asn Leu Arg 85                       90                      95
Asp Leu Leu His Val Leu Ala Phe Ser Lys Ser Cys 100                     105
His Leu Pro Ala Ala Ser Gly Leu Glu Thr Leu Asp 110                 115                 120
Ser Leu Gly Gly Val Leu Glu Ala Ser Gly Tyr Ser 125                     130
Thr Glu Val Val Ala Leu Ser Arg Leu Gln Gly Ser 135                 140
Leu Gln Asp Met Leu Gln Gln Leu Asp Leu Ser Pro

145
Gly Cys
``` which is SEQ ID NO:11, wherein the Cys at position 96 is di-sulfide bonded to Cys at position 146; or a pharmaceutically acceptable salt thereof.

14. A method of lowering the production or release of neuropeptide Y, which comprises administering a compound as claimed in claim 1 in combination with a compound having activity as a neuropeptide Y antagonist.

15. A method as claimed in claim 14 wherein said neuropeptide Y antagonist is a compound of the formula

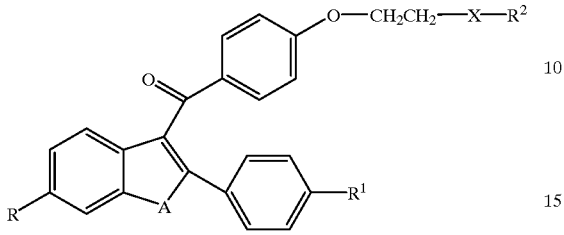

wherein:

A is —O—, —S(O)$_m$—, —N(R$^{11}$)—, —CH$_2$CH$_2$—, or —CH=CH—;

m is 0, 1, or 2;

X is a bond or C$_1$–C$_4$ alkylidenyl;

R$^2$ is a group of the formula

wherein R$^4$ and R$^5$ are independently C$_1$–C$_6$ alkyl or combine to form, along with the nitrogen to which they are attached, a heterocyclic ring selected from the group consisting of hexamethyleneiminyl, piperazino, heptamethyleneiminyl, 4-methylpiperidinyl, imidazolinyl, piperidinyl, pyrrolidinyl, or morpholinyl;

R is hydroxy, halo, hydrogen, C$_3$–C$_8$ cycloalkyl, C$_2$–C$_7$ alkanoyloxy, C$_1$–C$_6$ alkoxy, or phenyl, said phenyl being optionally substituted with one, two, or three moieties selected from the group consisting of C$_1$–C$_4$ alkyl, C$_1$–C$_4$ alkoxy, nitro, chloro, fluoro, trifluoromethyl —OSO$_2$—(C$_1$–C$_{10}$ alkyl) or

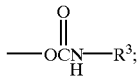

R$^1$ is hydroxy, halo, hydrogen, C$_3$–C$_8$ cycloalkyl, C$_2$–C$_7$ alkanoyloxy, C$_1$–C$_6$ alkoxy, or phenyl, said phenyl being optionally substituted with one, two, or three moieties selected from the group consisting of C$_1$–C$_4$ alkyl, C$_1$–C$_4$ alkoxy, nitro, chloro, fluoro, trifluoromethyl —OSO$_2$—(C$_1$–C$_{10}$ alkyl) or

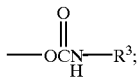

each R$^3$ is independently C$_1$–C$_6$ alkyl, C$_3$–C$_8$ cycloalkyl, unsubstituted or substituted phenyl where the substituent is halo, C$_1$–C$_6$ alkyl or C$_1$–C$_6$ alkoxy;

or a pharmaceutically acceptable salt or solvate therof.

16. A method as claimed in claim 15 employing 6-hydroxy-2-(4-hydroxyphenyl)-3-{4-[2-(piperidin-1-yl)ethoxy]benzoyl}benzo[b]thiophene or its hydrochloride salt.

* * * * *

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
       (A) LENGTH: 146 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO:1:

```
Val Pro Ile Gln Lys Val Gln Asp Asp Thr Lys Thr Leu Ile Lys Thr
1               5                  10                  15

Ile Val Thr Arg Ile Xaa Asp Ile Ser His Xaa Xaa Ser Val Ser Ser
                20                  25                  30

Lys Gln Lys Val Thr Gly Leu Asp Phe Ile Pro Gly Leu His Pro Ile
            35                  40                  45

Leu Thr Leu Ser Lys Xaa Asp Gln Thr Leu Ala Val Tyr Gln Gln Ile
        50                  55                  60

Leu Thr Ser Xaa Pro Ser Arg Xaa Val Ile Gln Ile Xaa Asn Asp Leu
65                  70                  75                  80

Glu Asn Leu Arg Asp Leu Leu His Val Leu Ala Phe Ser Lys Ser Cys
                85                  90                  95

His Leu Pro Trp Ala Ser Gly Leu Glu Thr Leu Asp Ser Leu Gly Gly
            100                 105                 110

Val Leu Glu Ala Ser Xaa Tyr Ser Thr Glu Val Val Ala Leu Ser Arg
        115                 120                 125

Leu Gln Gly Ser Leu Gln Asp Met Leu Trp Gln Leu Asp Leu Ser Pro
    130                 135                 140

Gly Cys
145
```

(2) INFORMATION FOR SEQ ID NO:2:

(i) SEQUENCE CHARACTERISTICS:
       (A) LENGTH: 146 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO:2:

```
Val Pro Ile Gln Lys Val Gln Asp Asp Thr Lys Thr Leu Ile Lys Thr
1               5                  10                  15

Ile Val Thr Arg Ile Asn Asp Ile Ser His Xaa Gln Ser Val Ser Ser
                20                  25                  30

Lys Gln Lys Val Thr Gly Leu Asp Phe Ile Pro Gly Leu His Pro Ile
            35                  40                  45

Leu Thr Leu Ser Lys Met Asp Gln Thr Leu Ala Val Tyr Gln Gln Ile
        50                  55                  60

Leu Thr Ser Met Pro Ser Arg Asn Val Ile Gln Ile Xaa Asn Asp Leu
65                  70                  75                  80
```

```
Glu Asn Leu Arg Asp Leu Leu His Val Leu Ala Phe Ser Lys Ser Cys
                85                  90                  95

His Leu Pro Trp Ala Ser Gly Leu Glu Thr Leu Asp Ser Leu Gly Gly
            100                 105                 110

Val Leu Glu Ala Ser Xaa Tyr Ser Thr Glu Val Val Ala Leu Ser Arg
        115                 120                 125

Leu Gln Gly Ser Leu Gln Asp Met Leu Trp Gln Leu Asp Leu Ser Pro
    130                 135                 140

Gly Cys
145

(2) INFORMATION FOR SEQ ID NO:3:

(i) SEQUENCE CHARACTERISTICS:
        (A) LENGTH: 146 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

Val Pro Ile Gln Lys Val Gln Asp Asp Thr Lys Thr Leu Ile Lys Thr
1               5                   10                  15

Ile Val Thr Arg Ile Asn Asp Ile Ser His Ala Gln Ser Val Ser Ser
            20                  25                  30

Lys Gln Lys Val Thr Gly Leu Asp Phe Ile Pro Gly Leu His Pro Ile
        35                  40                  45

Leu Thr Leu Ser Lys Met Asp Gln Thr Leu Ala Val Tyr Gln Gln Ile
    50                  55                  60

Leu Thr Ser Met Pro Ser Arg Asn Val Ile Gln Ile Ser Asn Asp Leu
65                  70                  75                  80

Glu Asn Leu Arg Asp Leu Leu His Val Leu Ala Phe Ser Lys Ser Cys
                85                  90                  95

His Leu Pro Trp Ala Ser Gly Leu Glu Thr Leu Asp Ser Leu Gly Gly
            100                 105                 110

Val Leu Glu Ala Ser Gly Tyr Ser Thr Glu Val Val Ala Leu Ser Arg
        115                 120                 125

Leu Gln Gly Ser Leu Gln Asp Met Leu Trp Gln Leu Asp Leu Ser Pro
    130                 135                 140

Gly Cys
145

(2) INFORMATION FOR SEQ ID NO:4:

(i) SEQUENCE CHARACTERISTICS:
        (A) LENGTH: 146 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

Val Pro Ile Gln Lys Val Gln Asp Asp Thr Lys Thr Leu Ile Lys Thr
1               5                   10                  15

Ile Val Thr Arg Ile Asn Asp Ile Ser His Thr Xaa Ser Val Ser Ser
            20                  25                  30

Lys Gln Lys Val Thr Gly Leu Asp Phe Ile Pro Gly Leu His Pro Ile
        35                  40                  45
```

```
Leu Thr Leu Ser Lys Met Asp Gln Thr Leu Ala Val Tyr Gln Gln Ile
 50                  55                  60

Leu Thr Ser Met Pro Ser Arg Asn Val Ile Gln Ile Ser Asn Asp Leu
 65                  70                  75                  80

Glu Asn Leu Arg Asp Leu Leu His Val Leu Ala Phe Ser Lys Ser Cys
                 85                  90                  95

His Leu Pro Trp Ala Ser Gly Leu Glu Thr Leu Asp Ser Leu Gly Gly
                100                 105                 110

Val Leu Glu Ala Ser Gly Tyr Ser Thr Glu Val Val Ala Leu Ser Arg
                115                 120                 125

Leu Gln Gly Ser Leu Gln Asp Met Leu Trp Gln Leu Asp Leu Ser Pro
        130                 135                 140

Gly Cys
145
```

(2) INFORMATION FOR SEQ ID NO:5:

(i) SEQUENCE CHARACTERISTICS:
        (A) LENGTH: 458 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

```
CATATGAGGG TACCTATCCA AAAAGTACAA GATGACACCA AAACACTGAT AAAGACAATA    60

GTCACAAGGA TAAATGATAT CTCACACACA CAGTCAGTCT CATCTAAACA GAAAGTCACA   120

GGCTTGGACT TCATACCTGG GCTGCACCCC ATACTGACAT TGTCTAAAAT GGACCAGACA   180

CTGGCAGTCT ATCAACAGAT CTTAACAAGT ATGCCTTCTA GAAACGTGAT ACAAATATCT   240

AACGACCTGG AGAACCTGCG GGATCTGCTG CACGTGCTGG CCTTCTCTAA AAGTTGCCAC   300

TTGCCATGGG CCAGTGGCCT GGAGACATTG GACAGTCTGG GGGGAGTCCT GGAAGCCTCA   360

GGCTATTCTA CAGAGGTGGT GGCCCTGAGC AGGCTGCAGG GTCTCTGCA AGACATGCTG    420

TGGCAGCTGG ACCTGAGCCC CGGGTGCTAA TAGGATCC                           458
```

(2) INFORMATION FOR SEQ ID NO:6:

(i) SEQUENCE CHARACTERISTICS:
        (A) LENGTH: 146 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:6:

```
Val Pro Ile Gln Lys Val Gln Asp Asp Thr Lys Thr Leu Ile Lys Thr
 1                   5                  10                  15

Ile Val Thr Arg Ile Asn Asp Ile Ser His Thr Gln Ser Val Ser Ser
                 20                  25                  30

Lys Gln Lys Val Thr Gly Leu Asp Phe Ile Pro Gly Leu His Pro Ile
                 35                  40                  45

Leu Thr Leu Ser Lys Met Asp Gln Thr Leu Ala Val Tyr Gln Gln Ile
         50                  55                  60

Leu Thr Ser Met Pro Ser Arg Asn Val Ile Gln Ile Ser Asn Asp Leu
 65                  70                  75                  80
```

```
Glu Asn Leu Arg Asp Leu Leu His Val Leu Ala Phe Ser Lys Ser Cys
                 85                  90                  95

His Leu Pro Ala Ala Ser Gly Leu Glu Thr Leu Asp Ser Leu Gly Gly
                100                 105                 110

Val Leu Glu Ala Ser Gly Tyr Ser Thr Glu Val Val Ala Leu Ser Arg
            115                 120                 125

Leu Gln Gly Ser Leu Gln Asp Met Leu Trp Gln Leu Asp Leu Ser Pro
    130                 135                 140

Gly Cys
145
```

(2) INFORMATION FOR SEQ ID NO:7:

(i) SEQUENCE CHARACTERISTICS:
        (A) LENGTH: 146 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:7:

```
Val Pro Ile Gln Lys Val Gln Asp Asp Thr Lys Thr Leu Ile Lys Thr
1               5                  10                  15

Ile Val Thr Arg Ile Asn Asp Ile Ser His Thr Gln Ser Val Ser Ser
                20                  25                  30

Lys Gln Lys Val Thr Gly Leu Asp Phe Ile Pro Gly Leu His Pro Ile
            35                  40                  45

Leu Thr Leu Ser Lys Met Asp Gln Thr Leu Ala Val Tyr Gln Gln Ile
50                  55                  60

Leu Thr Ser Met Pro Ser Arg Asn Val Ile Gln Ile Ser Asn Asp Leu
65                  70                  75                  80

Glu Asn Leu Arg Asp Leu Leu His Val Leu Ala Phe Ser Lys Ser Cys
                85                  90                  95

His Leu Pro Gln Ala Ser Gly Leu Glu Thr Leu Asp Ser Leu Gly Gly
                100                 105                 110

Val Leu Glu Ala Ser Gly Tyr Ser Thr Glu Val Val Ala Leu Ser Arg
            115                 120                 125

Leu Gln Gly Ser Leu Gln Asp Met Leu Trp Gln Leu Asp Leu Ser Pro
    130                 135                 140

Gly Cys
145
```

(2) INFORMATION FOR SEQ ID NO:8:

(i) SEQUENCE CHARACTERISTICS:
        (A) LENGTH: 146 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:8:

```
Val Pro Ile Gln Lys Val Gln Asp Asp Thr Lys Thr Leu Ile Lys Thr
1               5                  10                  15

Ile Val Thr Arg Ile Asn Asp Ile Ser His Thr Gln Ser Val Ser Ser
                20                  25                  30

Lys Gln Lys Val Thr Gly Leu Asp Phe Ile Pro Gly Leu His Pro Ile
            35                  40                  45
```

```
Leu Thr Leu Ser Lys Met Asp Gln Thr Leu Ala Val Tyr Gln Gln Ile
    50                  55                  60

Leu Thr Ser Met Pro Ser Arg Asn Val Ile Gln Ile Ser Asn Asp Leu
65                  70                  75                  80

Glu Asn Leu Arg Asp Leu Leu His Val Leu Ala Phe Ser Lys Ser Cys
                85                  90                  95

His Leu Pro Trp Ala Ser Gly Leu Glu Thr Leu Asp Ser Leu Gly Gly
            100                 105                 110

Val Leu Glu Ala Ser Gly Tyr Ser Thr Glu Val Val Ala Leu Ser Arg
            115                 120                 125

Leu Gln Gly Ser Leu Gln Asp Met Leu Gln Gln Leu Asp Leu Ser Pro
            130                 135                 140

Gly Cys
145

(2) INFORMATION FOR SEQ ID NO:9:

(i) SEQUENCE CHARACTERISTICS:
        (A) LENGTH: 146 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:9:

Val Pro Ile Gln Lys Val Gln Asp Asp Thr Lys Thr Leu Ile Lys Thr
1               5                   10                  15

Ile Val Thr Arg Ile Asn Asp Ile Ser His Thr Gln Ser Val Ser Ser
                20                  25                  30

Lys Gln Lys Val Thr Gly Leu Asp Phe Ile Pro Gly Leu His Pro Ile
            35                  40                  45

Leu Thr Leu Ser Lys Met Asp Gln Thr Leu Ala Val Tyr Gln Gln Ile
    50                  55                  60

Leu Thr Ser Met Pro Ser Arg Asn Val Ile Gln Ile Ser Asn Asp Leu
65                  70                  75                  80

Glu Asn Leu Arg Asp Leu Leu His Val Leu Ala Phe Ser Lys Ser Cys
                85                  90                  95

His Leu Pro Gln Ala Ser Gly Leu Glu Thr Leu Asp Ser Leu Gly Gly
            100                 105                 110

Val Leu Glu Ala Ser Gly Tyr Ser Thr Glu Val Val Ala Leu Ser Arg
            115                 120                 125

Leu Gln Gly Ser Leu Gln Asp Met Leu Gln Gln Leu Asp Leu Ser Pro
            130                 135                 140

Gly Cys
145

(2) INFORMATION FOR SEQ ID NO:10:

(i) SEQUENCE CHARACTERISTICS:
        (A) LENGTH: 146 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:10:

Val Pro Ile Gln Lys Val Gln Asp Asp Thr Lys Thr Leu Ile Lys Thr
1               5                   10                  15
```

```
Ile Val Thr Arg Ile Asn Asp Ile Ser His Ala Gln Ser Val Ser Ser
            20                  25                  30

Lys Gln Lys Val Thr Gly Leu Asp Phe Ile Pro Gly Leu His Pro Ile
            35                  40                  45

Leu Thr Leu Ser Lys Met Asp Gln Thr Leu Ala Val Tyr Gln Gln Ile
            50                  55                  60

Leu Thr Ser Met Pro Ser Arg Asn Val Ile Gln Ile Ser Asn Asp Leu
65                  70                  75                  80

Glu Asn Leu Arg Asp Leu Leu His Val Leu Ala Phe Ser Lys Ser Cys
            85                  90                  95

His Leu Pro Ala Ala Ser Gly Leu Glu Thr Leu Asp Ser Leu Gly Gly
            100                 105                 110

Val Leu Glu Ala Ser Gly Tyr Ser Thr Glu Val Val Ala Leu Ser Arg
            115                 120                 125

Leu Gln Gly Ser Leu Gln Asp Met Leu Trp Gln Leu Asp Leu Ser Pro
            130                 135                 140

Gly Cys
145

(2) INFORMATION FOR SEQ ID NO:11:

(i) SEQUENCE CHARACTERISTICS:
        (A) LENGTH: 146 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:11:

Val Pro Ile Gln Lys Val Gln Asp Asp Thr Lys Thr Leu Ile Lys Thr
1               5                   10                  15

Ile Val Thr Arg Ile Asn Asp Ile Ser His Thr Gln Ser Val Ser Ser
            20                  25                  30

Lys Gln Lys Val Thr Gly Leu Asp Phe Ile Pro Gly Leu His Pro Ile
            35                  40                  45

Leu Thr Leu Ser Lys Met Asp Gln Thr Leu Ala Val Tyr Gln Gln Ile
            50                  55                  60

Leu Thr Ser Met Pro Ser Arg Asn Val Ile Gln Ile Ser Asn Asp Leu
65                  70                  75                  80

Glu Asn Leu Arg Asp Leu Leu His Val Leu Ala Phe Ser Lys Ser Cys
            85                  90                  95

His Leu Pro Ala Ala Ser Gly Leu Glu Thr Leu Asp Ser Leu Gly Gly
            100                 105                 110

Val Leu Glu Ala Ser Gly Tyr Ser Thr Glu Val Val Ala Leu Ser Arg
            115                 120                 125

Leu Gln Gly Ser Leu Gln Asp Met Leu Gln Gln Leu Asp Leu Ser Pro
            130                 135                 140

Gly Cys
145
```